(12) United States Patent
Freeman et al.

(10) Patent No.: US 12,239,841 B2
(45) Date of Patent: *Mar. 4, 2025

(54) MEDICAL DEVICE INTEGRATED WITH PORTABLE DISPLAY AND FUNCTIONALITY

(71) Applicant: ZOLL Medical Corporation, Chelmsford, MA (US)

(72) Inventors: Gary A Freeman, Waltham, MA (US); Paolo Giacometti, North Grafton, MA (US); Timothy F Stever, Lowell, MA (US); Frederick K Newey, Pelham, NH (US); Andrew E Fleischacker, Bedford, NH (US); Suzanne Crowell, Beverly, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 22 days.

This patent is subject to a terminal disclaimer.

(21) Appl. No.: 18/163,435

(22) Filed: Feb. 2, 2023

(65) Prior Publication Data
US 2023/0310875 A1    Oct. 5, 2023

Related U.S. Application Data

(63) Continuation of application No. 16/832,029, filed on Mar. 27, 2020, now Pat. No. 11,596,801.
(Continued)

(51) Int. Cl.
*A61N 1/39*    (2006.01)
(52) U.S. Cl.
CPC ......... *A61N 1/3993* (2013.01); *A61N 1/3904* (2017.08); *A61N 1/3968* (2013.01);
(Continued)

(58) Field of Classification Search
None
See application file for complete search history.

(56) References Cited

U.S. PATENT DOCUMENTS

| 6,127,063 A | 10/2000 | Kowalsky et al. |
| 6,249,105 B1 | 6/2001 | Andrews et al. |

(Continued)

FOREIGN PATENT DOCUMENTS

| CN | 103814499 | 5/2014 |
| GB | 2535139 | 8/2016 |
| WO | 2020079716 | 4/2020 |

OTHER PUBLICATIONS

Gao, Xiang, Low-Power Wireless Charger Transmitter Design Using MC56F8006 DSC, Document No. AN4705. Rev. 0, Mar. 2013, 25 pages.

*Primary Examiner* — Kennedy Schaetzle
(74) *Attorney, Agent, or Firm* — ZOLL Medical Corporation

(57) ABSTRACT

A system is provided for integrating at least one portable computing device with a resuscitative medical device such as a defibrillator. The system may include a carrying case coupled to the resuscitative medical device. The carrying case may include a storage space for the at least one portable computing device and a wireless charging system for charging the at least one portable computing device. The system may be configured to enable secure data transfer between each of the devices, including data communication and data storage. A processor of the resuscitative medical device may be configured to activate the wireless charging system and charge the at least one portable computing device under certain circumstances. The processor may further be configured to prioritize or optimize charging and data transfer between the resuscitative medical device and each of multiple portable computing devices.

25 Claims, 30 Drawing Sheets

Related U.S. Application Data

(60) Provisional application No. 62/825,231, filed on Mar. 28, 2019.

(52) U.S. Cl.
CPC .............. *A61B 2560/0204* (2013.01); *A61B 2560/0271* (2013.01); *A61B 2560/0431* (2013.01); *A61B 2560/045* (2013.01)

(56) References Cited

U.S. PATENT DOCUMENTS

| | | |
|---|---|---|
| 6,422,669 B1 | 7/2002 | Salvatori et al. |
| 6,639,381 B2 | 10/2003 | Tamura et al. |
| 6,873,133 B1 | 3/2005 | Kavounas |
| 7,248,892 B2 | 7/2007 | White et al. |
| 7,570,994 B2 | 8/2009 | Tamura et al. |
| 7,728,548 B2 | 6/2010 | Daynes et al. |
| 8,179,087 B2 | 5/2012 | Neumiller et al. |
| 8,183,823 B2 | 5/2012 | Neumiller et al. |
| 9,143,041 B2 | 9/2015 | Itabashi et al. |
| 9,614,378 B2 | 4/2017 | Golko et al. |
| 9,872,998 B2 | 1/2018 | Aoyama et al. |
| 9,948,134 B2 | 4/2018 | Wojcik |
| 9,973,031 B2 | 5/2018 | Nejatali et al. |
| 10,029,109 B2 | 7/2018 | Beyer et al. |
| 10,112,054 B2 | 10/2018 | Beyer et al. |
| 10,326,488 B2 | 6/2019 | Wojcik |
| 10,886,761 B1 | 1/2021 | Schobben et al. |
| 11,272,861 B1 | 3/2022 | Weiping et al. |
| 11,596,801 B2 * | 3/2023 | Freeman ............... A61B 5/7445 |
| 2008/0097908 A1 | 4/2008 | Dicks et al. |
| 2009/0023481 A1 | 1/2009 | Foster et al. |
| 2010/0081473 A1 | 4/2010 | Chatterjee et al. |
| 2010/0198287 A1 | 8/2010 | Neumiller et al. |
| 2012/0123223 A1 | 5/2012 | Freeman et al. |
| 2012/0187851 A1 | 7/2012 | Huggins et al. |
| 2012/0229071 A1 | 9/2012 | Schuessler |
| 2013/0109371 A1 | 5/2013 | Brogan et al. |
| 2013/0020856 A1 | 8/2013 | Zebrick et al. |
| 2014/0000771 A1 | 1/2014 | Sherman et al. |
| 2014/0021909 A1 | 1/2014 | Klawon et al. |
| 2014/0167688 A1 | 6/2014 | Doyle et al. |
| 2014/0222095 A1 | 8/2014 | Einy |
| 2014/0304773 A1 * | 10/2014 | Woods ................... H04L 63/08 726/3 |
| 2015/0326044 A1 | 11/2015 | Ashley et al. |
| 2015/0366333 A1 | 12/2015 | Zhijian |
| 2016/0094078 A1 | 3/2016 | Graham et al. |
| 2016/0134153 A1 | 5/2016 | Miller et al. |
| 2016/0190817 A1 | 6/2016 | Hartelt et al. |
| 2017/0302099 A1 | 10/2017 | Bolden et al. |
| 2018/0020794 A1 | 1/2018 | Rao |
| 2018/0161586 A1 | 6/2018 | Beyer et al. |
| 2019/0117983 A1 | 4/2019 | Andrews et al. |
| 2020/0006988 A1 | 1/2020 | Leabman |

* cited by examiner

| PORTABLE COMPUTING DEVICE STATE: OFF | | |
|---|---|---|
| PATIENT MONITOR (STATE) | COMPUTING DEVICE (CHARGE) | COMPUTING DEVICE (DATA) |
| PLUGGED IN - ON | ENABLED | OFF |
| PLUGGED IN - STANDBY | ENABLED | OFF |
| PLUGGED IN - OFF | ENABLED | OFF |
| UNPLUGGED - ON | OFF | OFF |
| UNPLUGGED - STANDBY | OFF | OFF |
| UNPLUGGED - OFF | OFF | OFF |
| PORTABLE COMPUTING DEVICE STATE: ON | | |
| PATIENT MONITOR (STATE) | COMPUTING DEVICE (CHARGE) | COMPUTING DEVICE (DATA) |
| PLUGGED IN - ON | ENABLED | ENABLED |
| PLUGGED IN - STANDBY | ENABLED | ENABLED (IF CONFIGURED) |
| PLUGGED IN - OFF | ENABLED | OFF |
| UNPLUGGED - ON | OFF | ENABLED |
| UNPLUGGED - STANDBY | OFF | ENABLED (IF CONFIGURED) |
| UNPLUGGED - OFF | OFF | OFF |
| PORTABLE COMPUTING DEVICE STATE: STANDBY | | |
| PATIENT MONITOR (STATE) | COMPUTING DEVICE (CHARGE) | COMPUTING DEVICE (DATA) |
| PLUGGED IN - ON | ENABLED | ENABLED (IF CONFIGURED) |
| PLUGGED IN - STANDBY | ENABLED | ENABLED (IF CONFIGURED) |
| PLUGGED IN - OFF | ENABLED | OFF |
| UNPLUGGED - ON | OFF | ENABLED (IF CONFIGURED) |
| UNPLUGGED - STANDBY | OFF | ENABLED (IF CONFIGURED) |
| UNPLUGGED - OFF | OFF | OFF |

FIG. 6B

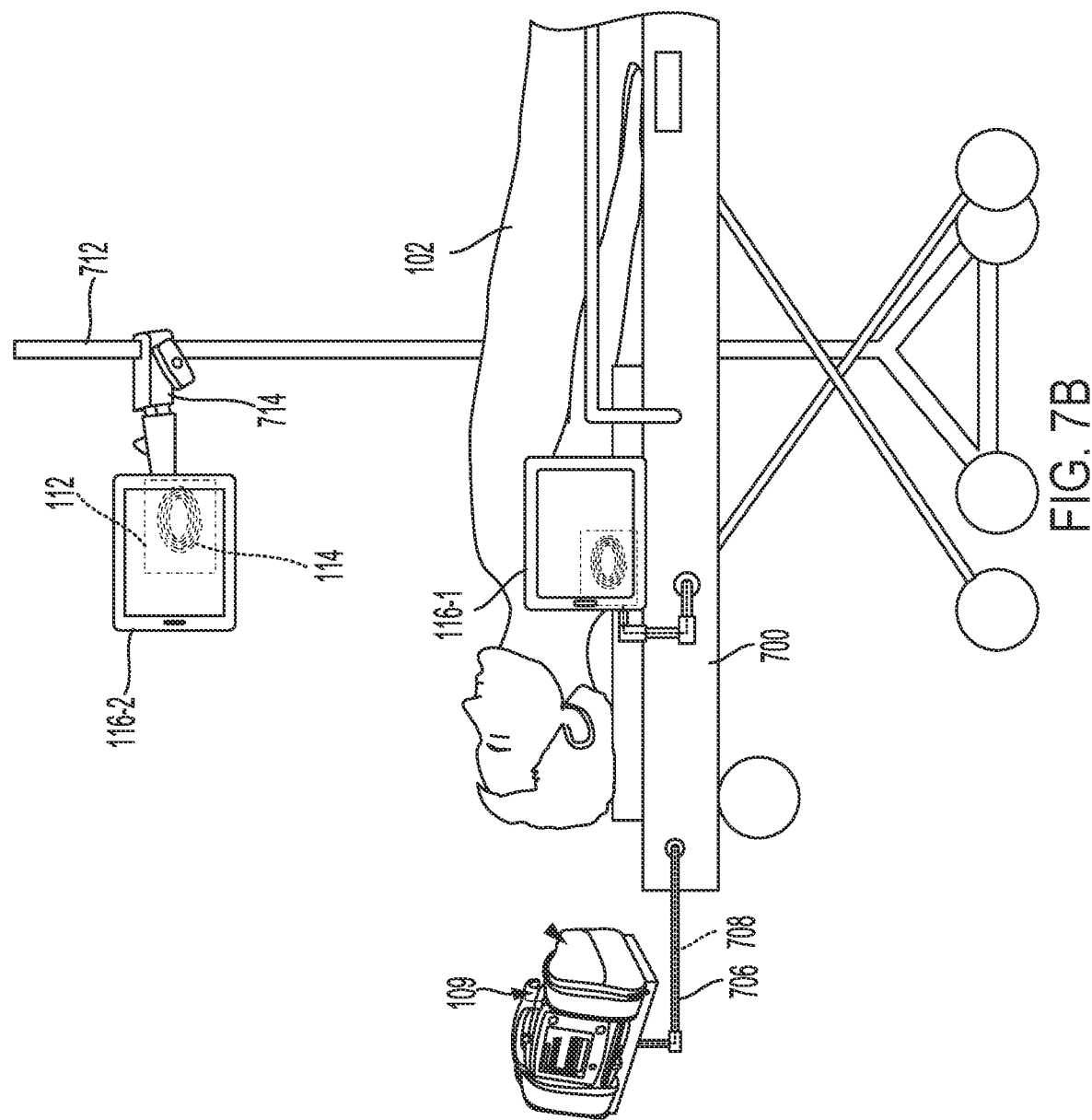

MEDICAL DEVICE INTEGRATED WITH PORTABLE DISPLAY AND FUNCTIONALITY

RELATED APPLICATION

This application is a continuation of U.S. patent application Ser. No. 16/832,029, filed on Mar. 27, 2020, which claims benefit under 35 U.S.C. § 119 (e) to U.S. Provisional Patent Application Ser. No. 62/825,231, filed on Mar. 28, 2019. All subject matter set forth in each of the above referenced applications is hereby incorporated by reference in its entirety into the present application as if fully set forth herein.

BACKGROUND

Acute care is delivered to patients in emergency situations in pre-hospital and hospital settings for patients experiencing a variety of medical conditions. Such medical conditions may involve the diagnosis and treatment of disease states that, if left alone, would likely degenerate into a life-threatening condition and, potentially, death. Stroke, dyspnea (difficulty breathing), traumatic arrest, myocardial infarction, and cardiac arrest are a few examples of disease states for which acute care is delivered to patients in an emergency setting. Cardiac arrest is a serious life-threatening condition that involves the sudden loss of blood flow resulting from an inability of the heart to circulate blood effectively to the body, and it remains a leading cause of death. Other conditions that may be life-threatening include shock, traumatic brain injury, dehydration, kidney failure, congestive heart failure, wound healing, diabetes, stroke, respiratory failure, and orthostatic hypotension.

Despite advances in the field of circulatory enhancement, the need for improved approaches for treating patients with impaired circulation remains an important medical challenge. One example of acute care for treating cardiac arrest is cardiopulmonary resuscitation (CPR). CPR is a process by which one or more rescuers may provide chest compressions and ventilations to a victim who has suffered an adverse cardiac event—by popular terms, a heart attack. During the first five to eight minutes after CPR efforts begin, chest compressions may be the most important element of CPR because chest compressions help maintain circulation through the body and in the heart itself.

Typically, rescuers (e.g., first responders, EMTs or emergency medical technician, caregivers, or other medical personnel like nurses and doctors) utilize resuscitative medical devices such as patient monitors to monitor and treat patients in emergency medical situations. In some cases, the patient monitor may be a monitor/defibrillator that can measure and analyze electrocardiogram signals of the heart of the patient and provide a therapeutic shock (if needed) based on the measured and analyzed electrocardiogram signals. Additionally, the patient monitor may utilize bi-directional wired or wireless communication protocols to communicate with one or more portable computing devices. The bi-directional communication enables the patient monitor to transmit relevant information regarding the condition of the patient and any therapies that may have been provided to the portable computing device. Likewise, the portable computing device may enable a rescuer to interact with the patient to view measured and analyzed information, control the patient monitor to deliver treatment provided to the patient, set event markers related to treatments, and enter patient information, to list a few examples.

SUMMARY

The present system described herein relates to a medical system for providing resuscitative care to a patient and may be used to help manage the response to emergency medical events. Feedback may be provided to a rescuer (e.g., a first responder, paramedic, or EMT that may be rescuer performing CPR) via a patient monitor and/or one or more portable computing devices such as a mobile phone, a tablet computer, or another similar type of mobile computing device such as laptop or personal digital assistants or "PDA." The feedback may include, for example, CPR feedback, such as rate, depth, and CPR interval time, and release velocity, which can be displayed on the patient monitor (e.g., defibrillator), or displayed on the portable computing device such as a tablet computer. A second rescuer may desire to view on a portable computing device, separate from the patient monitor, different information related to a different aspect of the rescue. For example, the rescuer may desire to view information such as a victim heart rate, inspired carbon dioxide, and/or ventilation feedback (e.g., ventilation prompts/information). This additional feedback or other information may provide rescuers with information relating to the effectiveness of the rescuer therapy (e.g., the chest compressions, the effectiveness of ventilations, and the overall condition of the patient). Additionally, the feedback can include prompts and guides to the rescuer that indicate how to improve the effectiveness of the compressions, ventilations, or other therapy. Moreover, this information can be displayed on the portable computing device in addition to information displayed on the patient monitor (e.g., defibrillator).

In some embodiments, the portable computing device may receive input from a rescuer and/or provide information and instructions to the rescuer. For instance, the portable computing device may enable rescuers to control the operation and/or treatment (e.g., pacing and/or defibrillation) of a defibrillator. This may be accomplished with specific application software executed by the external computing device, e.g., an "App." In some examples, the application software can be a generalized app that enables the portable computing device to control various makes and models of defibrillators. In some examples, the application software can be specific to one or more particular brands or models. In other examples, the application software may be "kiosk-type software" that allows users to operate the application software, while not providing access to most other features and functions of the portable computing device.

In order to ensure that the portable computing devices are fully charged or otherwise sufficiently charged and ready for clinical use, a wireless charging system may be integrated into the patient monitor and/or into a carrying case mechanically attached to the patient monitor. The wireless charging system would include one or more transmission coils for wirelessly transmitting energy to receiver coils in the portable computing device. In this way, when the portable computing device is properly aligned and within sufficient proximity to the wireless charging system so as to initiate wireless charging, the portable computing device will automatically begin charging wirelessly. A benefit of this configuration is that the portable computing device extends and enhances the capabilities of the patient monitor through added functionality. Moreover, in case the rescuers inadvertently neglect to plug in the devices for charging, the portable computing device would still be subject to a mechanism that ensures that the device will be adequately charged when the time comes for its usage.

An example is provided of a system for integrating a portable computing device with a resuscitative medical device may include a carrying case mechanically coupled to a resuscitative medical device. The carrying case may comprise a storage space for the portable computing device comprising a protective compartment for storing the portable computing device, and a wireless charging system configured to provide wireless charging for the portable computing device, wherein the wireless charging system is disposed adjacent to the compartment for the portable computing device. The resuscitative medical device may comprise a power storage device for providing power to the resuscitative medical device and a medical device processor configured to detect the presence of the portable computing device in the compartment and activate the wireless charging system if a predetermined condition is present. The portable computing device may comprise a battery configured to be charged by the wireless charging system, and at least one portable computing device processor configured to activate charging of the battery from the wireless charging system in response to a charge level of the battery being below a predefined threshold.

Implementations of such a system may include one or more of the following features. The wireless charging system may comprise at least one transmission induction coil for generating an electromagnetic field from which the portable computing device may be able to receive the energy. The portable computing device may comprise at least one receiving induction coil for receiving the generated electromagnetic field from the at least one transmission induction coil. The portable computing device may comprise a transformer for converting the received electromagnetic field from the at least one receiving induction coil to the energy for charging the battery. The carrying case may comprise at least one receptacle for receiving and orienting the portable computing device, wherein the at least one receptacle may comprise at least one of a rail, guiding component, lock, detent, and fastener.

The at least one receptacle may be a compartment located beneath the resuscitative medical device. The at least one receptacle may be configured to facilitate alignment of the at least one transmission induction coil and the at least one receiving induction coil in the charge transmission position. The charge transmission position may comprise placement of the wireless charging system and the portable computing device within a threshold distance of one another. The threshold distance may comprise distances between 0 cm and 4 cm. The threshold distance may comprise distances between 0.1 cm and 10 cm. The wireless charging system may be configured to activate upon detecting that the power supply of the resuscitative medical device may be receiving the energy from the external energy source. The wireless charging system may be enabled when the power supply of the resuscitative medical device may be receiving the energy from the external energy source. The medical device processor may be configured to deactivate the wireless charging system when the power supply of the resuscitative medical device is not receiving the energy from the external energy source and a power level is below a predefined threshold.

The wireless charging system may comprise a proximity sensor for determining whether the portable computing device is within range for the wireless charging system to provide wireless charging for the portable computing device, wherein the proximity sensor may comprise at least one of an RFID sensor, an NFC sensor, a hall effect sensor, and an optical sensor. The resuscitative medical device may comprise a second proximity sensor for determining whether the portable computing device is within range of the wireless charging system to provide wireless charging for the portable computing device. The proximity sensor may comprise at least one of an RFID sensor, an NFC sensor, a hall effect sensor, and an optical sensor. The portable computing device processor may be configured to determine whether the power supply of the resuscitative medical device may be receiving energy from the external energy source. The resuscitative medical device may be mechanically connected with the wireless charging system.

The resuscitative medical device and the portable computing device are configured for mutual authentication to establish a secure bi-directional communication channel therebetween. The resuscitative medical device may be configured to send to the portable computing device instructions for updating a software configuration. The portable computing device may be configured to provide a status report to the resuscitative medical device.

The status report provides at least one of: an indication of a level of charge of the battery of the portable computing device, an update of data sent from the resuscitative medical device to the portable computing device, and an update of data sent from the portable computing device to the resuscitative medical device. Data sent from the resuscitative medical device to the portable computing device or the data sent from the portable computing device to the resuscitative medical device may comprise patient information. Wherein data sent from the resuscitative medical device to the portable computing device or the data sent from the portable computing device to the resuscitative medical device may comprise software configuration information.

The resuscitative medical device may be configured to provide instructions for the caregiver to deploy the portable computing device from a carrying compartment. The portable computing device may be configured to receive input comprising patient information. The input may be received from at least one of the resuscitative medical device and the user interface of the portable computing device. The at least one medical device processor may be configured to determine whether the power supply may be receiving power from the external energy source, and based on the determination of whether the power supply is receiving power from the external energy source, transmit a signal to activate the portable computing device and initiate communication with the portable computing device.

The system may include at least one sensor configured to provide data to the resuscitative medical device and/or portable computing device and receive the energy from the wireless charging system. The at least one sensor may comprise at least one of a capnography sensor, a blood pressure sensor, an oxygenation sensor, a motion sensor, and an ultrasound transducer. The system may include a mount for mounting the portable computing device to the resuscitative medical device and holding the portable computing device in a plurality of viewing orientations relative to the resuscitative medical device. The system may include a stabilizing holder comprising a support and an actuating arm configured to hold the portable computing device in a stable viewing position relative to a caregiver. The resuscitative medical device may comprise a defibrillator.

The resuscitative medical device may comprise a chest compression sensor input for providing chest compression feedback for the caregiver. The resuscitative medical device may comprise an airflow sensor input for providing ventilation feedback for the caregiver. The system may include a plurality of wireless sensors, the plurality of wireless sensors including at least one of a capnography sensor, a blood pressure sensor, an oxygenation sensor, a motion sensor, and an ultrasound transducer. The carrying case may include a plurality of customized, individual pockets each of the customized, individual pockets stores one of the pluralities of wireless sensors, wherein each of the customized individual pockets includes a wireless charging system each of the wireless charging systems including at least one transmission coil. Each of the plurality of wireless sensors includes a retractable holder affixed the wireless sensor.

Each of the customized individual pockets includes a mount configured to receive the retractable holders affixed to each of the wireless sensors, the mount being configured to secure the wireless sensor and align the wireless sensors to corresponding wireless charging systems in each of the customized, individual pockets. A wireless charging adapter comprising a receiver coil and an interface configured to connect to the portable computing device, the wireless charging adapter configured to receive the energy from the wireless charging system and transfer the received energy to the portable computing device via the interface. The resuscitative medical device includes a detachable handle configured to be removable from the resuscitative medical device. A detachable mount configured to securely hold the portable computing device and securely attach to the resuscitative medical device when the detachable handle is removed from the resuscitative medical device.

The portable computing devices include a retractable holder affixed the portable computing device. The wireless charging system may comprise a mount configured to receive the retractable holder affixed to the portable computing device, the mount being configured to secure the portable computing device and align the portable computing device to the wireless charging system. The wireless charging system includes a charging mat configured to be placed on one or more shelves of a crash cart or one or more shelves of a charging station. The charging mat may comprise a single transmission coil configured to substantially fill the entire surface area of the charging mat. The charging mat may comprise a plurality of transmission coils configured to substantially fill the entire surface area of the charging mat. The charging mat may comprise a plurality of transmission coils of varying size configured to substantially fill the entire surface area of the charging mat. The charging mat may comprise a plurality of transmission coils configured to substantially fill the entire surface area of the charging mat, and configured to be selectively powered in response to a determined alignment of the portable computing device.

The predetermined condition may be based upon whether the resuscitative medical device is connected to an external energy source. The predetermined condition may be based upon whether a charge level of the resuscitative medical device is above a charging threshold. The charging threshold may be 75% or more of a maximum charge of the power storage device of the resuscitative medical device. The charging threshold may be 80% or more of a maximum charge of the power storage device of the resuscitative medical device. The predetermined condition may be based on whether the resuscitative medical device is within proximity to the portable computing device.

The compartment may comprise at least one of: an internal pocket, a receptacle, a mechanical receiving frame, and a series of guiderails. The compartment may comprise one or more fasteners configured to secure the portable computing device. The fasteners include a plurality of magnets disposed within the compartment and corresponding magnets disposed within the portable computing device and configured to align the portable computing device with the wireless charging system. The fasteners include a holder affixed the compartment and a corresponding holder affixed to the portable computing device, the mount and holder configured to align the portable computing device with the wireless charging system. The fasteners include a plurality of magnets disposed within the compartment and corresponding magnets disposed within the portable computing device and configured to align the portable computing device with the wireless charging system. The portable computing device may be approximately 9-11 inches in length, 6-8 inches in width, and less than 0.5 inches in thickness. The portable computing device may be disposed within a protective case.

An example is provided of a system for integrating a portable computing device with a resuscitative medical device comprising a carrying case mechanically coupled to a resuscitative medical device. The carrying case comprising a storage space for the portable computing device comprising a protective compartment for storing the portable computing device. The resuscitative medical device comprising a power storage device for providing power to the resuscitative medical device and a wireless charging system configured to provide wireless charging for the portable computing device, wherein the wireless charging system is disposed adjacent to the compartment for the portable computing device. The system may also include a medical device processor configured to detect the presence of the portable computing device in the compartment and activate the wireless charging system if a predetermined condition is present. The portable computing device may comprise a battery configured to be charged by the wireless charging system, and at least one portable computing device processor configured to activate charging of the battery from the wireless charging system in response to a charge level of the battery being below a predefined threshold.

Implementations of such a system may include one or more of the following features. The wireless charging system may comprise at least one transmission induction coil for generating an electromagnetic field from which the portable computing device may be able to receive the energy The portable computing device may comprise at least one receiving induction coil for receiving the generated electromagnetic field from the at least one transmission induction coil. The portable computing device may comprise a transformer for converting the received electromagnetic field from the at least one receiving induction coil to the energy for charging the battery. The carrying case may comprise at least one receptacle for receiving and orienting the portable computing device, wherein the at least one receptacle may comprise at least one of a rail, guiding component, lock, detent, and fastener.

The at least one receptacle may be a compartment located beneath the resuscitative medical device. The at least one receptacle may be configured to facilitate alignment of the at least one transmission induction coil and the at least one receiving induction coil in the charge transmission position. The charge transmission position may comprise placement of the wireless charging system and the portable computing device within a threshold distance of one another. The threshold distance may comprise distances between 0 cm and 4 cm. The threshold distance may comprise distances between 0.1 cm and 10 cm. The wireless charging system may be configured to activate upon detecting that the power supply of the resuscitative medical device may be receiving the energy from the external energy source. The wireless charging system may be enabled when the power supply of the resuscitative medical device may be receiving the energy from the external energy source. The medical device processor may be configured to deactivate the wireless charging system when the power supply of the resuscitative medical device is not receiving the energy from the external energy source and a power level is below a predefined threshold.

The wireless charging system may comprise a proximity sensor for determining whether the portable computing device is within range for the wireless charging system to provide wireless charging for the portable computing device, wherein the proximity sensor may comprise at least one of an RFID sensor, an NFC sensor, a hall effect sensor, and an optical sensor. The resuscitative medical device may comprise a second proximity sensor for determining whether the portable computing device is within range of the wireless charging system to provide wireless charging for the portable computing device. The proximity sensor may comprise at least one of an RFID sensor, an NFC sensor, a hall effect sensor, and an optical sensor. The portable computing device processor may be configured to determine whether the power supply of the resuscitative medical device may be receiving energy from the external energy source. The resuscitative medical device may be mechanically connected with the wireless charging system.

The resuscitative medical device and the portable computing device are configured for mutual authentication to establish a secure bi-directional communication channel therebetween. The resuscitative medical device may be configured to send to the portable computing device instructions for updating a software configuration. The portable computing device may be configured to provide a status report to the resuscitative medical device.

The status report provides at least one of: an indication of a level of charge of the battery of the portable computing device, an update of data sent from the resuscitative medical device to the portable computing device, and an update of data sent from the portable computing device to the resuscitative medical device. Data sent from the resuscitative medical device to the portable computing device or the data sent from the portable computing device to the resuscitative medical device may comprise patient information. Wherein data sent from the resuscitative medical device to the portable computing device or the data sent from the portable computing device to the resuscitative medical device may comprise software configuration information.

The resuscitative medical device may be configured to provide instructions for the caregiver to deploy the portable computing device from a carrying compartment. The portable computing device may be configured to receive input comprising patient information. The input may be received from at least one of the resuscitative medical device and the user interface of the portable computing device. The at least one medical device processor may be configured to determine whether the power supply may be receiving power from the external energy source, and based on the determination of whether the power supply is receiving power from the external energy source, transmit a signal to activate the portable computing device and initiate communication with the portable computing device.

The system may include at least one sensor configured to provide data to the resuscitative medical device and/or portable computing device and receive the energy from the wireless charging system. The at least one sensor may comprise at least one of a capnography sensor, a blood pressure sensor, an oxygenation sensor, a motion sensor, and an ultrasound transducer. The system may include a mount for mounting the portable computing device to the resuscitative medical device and holding the portable computing device in a plurality of viewing orientations relative to the resuscitative medical device. The system may include a stabilizing holder comprising a support and an actuating arm configured to hold the portable computing device in a stable viewing position relative to a caregiver. The resuscitative medical device may comprise a defibrillator.

The resuscitative medical device may comprise a chest compression sensor input for providing chest compression feedback for the caregiver. The resuscitative medical device may comprise an airflow sensor input for providing ventilation feedback for the caregiver. The system may include a plurality of wireless sensors, the plurality of wireless sensors including at least one of a capnography sensor, a blood pressure sensor, an oxygenation sensor, a motion sensor, and an ultrasound transducer. The carrying case may include a plurality of customized, individual pockets each of the customized, individual pockets stores one of the pluralities of wireless sensors, wherein each of the customized individual pockets may include a wireless charging system each of the wireless charging systems including at least one transmission coil. Each of the plurality of wireless sensors may include a retractable holder affixed the wireless sensor.

Each of the customized individual pockets may include a mount configured to receive the retractable holders affixed to each of the wireless sensors, the mount being configured to secure the wireless sensor and align the wireless sensors to corresponding wireless charging systems in each of the customized, individual pockets. A wireless charging adapter comprising a receiver coil and an interface configured to connect to the portable computing device, the wireless charging adapter configured to receive the energy from the wireless charging system and transfer the received energy to the portable computing device via the interface. The resuscitative medical device may include a detachable handle configured to be removable from the resuscitative medical device. A detachable mount configured to securely hold the portable computing device and securely attach to the resuscitative medical device when the detachable handle is removed from the resuscitative medical device.

The portable computing devices may include a retractable holder affixed the portable computing device. The wireless charging system may comprise a mount configured to receive the retractable holder affixed to the portable computing device, the mount being configured to secure the portable computing device and align the portable computing device to the wireless charging system. The wireless charging system may include a charging mat configured to be placed on one or more shelves of a crash cart or one or more shelves of a charging station. The charging mat may comprise a single transmission coil configured to substantially fill the entire surface area of the charging mat. The charging mat may comprise a plurality of transmission coils configured to substantially fill the entire surface area of the charging mat. The charging mat may comprise a plurality of transmission coils of varying size configured to substantially fill the entire surface area of the charging mat. The charging mat may comprise a plurality of transmission coils configured to substantially fill the entire surface area of the charging mat, and configured to be selectively powered in response to a determined alignment of the portable computing device.

The predetermined condition may be based upon whether the resuscitative medical device is connected to an external energy source. The predetermined condition may be based upon whether a charge level of the resuscitative medical device is above a charging threshold. The charging threshold may be 75% or more of a maximum charge of the power storage device of the resuscitative medical device. The charging threshold may be 80% or more of a maximum charge of the power storage device of the resuscitative medical device. The predetermined condition may be based on whether the resuscitative medical device is within proximity to the portable computing device.

The compartment may comprise at least one of: an internal pocket, a receptacle, a mechanical receiving frame, and a series of guiderails. The compartment may comprise one or more fasteners configured to secure the portable computing device. The fasteners include a plurality of magnets disposed within the compartment and corresponding magnets disposed within the portable computing device and configured to align the portable computing device with the wireless charging system. The fasteners include a holder affixed the compartment and a corresponding holder affixed to the portable computing device, the mount and holder configured to align the portable computing device with the wireless charging system. The fasteners include a plurality of magnets disposed within the compartment and corresponding magnets disposed within the portable computing device and configured to align the portable computing device with the wireless charging system. The portable computing device may be approximately 9-11 inches in length, 6-8 inches in width, and less than 0.5 inches in thickness. The portable computing device may be disposed within a protective case.

An example is provided of a system for integrating a portable computing device with a resuscitative medical device may comprise a carrying case mechanically coupled to a resuscitative medical device. The carrying case may comprise a storage space for the portable computing device comprising a protective compartment for storing the portable computing device. The sys may also include a resuscitative medical device comprising a power storage device for providing power to the resuscitative medical device and a medical device processor. The processor may be configured to detect the presence of the portable computing device in the compartment, transmit a signal to activate the portable computing device based on whether the resuscitative medical device is connected to an external power supply, and establish a secure bi-directional communication channel with the portable computing device. The portable computing device may comprise at least one portable computing device processor configured to receive at least one signal for activation from the resuscitative medical device to cause the portable computing device to power on, and activate data transmission via the bi-directional communication channel with portable computing device in response to the received at least one signal for activation.

Implementations of such a system may include one or more of the following features. The system may comprise a wireless charging system configured to provide wireless charging for the portable computing device, the wireless charging system may be disposed adjacent to the compartment for the portable computing device. The at least one portable computing device processor may be configured to activate the wireless charging system in response to a charge level of the battery being below a predefined threshold. The wireless charging system may comprise at least one transmission induction coil for generating an electromagnetic field from which the portable computing device may be able to receive the energy The portable computing device may comprise at least one receiving induction coil for receiving the generated electromagnetic field from the at least one transmission induction coil. The portable computing device may comprise a transformer for converting the received electromagnetic field from the at least one receiving induction coil to the energy for charging the battery. The carrying case may comprise at least one receptacle for receiving and orienting the portable computing device, wherein the at least one receptacle may comprise at least one of a rail, guiding component, lock, detent, and fastener.

The at least one receptacle may be a compartment located beneath the resuscitative medical device. The at least one receptacle may be configured to facilitate alignment of the at least one transmission induction coil and the at least one receiving induction coil in the charge transmission position. The charge transmission position may comprise placement of the wireless charging system and the portable computing device within a threshold distance of one another. The threshold distance may comprise distances between 0 cm and 4 cm. The threshold distance may comprise distances between 0.1 cm and 10 cm. The wireless charging system may be configured to activate upon detecting that the power supply of the resuscitative medical device may be receiving the energy from the external energy source. The wireless charging system may be enabled when the power supply of the resuscitative medical device may be receiving the energy from the external energy source. The medical device processor may be configured to deactivate the wireless charging system when the power supply of the resuscitative medical device is not receiving the energy from the external energy source and a power level is below a predefined threshold.

The wireless charging system may comprise a proximity sensor for determining whether the portable computing device is within range for the wireless charging system to provide wireless charging for the portable computing device, wherein the proximity sensor may comprise at least one of an RFID sensor, an NFC sensor, a hall effect sensor, and an optical sensor. The resuscitative medical device may comprise a second proximity sensor for determining whether the portable computing device is within range of the wireless charging system to provide wireless charging for the portable computing device. The proximity sensor may comprise at least one of an RFID sensor, an NFC sensor, a hall effect sensor, and an optical sensor. The portable computing device processor may be configured to determine whether the power supply of the resuscitative medical device may be receiving energy from the external energy source. The resuscitative medical device may be mechanically connected with the wireless charging system.

The resuscitative medical device and the portable computing device may be configured for mutual authentication to establish a secure bi-directional communication channel therebetween. The resuscitative medical device may be configured to send to the portable computing device instructions for updating a software configuration. The portable computing device may be configured to provide a status report to the resuscitative medical device.

The status report provides at least one of: an indication of a level of charge of the battery of the portable computing device, an update of data sent from the resuscitative medical device to the portable computing device, and an update of data sent from the portable computing device to the resuscitative medical device. Data sent from the resuscitative medical device to the portable computing device or the data sent from the portable computing device to the resuscitative medical device may comprise patient information. Wherein data sent from the resuscitative medical device to the portable computing device or the data sent from the portable computing device to the resuscitative medical device may comprise software configuration information.

The resuscitative medical device may be configured to provide instructions for the caregiver to deploy the portable computing device from a carrying compartment. The portable computing device may be configured to receive input comprising patient information. The input may be received from at least one of the resuscitative medical device and the user interface of the portable computing device. The at least one medical device processor may be configured to determine whether the power supply may be receiving power from the external energy source, and based on the determination of whether the power supply is receiving power from the external energy source, transmit a signal to activate the portable computing device and initiate communication with the portable computing device.

The system may include at least one sensor configured to provide data to the resuscitative medical device and/or portable computing device and receive the energy from the wireless charging system. The at least one sensor may comprise at least one of a capnography sensor, a blood pressure sensor, an oxygenation sensor, a motion sensor, and an ultrasound transducer. The system may include a mount for mounting the portable computing device to the resuscitative medical device and holding the portable computing device in a plurality of viewing orientations relative to the resuscitative medical device. The system may include a stabilizing holder comprising a support and an actuating arm configured to hold the portable computing device in a stable viewing position relative to a caregiver. The resuscitative medical device may comprise a defibrillator.

The resuscitative medical device may comprise a chest compression sensor input for providing chest compression feedback for the caregiver. The resuscitative medical device may comprise an airflow sensor input for providing ventilation feedback for the caregiver. Plurality of wireless sensors, the plurality of wireless sensors including at least one of a capnography sensor, a blood pressure sensor, an oxygenation sensor, a motion sensor, and an ultrasound transducer. The carrying case may include a plurality of customized, individual pockets each of the customized, individual pockets stores one of the pluralities of wireless sensors, wherein each of the customized individual pockets may include a wireless charging system each of the wireless charging systems including at least one transmission coil. Each of the plurality of wireless sensors may include a retractable holder affixed the wireless sensor.

Each of the customized individual pockets may include a mount configured to receive the retractable holders affixed to each of the wireless sensors, the mount being configured to secure the wireless sensor and align the wireless sensors to corresponding wireless charging systems in each of the customized, individual pockets. A wireless charging adapter comprising a receiver coil and an interface configured to connect to the portable computing device, the wireless charging adapter configured to receive the energy from the wireless charging system and transfer the received energy to the portable computing device via the interface. The resuscitative medical device may include a detachable handle configured to be removable from the resuscitative medical device. A detachable mount configured to securely hold the portable computing device and securely attach to the resuscitative medical device when the detachable handle is removed from the resuscitative medical device.

The portable computing devices may include a retractable holder affixed the portable computing device. The wireless charging system may comprise a mount configured to receive the retractable holder affixed to the portable computing device, the mount being configured to secure the portable computing device and align the portable computing device to the wireless charging system. The wireless charging system may include a charging mat configured to be placed on one or more shelves of a crash cart or one or more shelves of a charging station. The charging mat may comprise a single transmission coil configured to substantially fill the entire surface area of the charging mat. The charging mat may comprise a plurality of transmission coils configured to substantially fill the entire surface area of the charging mat. The charging mat may comprise a plurality of transmission coils of varying size configured to substantially fill the entire surface area of the charging mat. The charging mat may comprise a plurality of transmission coils configured to substantially fill the entire surface area of the charging mat, and configured to be selectively powered in response to a determined alignment of the portable computing device.

The predetermined condition may be based upon whether the resuscitative medical device is connected to an external energy source. The predetermined condition may be based upon whether a charge level of the resuscitative medical device is above a charging threshold. The charging threshold may be 75% or more of a maximum charge of the power storage device of the resuscitative medical device. The charging threshold may be 80% or more of a maximum charge of the power storage device of the resuscitative medical device. The predetermined condition may be based on whether the resuscitative medical device is within proximity to the portable computing device.

The compartment may comprise at least one of: an internal pocket, a receptacle, a mechanical receiving frame, and a series of guiderails. The compartment may comprise one or more fasteners configured to secure the portable computing device. The fasteners include a plurality of magnets disposed within the compartment and corresponding magnets disposed within the portable computing device and configured to align the portable computing device with the wireless charging system. The fasteners include a holder affixed the compartment and a corresponding holder affixed to the portable computing device, the mount and holder configured to align the portable computing device with the wireless charging system. The fasteners include a plurality of magnets disposed within the compartment and corresponding magnets disposed within the portable computing device and configured to align the portable computing device with the wireless charging system. The portable computing device may be approximately 9-11 inches in length, 6-8 inches in width, and less than 0.5 inches in thickness. The portable computing device may be disposed within a protective case. The system may be configured such that when the patient monitor is in an active state, the patient monitor is configured to receive patient information and send the patient information to the portable computing device. The patient monitor may be in the active state when the power supply is receiving power from the external energy source. The patient monitor may be in the active state when the patient monitor is activated while the power supply is not receiving power from the external energy source.

An example is provided of a system for integrating a portable computing device with a resuscitative medical device comprising a carrying case mechanically coupled to a resuscitative medical device. The carrying case may comprise a storage space for the portable computing device comprising a protective compartment for storing the portable computing device. The resuscitative medical device may comprise a power storage device for providing power to the resuscitative medical device. The system may include a medical device processor configured to establish a secure bi-directional communication channel with the portable computing device. The portable computing device may be configured to be affixed to a stabilizing holder and comprising at least one portable computing device processor configured to receive data via the bi-directional communication channel with the resuscitative medical device. Additionally, the stabilizing holder may comprise a support, and at least one actuating arm configured to hold the portable computing device in a stable viewing position relative to a caregiver.

Implementations of such a system may include one or more of the following features. The medical device processor may be configured to detect the presence of the portable computing device in the compartment and activate the wireless charging system if a predetermined condition is present. The carrying case comprises a wireless charging system that may be configured to provide wireless charging for the portable computing device, the wireless charging system may be disposed adjacent to the compartment for the portable computing device. The at least one portable computing device processor may be configured to activate charging of the battery from the wireless charging system in response to a charge level of the battery being below a predefined threshold. The wireless charging system may comprise at least one transmission induction coil for generating an electromagnetic field from which the portable computing device may be able to receive the energy The portable computing device may comprise at least one receiving induction coil for receiving the generated electromagnetic field from the at least one transmission induction coil. The portable computing device may comprise a transformer for converting the received electromagnetic field from the at least one receiving induction coil to the energy for charging the battery. The carrying case may comprise at least one receptacle for receiving and orienting the portable computing device, wherein the at least one receptacle may comprise at least one of a rail, guiding component, lock, detent, and fastener.

The at least one receptacle may be a compartment located beneath the resuscitative medical device. The at least one receptacle may be configured to facilitate alignment of the at least one transmission induction coil and the at least one receiving induction coil in the charge transmission position. The charge transmission position may comprise placement of the wireless charging system and the portable computing device within a threshold distance of one another. The threshold distance may comprise distances between 0 cm and 4 cm. The threshold distance may comprise distances between 0.1 cm and 10 cm. The wireless charging system may be configured to activate upon detecting that the power supply of the resuscitative medical device may be receiving the energy from the external energy source. The wireless charging system may be enabled when the power supply of the resuscitative medical device may be receiving the energy from the external energy source. The medical device processor may be configured to deactivate the wireless charging system when the power supply of the resuscitative medical device is not receiving the energy from the external energy source and a power level is below a predefined threshold.

The wireless charging system may comprise a proximity sensor for determining whether the portable computing device is within range for the wireless charging system to provide wireless charging for the portable computing device, wherein the proximity sensor may comprise at least one of an RFID sensor, an NFC sensor, a hall effect sensor, and an optical sensor. The resuscitative medical device may comprise a second proximity sensor for determining whether the portable computing device is within range of the wireless charging system to provide wireless charging for the portable computing device. The proximity sensor may comprise at least one of an RFID sensor, an NFC sensor, a hall effect sensor, and an optical sensor. The portable computing device processor may be configured to determine whether the power supply of the resuscitative medical device may be receiving energy from the external energy source. The resuscitative medical device may be mechanically connected with the wireless charging system.

The resuscitative medical device and the portable computing device may be configured for mutual authentication to establish a secure bi-directional communication channel therebetween. The resuscitative medical device may be configured to send to the portable computing device instructions for updating a software configuration. The portable computing device may be configured to provide a status report to the resuscitative medical device.

The status report provides at least one of: an indication of a level of charge of the battery of the portable computing device, an update of data sent from the resuscitative medical device to the portable computing device, and an update of data sent from the portable computing device to the resuscitative medical device. Data sent from the resuscitative medical device to the portable computing device or the data sent from the portable computing device to the resuscitative medical device may comprise patient information. Wherein data sent from the resuscitative medical device to the portable computing device or the data sent from the portable computing device to the resuscitative medical device may comprise software configuration information.

The resuscitative medical device may be configured to provide instructions for the caregiver to deploy the portable computing device from a carrying compartment. The portable computing device may be configured to receive input comprising patient information. The input may be received from at least one of the resuscitative medical device and the user interface of the portable computing device. The at least one medical device processor may be configured to determine whether the power supply may be receiving power from the external energy source, and based on the determination of whether the power supply is receiving power from the external energy source, transmit a signal to activate the portable computing device and initiate communication with the portable computing device.

The system may include at least one sensor configured to provide data to the resuscitative medical device and/or portable computing device and receive the energy from the wireless charging system. The at least one sensor may comprise at least one of a capnography sensor, a blood pressure sensor, an oxygenation sensor, a motion sensor, and an ultrasound transducer. The system may include a mount for mounting the portable computing device to the resuscitative medical device and holding the portable computing device in a plurality of viewing orientations relative to the resuscitative medical device. The resuscitative medical device may comprise a defibrillator.

The resuscitative medical device may comprise a chest compression sensor input for providing chest compression feedback for the caregiver. The resuscitative medical device may comprise an airflow sensor input for providing ventilation feedback for the caregiver. The system may include a plurality of wireless sensors, the plurality of wireless sensors including at least one of a capnography sensor, a blood pressure sensor, an oxygenation sensor, a motion sensor, and an ultrasound transducer. The carrying case may include a plurality of customized, individual pockets each of the customized, individual pockets stores one of the pluralities of wireless sensors, wherein each of the customized individual pockets may include a wireless charging system each of the wireless charging systems including at least one transmission coil. Each of the plurality of wireless sensors may include a retractable holder affixed the wireless sensor.

Each of the customized individual pockets may include a mount configured to receive the retractable holders affixed to each of the wireless sensors, the mount being configured to secure the wireless sensor and align the wireless sensors to corresponding wireless charging systems in each of the customized, individual pockets. A wireless charging adapter comprising a receiver coil and an interface configured to connect to the portable computing device, the wireless charging adapter configured to receive the energy from the wireless charging system and transfer the received energy to the portable computing device via the interface. The resuscitative medical device may include a detachable handle configured to be removable from the resuscitative medical device. A detachable mount configured to securely hold the portable computing device and securely attach to the resuscitative medical device when the detachable handle is removed from the resuscitative medical device.

The portable computing devices may include a retractable holder affixed the portable computing device. The wireless charging system may comprise a mount configured to receive the retractable holder affixed to the portable computing device, the mount being configured to secure the portable computing device and align the portable computing device to the wireless charging system. The wireless charging system may include a charging mat configured to be placed on one or more shelves of a crash cart or one or more shelves of a charging station. The charging mat may comprise a single transmission coil configured to substantially fill the entire surface area of the charging mat. The charging mat may comprise a plurality of transmission coils configured to substantially fill the entire surface area of the charging mat. The charging mat may comprise a plurality of transmission coils of varying size configured to substantially fill the entire surface area of the charging mat. The charging mat may comprise a plurality of transmission coils configured to substantially fill the entire surface area of the charging mat, and configured to be selectively powered in response to a determined alignment of the portable computing device.

The predetermined condition may be based upon whether the resuscitative medical device is connected to an external energy source. The predetermined condition may be based upon whether a charge level of the resuscitative medical device is above a charging threshold. The charging threshold may be 75% or more of a maximum charge of the power storage device of the resuscitative medical device. The charging threshold may be 80% or more of a maximum charge of the power storage device of the resuscitative medical device. The predetermined condition may be based on whether the resuscitative medical device is within proximity to the portable computing device.

The compartment may comprise at least one of: an internal pocket, a receptacle, a mechanical receiving frame, and a series of guiderails. The compartment may comprise one or more fasteners configured to secure the portable computing device. The fasteners include a plurality of magnets disposed within the compartment and corresponding magnets disposed within the portable computing device and configured to align the portable computing device with the wireless charging system. The fasteners include a holder affixed the compartment and a corresponding holder affixed to the portable computing device, the mount and holder configured to align the portable computing device with the wireless charging system. The fasteners include a plurality of magnets disposed within the compartment and corresponding magnets disposed within the portable computing device and configured to align the portable computing device with the wireless charging system. The portable computing device may be approximately 9-11 inches in length, 6-8 inches in width, and less than 0.5 inches in thickness. The portable computing device may be disposed within a protective case.

The support may comprise a joint for moving the portable computing device along at least one degree of freedom. The actuating arm may comprise at least two joints for holding the portable computing device in the stable viewing position. The actuating arm may comprise at least one multi-axis gimbal. The at least one inertial sensor may be configured to measure position and orientation of the portable computing device. The stabilizing holder may comprise the at least one inertial sensor. The portable computing device may comprise the at least one inertial sensor. The actuating arm may comprise at least one multi-axis motor. The stabilizing holder may comprise at least one holder processor configured to analyze motion from the at least one inertial sensor and control the multi-axis motor to actuate the arm so that the portable computing device is held in the stable viewing position. The at least one inertial sensor may comprise at least one of an accelerometer, a gyroscope, and an encoder. The support may comprise the patient monitor. The support may comprise at least one of a bracket, a pole, a cart, a soft stretcher, and a mount for coupling the stabilizing holder to the patient. The mount may comprise a coupling component including at least one of a bracket, claw, and hook and loop fasteners.

An example embodiment may provide a system for integrating at least one portable computing device with a resuscitative medical device. The system may include a carrying case mechanically coupled to the resuscitative medical device. The carrying case may include a storage space for a first portable computing device including a protective compartment for storing the first portable computing device. The resuscitative medical device may include a power storage device for providing power to the resuscitative medical device. The resuscitative medical device may further include a medical device processor. The medical device processor may be configured to detect the presence of the first portable computing device in the compartment, transmit a signal to activate the first portable computing device based on whether the resuscitative medical device is connected to an external power supply, and establish a secure bi-directional communication channel with the first portable computing device. The first portable computing device may include at least one portable computing device processor configured to receive at least one signal for activation from the resuscitative medical device to cause the first portable computing device to power on, and activate data transmission via the bi-directional communication channel with the first portable computing device in response to the received at least one signal for activation.

In some embodiments, the system includes one or more additional computing devices, and the carrying case is configured to provide charging through wired or wireless coupling to the first portable computing device and the one or more additional portable computing devices. The carrying case may include storage spaces for each of the one or more additional portable computing devices.

In some embodiments, the system the medical device processor is configured to establish a secure bi-directional communication channel between the resuscitative medical device and each of the first portable computing device and the one or more additional portable computing devices, and between each of the first portable computing device and the one or more additional portable computing devices.

In some embodiments, the first portable computing device is configured to enable storage of medical data obtained from one or more accessories of the first portable computing device, from the resuscitative medical device, and from any of the one or more additional portable computing devices.

In some embodiments, the medical device processor is configured to prioritize or optimize charging between the resuscitative medical device, the first portable computing device, and each of the one or more additional portable computing devices based on set prioritization or optimization parameters. Some of the set prioritization or optimization parameters may be user-configurable through one or more graphical user interfaces provided on at least one of the resuscitative medical device, the first portable computing device, and the one or more additional portable computing devices.

In some embodiments, the medical device processor is configured to optimize charging and data transfer balance between the resuscitative medical device, the first portable computing device, and each of the one or more additional portable computing devices based on set optimization parameters.

In some embodiments, carrying case is configured to detect whether each of the first portable computing device and the one or more additional portable computing devices, when stored, is positioned so as to enable charging, and to provide a user alert regarding storage positioning that does not enable charging.

Furthermore, in some embodiments, the first portable computing device is mounted separate from the resuscitative medical device via a mount configured to enable a user of the portable computing device, when the portable computing device is mounted, to stably move and position the first portable computing device for optimal viewing.

Another example embodiment may provide a system for integrating at least one portable computing device with a resuscitative medical device. The system may include a carrying case mechanically coupled to the resuscitative medical device. The carrying case may include a storage space for a first portable computing device including a protective compartment for storing the first portable computing device. The carrying case may further include a wireless charging system configured to provide wireless charging for the first portable computing device, in which the wireless charging system is disposed adjacent to the compartment for the first portable computing device. The resuscitative medical device may include a power storage device for providing power to the resuscitative medical device, and a medical device processor configured to detect the presence of the first portable computing device in the compartment and activate the wireless charging system if a predetermined condition is present. The first portable computing device may include a battery configured to be charged by the wireless charging system, and at least one portable computing device processor configured to activate charging of the battery from the wireless charging system in response to a charge level of the battery being below a threshold.

Another example embodiment may provide a system for integrating a portable computing device with a resuscitative medical device. The resuscitative medical device may include a power storage device for providing power to the resuscitative medical device. The resuscitative medical device may further include a removable unit including a wireless charging system configured to provide wireless charging for the portable computing device, in which the wireless charging system is disposed adjacent to the portable computing device. The medical device processor may be configured to detect the presence of the portable computing device adjacent to the wireless charging system and activate the wireless charging system if a predetermined condition is present. The portable computing device may include a battery configured to be charged by the wireless charging system, and at least one portable computing device processor configured to activate charging of the battery from the wireless charging system in response to a charge level of the battery being below a predefined threshold.

In some embodiments, the predetermined condition is based on whether the resuscitative medical device is connected to an external energy source, or on whether a charge level of the resuscitative medical device is above a charging threshold.

In some embodiments, the resuscitative medical device is configured such that the removable unit, when in a removed position removed from the resuscitative medical device, can then be stably attached as an integrated part of the resuscitative medical device or, when attached, can then be manually removed from the resuscitative medical device.

In some embodiments, the resuscitative medical device is configured such that any of a plurality of different types of removable units with different components and functions, when in a removed position removed from the resuscitative medical device, can then be stably attached as an integrated part of the resuscitative medical device or, when attached, can then be manually removed from the resuscitative medical device.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

FIG. 6B is a table illustrating exemplary "states" (e.g., ON, STANDBY, OFF) for the patient monitor and the portable computing device, according to one embodiment.

FIG. 7B illustrates another example of how the portable computing device may be used in a clinical situation, according to one embodiment.

DETAILED DESCRIPTION

Figure 1A:
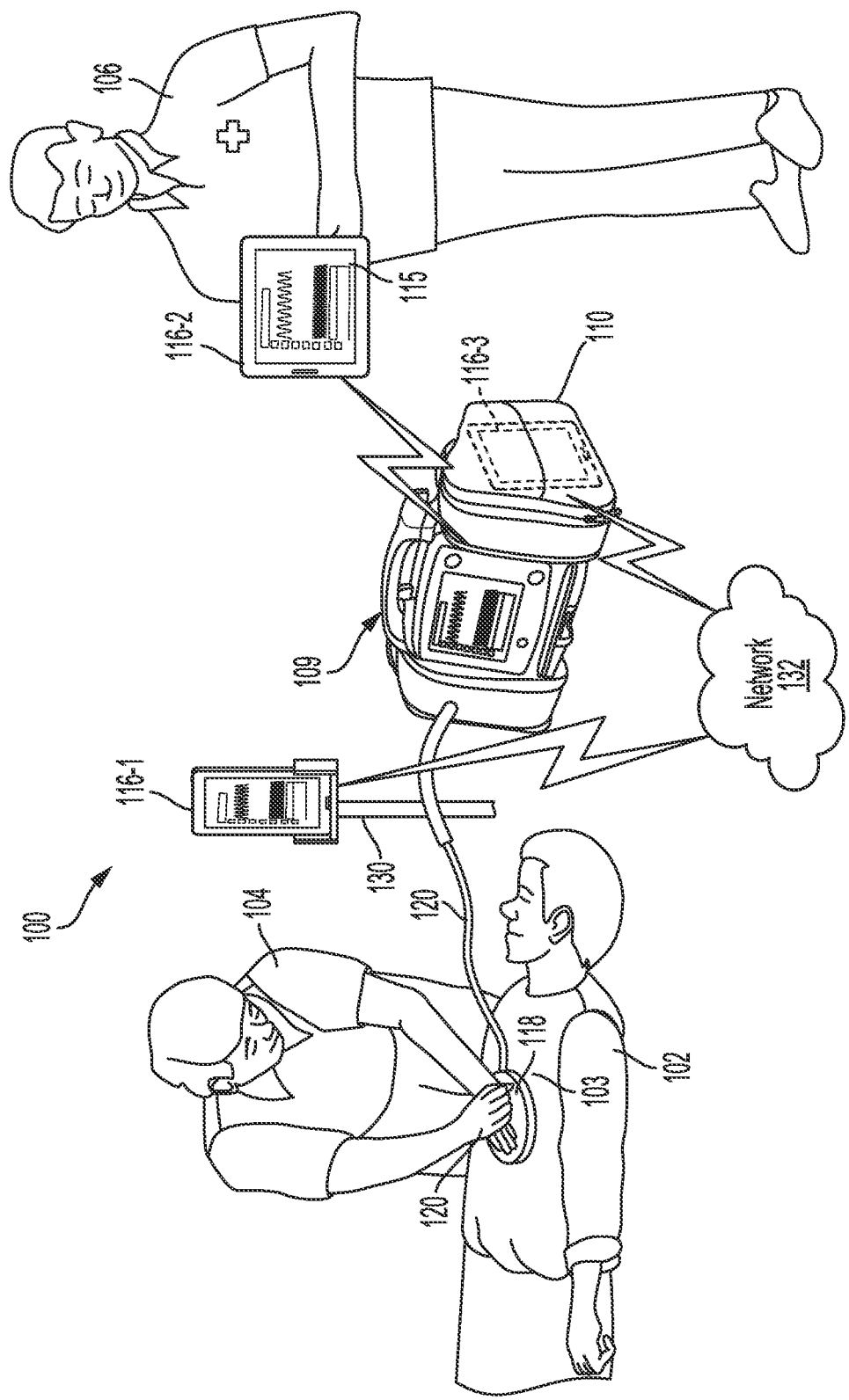
FIG. 1A, a schematic illustration of an example of a medical system, which may include a patient, rescuers, and patient monitor with associated carrying case.

Portable computing devices such as tablets, laptop computers, mobile computing devices, and wearable smart devices (e.g., smart watches), which include batteries and/or other power sources to power said devices, are commonly used in everyday life. Accordingly, it would be helpful for rescuers and/or first responders to be able to easily integrate such devices with their other medical equipment (e.g., defibrillators, ventilators, chest compression equipment, and patient monitors) that are used in providing care to those in need of emergency assistance. Such integration may involve components and an overall design that allows for easy and natural storage and use of the portable computing device(s) to supplement, extend and enhance usage of the associated medical equipment.

For example, in addition to medical sensors, electrode pads, therapy components, and other associated equipment, a patient monitor (e.g., defibrillator/monitor) may come with a portable computing device such as a tablet for the purpose of providing additional functionality, portability, and secondary display of relevant medical information for users of the system. This tablet may advantageously provide a portable, intuitive interface with which a user may conveniently and quickly access or input information that may otherwise be more cumbersome to obtain or enter by navigating on the actual interface of the defibrillator/monitor. In some cases, the tablet functions as an extension of the defibrillator/monitor, with the ability to display all relevant information regularly available on the defibrillator/monitor. Hence, the tablet may be stored in a manner that makes the tablet immediately available and easily ready for use. For instance, when stored in a carrying compartment (e.g., pocket, frame, receptacle, or compartment) associated with the defibrillator/monitor, it would be desirable for the tablet to be fully charged when taken out from the carrying compartment, with all relevant data and software updates completely transferred to the tablet.

This present disclosure relates to systems and methods for wirelessly charging one or more portable computing devices (e.g., tablets, smartphones, smartwatches) and/or additional peripheral devices or sensors (such as capnography sensors, blood pressure sensors, oxygenation sensors, motion sensors, and ultrasound transducers) associated with a resuscitative medical device such as a patient monitor. More specifically, one or more wireless charging systems, which include inductive charging coils, may be provided as part of a patient monitor (e.g., constructed as part of the hardware of a defibrillator/monitor) and/or provided with a carrying case for the patient monitor (e.g., constructed as part of the carrying case that comes with the patient monitor). One example of an electrophysiological monitor may include the ZOLL Propaq M, or alternatively an electrophysiological monitor that incorporates therapy functionality such as pacing, defibrillation, ventilation, or drug delivery. As devices, which are capable of wireless charging, are placed in proximity to the wireless charging system (e.g., typically in the range of 0.1 centimeters to 10 centimeters), the wireless devices will automatically begin charging wirelessly.

In an alternative embodiment, the wireless charging system may be integrated into the patient monitor. As before, the patient monitor may be configured to provide therapeutic treatment to the patient and includes at least one sensor for receiving input signals indicative of one or more physiological measurements of the patient. Likewise, a power supply located within a carrying case and/or the patient monitor may receive energy from an external energy source (e.g., grid power, power bank, generator, or other power sources) and provide energy for the patient monitor to enable the patient monitor to receive and process input signals captured by the one or more sensors. The input signals may be transformed into physiological data based on the physiological measurements. Then, the physiological data may be transmitted to the one or more portable computing devices to enable the data to be further processed (if needed) and displayed on a display of the one or more portable computing devices.

FIG. 1A provides a schematic illustration of an example of a medical system 100, which includes a patient 102, rescuers (also referred to as users or caregivers) 104, 106, a resuscitative medical device (e.g., patient monitor) 109, one or more sensors 118 and an associated carrying case 110, and one or more portable computing devices 116-1 to 116-3.

In general, the resuscitative medical device 109 may be, for example, but not limited to, one or more of a patient monitor, a defibrillator, a mechanical chest compression device (e.g., an automated chest compression device, a belt-based chest compression device, a piston-based chest compression device, a hand-held chest compression device for mechanically assisted chest compressions, an active compression-decompression device, or combinations thereof), a ventilator, an intravenous cooling device, and/or combinations thereof. The medical device may be a wearable device. The resuscitative medical device 109 may include or be coupled to a patient monitor. The ventilator may be a mechanical ventilator. The mechanical ventilator may be a portable, battery-powered ventilator. The intravenous cooling device may deliver cooling therapy and/or may sense a patient's temperature. The medical device may provide, for example, but not limited to, one or more of electrical therapy (e.g., defibrillation, cardiac pacing, synchronized cardioversion, diaphragmatic stimulation, phrenic nerve stimulation, etc.), ventilation therapy, therapeutic cooling, temperature management therapy, invasive hemodynamic support therapy (e.g., extracorporeal membrane oxygenation (ECMO)), and/or combinations thereof.

The resuscitative medical device 109 may incorporate and/or couple (e.g., mechanically, electrically, and/or communicatively) to one or more sensors 118. The one or more sensors 118 may include, for example, but not limited to, cardiac sensing electrodes, chest compression sensor(s), ventilation sensor(s), and/or one or more sensors capable of providing signals indicative of one or more of vital sign(s), electrocardiogram (ECG), blood pressure (e.g., invasive blood pressure (IBP), non-invasive blood pressure (NIBP)), heart rate, pulse oxygen level, respiration rate, heart sounds, lung sounds, respiration sounds, end tidal CO2, saturation of muscle oxygen (SMO2), arterial oxygen saturation (SpO2), cerebral blood flow, electroencephalogram (EEG) signals, brain oxygen level, tissue pH, tissue oxygenation, tissue fluid levels, and/or one or more sensors capable of providing signals indicative of one or more parameters determined via ultrasound, near-infrared reflectance spectroscopy, pneumography, cardiography, ocular impedance, spirometry, tonometry, plethysmography, eye tracking, chest compression parameters (e.g., compression depth, compression rate, compression release, release velocity, distance of active release for active compression-decompression, etc.), ventilation parameters, respiratory parameters, drug delivery parameters, fluid delivery parameters, transthoracic impedance, blood sampling, venous pressure monitoring (e.g., CVP), temperature, pulse oximetry, non-invasive hemoglobin parameters, and/or combinations thereof. In various implementations, the one or more sensors may also provide therapy.

In some embodiments, the patient monitor 109 may be configured to provide instructions (or reminders) for a caregiver to deploy the portable computing device 116 from the carrying case 110. The portable computing devices 116-1 to 116-3 may be mobile computing devices, such as a mobile phone (e.g., an iPhone®), tablet computers (e.g., an iPad®, Galaxy Tab), wearable computing devices such as smartwatches, or smart glasses (e.g., a Glass® wearable computing device), or another type of portable computing device (e.g., laptops or personal digital assistants). In one embodiment, the portable computing device may be a dedicated device configured to run "kiosk software," which is software that only allows one application to be run and typically prevents access to other features and functions of the portable computing device. This software would be designed to enable the portable computing device to be closely integrated with patient monitor 109.

In this example, a first rescuer 104 is providing cardiopulmonary resuscitation (CPR) chest compressions to the chest (or sternum) 103 of the patient 102. A sensor housing 118 comprising one or more sensors and/or other sensors such as a motion, pressure, force, contact, or proximity sensor measures chest compression information (e.g., compression rate, compression depth, force, pressure, acceleration, compression velocity, release velocity, and hold time, to list a few examples). In some embodiments, the sensor housing 118 may be part of an electrode assembly (not shown in this figure) which is an assembly that includes electrodes positioned high on the right side of the victim's torso, a separate electrode positioned low on the left side of the victim's torso, and a sensor located over the victim's sternum. When the sensor is integrated with the electrode assembly, the electrodes may be positioned at locations suitable for acquiring ECG signals and to accommodate a defibrillation pulse transmitted from one electrode through the heart to the opposing electrode. As discussed, when the electrodes are properly placed, the sensor may be positioned at a location suitable for chest compressions to be applied thereon (e.g., sternum).

Additionally, in conjunction with usage of the defibrillator/monitor system, the rescuers 104, 106 may utilize one or more of: a pulse oximeter sensor, blood pressure sensors, ultrasonic transducers, ECG leads, blood glucose monitors, motion sensors, and temperature sensors. These sensors may be communicatively coupled to the patient monitor 109 and/or the portable computing device via wired connections or wirelessly.

The sensor housing 118 may be connected to the patient monitor 109 via a cable 120, which may be able to transmit chest compression information (e.g., rate, depth, acceleration, force, and release time to list a few examples) obtained by the sensors of the sensor housing 118 to the patient monitor 109. The cable 120 may also be able to transmit shock energy from the patient monitor 109 to the patient 102.

As illustrated, a portable computing device 116-1, may be supported by a stand 130 (e.g., mount, holder) to enhance the features of the patient monitor and/or provide another auxiliary display for the rescuer 104. The portable computing device 116-1 may be user configurable to enable the caregiver to select information to be displayed on a display 115 of the portable computing device 116-1. For example, as discussed above for some situations, the rescuer 104 who is providing CPR, may wish to display cardiac information (e.g., ECG waveform, heart rate, pulse oximetry, chest compression rate, and chest compression depth) on the display 115 of the patient monitor 109. Alternatively, another rescuer (not shown) may be providing ventilations and may wish to display ventilation information (e.g., breathing rate, when the next ventilation should be performed, ETCO2, the volume of air provided) on a separate portable computing device (e.g., 116-3).

Further, the portable computing device 116-1 could also display information related to previous treatments (e.g., therapeutic shocks or ventilations) provided, medications administered to the patient as well as the times and dates of when previous treatments or medications were provided. This would enable any other rescuers arriving later to see which treatments had already been provided. Alternatively, these other rescuers could alternatively utilize one of the other portable computing devices e.g., 116-2 to 116-3 to view said information.

In the illustrated embodiment, a second rescuer 106 may also have a portable computing device 116-2. This portable computing device 116-2 may display the same information as displayed on the first portable computing device 116-1 or may display different information selected by the second user. As detailed above, the rescuer may select, e.g., cardiac information, ventilation information, code events, or utilize inputs to enter information or communicate with remote medical personnel (e.g., doctors, dispatch, hospitals).

A third portable computing device 116-3 may be located within a pocket 111 of the carrying case 110. This portable computing device 116-3 may be available for other rescuers that arrive later or may be used by a third rescuer that is part of this rescue team (not shown). The third portable computing device 116-3 may be used to display the same or other types of information not presented on the other portable computing devices 116-1, 116-2. For example, the portable computing device 116-3 may be used by a supervisor that is able to view all information relevant to the rescue effort, or may be able to selectively view information displayed by each of the other portable computing devices. Or, the portable computing device 116-3 may be used as a documenting tool, or may provide information useful for drug therapy/administration.

Each of the portable computing devices 116-1 to 116-3 communicate with each other via the network 132 as well as the patient monitor 109. The network could be a Wi-Fi or wireless telephone network (e.g., 3G/4G/5G wireless mobile telecommunication network). The network 132 enables each portable computing device 116-1 to 116-3 to be individually controllable, but also enables all of the devices to share information with all of the other devices and the patient monitor 109. This ensures that if relevant information is entered by one rescuer (e.g., that medication was administered), that this information may be transmitted to all of the devices (e.g., in the case of medication administration, to prevent another rescuer from unintentionally proving an undesirable double dose). In some embodiments, one device may be programmed to be a master device, which enables this device to control the other devices, but not be controlled by the other devices.

While the illustrated embodiment describes three portable computing devices, four or more portable computing devices could also be utilized, for similar or different purposes. Similarly, the system 100 may only utilize one or two portable computing devices.

Some specific examples of information that can be transferred between the patient monitor 109 or portable computing devices include ECG waveforms, ETCO2 waveforms, SpO2 information, patient vital signs (e.g., such as heart rate, blood pressure, temperature, etc.), chest compression feedback, chest compression rate, chest compression depth, forces associated with chest compressions, pressure associated with chest compressions and/or ventilations, chest compression release velocity, event markers (set by either the rescuers using the portable computing device or the patient monitor), drugs/medications administered, snapshots of physiological data (e.g., portions of information such as ECG that may relevant from the patient having just received a shock or medication), treatment logs, CO2, blood pressure, tidal volume of air provided during ventilation, cue for when to provide a ventilation, ventilation rate, and/or breaths per minute, to list a few non-limiting examples.

While not illustrated in the figures, rescuers may utilize a ventilator (e.g., bag valve mask or automated portable ventilator such as the Z Vent or EMV+ by made by ZOLL MEDICAL of Chelmsford, Mass.), which may establish a connection with an associated portable computing device. The ventilator may comprise an airflow sensor for measuring ventilation information and provide ventilation feedback for the caregiver to administer ventilations according to desired tidal volume and ventilation rate.

In one example, the portable computing devices 116-1 to 116-3 may mirror the information that is displayed on the patient monitor. Alternatively, the rescuers 104, 106 may elect to display different/separate information in accordance with the responsibilities associated with the particular rescuer using the portable computing device. This allows the rescuers 104, 106 to customize the information displayed. For example, if one rescuer is providing CPR, that rescuer may desire to see heart rate information, ECG waveform, as well as information related to the depth and rate of chest compressions, which serves to provide feedback to the rescuer as to the overall quality of chest compressions being administered. The second rescuer may be performing manual ventilations and desire to see other information related to ventilations (e.g., when to provide ventilation, a volume of air provided, ventilation rate, or breaths per minute), which serves to provide feedback to the rescuer as to the overall quality of ventilations being administered. Or, the rescuer may be a supervisor (e.g., physician, lead medic) whose responsibility is to oversee the activities of the other rescuers, as well as to monitor the condition of the patient. Accordingly, it may be preferable for the portable computing device that the supervisor is viewing to display patient vital sign information and, in some cases, a higher level indication of whether other rescuers are performing their tasks in a satisfactory manner. For example, while it may not be necessary for the supervisor to be provided with chest compression information on a compression-by-compression basis, or ventilation information on a ventilation-by-ventilation basis, it may be preferable for the supervisor to be provided with an overall indicator of whether the rescuer performing chest compressions and/or the rescuer performing ventilations are conforming to the guidelines set forth by the department.

The portable computing devices 116-1 to 116-3 and patient monitor 109 may communicate via wireless technologies that are configured for mutual authentication to establish a secure bi-directional communication channel therebetween. Some examples of secure bi-directional communication channel include Bluetooth or Wi-Fi, for example. In one embodiment, the portable computing device and patient monitor may be paired and/or pre-configured to enable immediate compatibility between the devices.

The portable computing devices 116-1 to 116-3 may also implement a web-based remote display to enable rescuers 104, 106 to communicate with remote personnel or a central facility to access, e.g., hospital patient record databases, or to communicate with other medical personnel who may be able to assist in treatment (nurses, doctors, dispatchers, to list a few examples). Likewise, the remote medical personnel may be able to view information displayed on the patient monitor 109 and/or portable computing device in real-time as well. The portable computing device may utilize wireless technologies such as Wi-Fi or wireless telephone networks (e.g., 3G/4G/5G wireless mobile telecommunication networks), or possibly even the Enhanced 911 (or E911) network. The Wi-Fi may connect via wireless networks that are typically secured that require password authentication to access the wireless network. This authentication may be a mutual authentication to establish secure a bi-directional communication channel between the devices.

In some embodiments, the portable computing devices 116-1 to 116-3 may be able to control the interface of the patient monitor 109 to cause the patient monitor to deliver some treatments to the patient (e.g., pacing) as well as set code events (e.g., delivery of shocks, administration of treatments, or administration of medications, etc.), and adjust information being displayed. For example, as the first rescuer 104 begins CPR, the second rescuer 106 or a third rescuer (not shown) may set up a bag-valve-mask (BVM) system or automatic ventilator to provide ventilations to the patient 102. Further, a capnography sensor may be implemented with the BVM or ventilator to measure end tidal carbon dioxide (ETCO2). Once implemented, the second rescuer 106 may utilize the second portable computing device 116-2 to adjust the display of the patient monitor 109 to show the ETCO2 information and/or display a prompt indicating when to ventilate the patient 102.

In the system 100 depicted in FIG. 1A, three portable computing devices 116-1 to 116-3 and two rescuers 104, 106 are depicted. However, in various embodiments, the number of portable computing devices 116, as well as the number of rescuers, may vary from one to more than three. Various rescuers may perform similar, different or partially overlapping roles. Rescuer roles may be coordinated or integrated as part of an overall rescue operation, for example. Each of the rescuers, or each of a subset of the rescuers, may use a different portable computing device 116. The type, hardware, software, functionality, sensors, accessories, applications or "apps", etc. of each particular portable computing device 116, as well as the patient monitor 109, may vary depending on a variety of factors. For example, such factors may include the hardware and software of or on the devices, the (actual or anticipated) role of a particular rescuer employing or anticipated to employ the device, the nature of the rescue operation or effort, the patient or type of patient, the environment, the setting, the vehicle type, or other factors. For example, in a multiple rescuer and multiple portable computing device 116 situation, each of various rescuers may play a different role related to, among other things, data collection, monitoring or storage, as well as patient treatment or rescue effort implementation, monitoring, supervision or control. For example, such roles may include the use of portable computing devices 116 with sensors, monitoring devices, accessories, particular software, "apps", etc.

In some embodiments, the system 100, or particular elements thereof, is configured such that wired or wireless data transfer, which data transfer can include two-way data communication and/or data storage at any of the various devices, is enabled and utilized between the patient monitor 109 and multiple portable computing devices 116, such as portable computing devices 116-1 to 116-3, as well as between various particular portable computing devices 116. The data transfer can include data transfer over one or more wired or wireless networks. As such, the patient monitor 109 may be configured to transfer data to or from one or more portable computing devices 116, and each of one or more portable computing devices 116 may be configured to transfer data to or from the patient monitor 109. Furthermore, each of multiple portable computing devices 116 may be configured to transfer data to or from each other. This data can include, for example, historical or current patient or rescue effort related data, status reports, alerts, and various other data. In some embodiments, the system 100 including the patient monitor 109 and each of multiple portable computing devices 116 may be configured to operate in an integrated and coordinated fashion, such as with regard to data transfer, data charging or energy draw.

In some embodiments, medical data, such as patient related data or rescue effort related data, can be stored not only at the patient monitor 109 but also at one or more of the portable computing devices 116. Depending on the particular system 100 and use, appropriate steps, including software and procedures used, can be taken to ensure user, rescuer or device identification, matching or authentication, as well as data protection, security, privacy, filtering, confidentiality, sanitization, etc. Obtained and transferred data can include data received or acquired in various ways, such as data input by a rescuer or user, data obtained from a remote source over one or more networks, data obtained from the patient such as via sensors or monitors, or data obtained from other devices of the system 100 such as may include the patient monitor 109 or one or more portable computing devices 116. Obtained or transferred data can also include data from peripherals, accessories, or software of the patient monitor 109 or the portable computing devices 116, such as data obtained or stored from a camera or laryngoscope, ultrasound transducer, pulse oximeter or oxygen saturation sensor, other physiological sensors, monitors, software or "apps", etc.

The patient monitor 109 in this example may be a defibrillator connected to the sensor housing 118 and may operate in a familiar manner (e.g., to provide defibrillating shocks to electrode pads integrated with the sensor housing 118 or placed separately on the patient 102). As such, the defibrillator may take a generally common form, and may be a professional style defibrillator, such as the R SERIES®, X SERIES®, M SERIES®, or E SERIES® defibrillator/monitors provided by ZOLL Medical Corporation of Chelmsford, Mass., or an automated external defibrillator (AED), including the AED PLUS® defibrillator, or AED PRO® defibrillator from ZOLL Medical Corporation.

A carrying case 110 may be mechanically attached to the patient monitor 109 and includes a plurality of pockets (e.g., zippered) on either side of the patient monitor for storing the portable computing device 116 and other medical supplies (e.g., medications, bandages, sensors, electrodes, resuscitative medical devices, etc.) that the rescuers 104, 106 may need during a rescue event. The carrying case 110 may further include a shoulder strap and/or handle (illustrated in FIGS. 8A-8D). In an alternative embodiment, the carrying case 110 may include multiple shoulders straps and be designed as a backpack-style carrying case. In yet another embodiment, the carrying case 110 may include wheels and a retractable handle to enable rolling of the carrying case 110 and patient monitor 109. In yet another embodiment, the carrying case could include additional pockets that are located on the top, bottom, or back of the patient monitor 109.

Figure 1B:
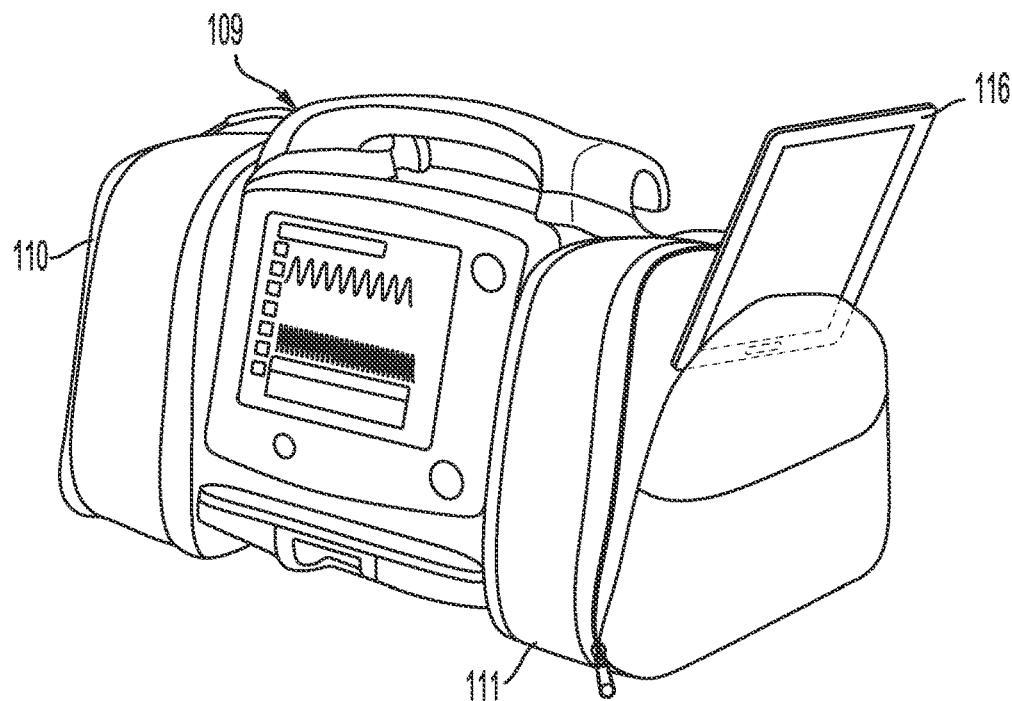
FIG. 1B is a schematic diagram illustrating an example of how a portable computing device may be placed in a pocket of the carrying case when not in use, in accordance with one embodiment.

FIG. 1B is a schematic diagram illustrating an example of how a portable computing device 116 (e.g., a tablet computer) may be stored in one of the pockets of the carrying case 110 when not in use. While the following examples may be described with respect to a single portable computing device, it is understood that a plurality of portable computing devices could be stored or implemented in various embodiments of the present disclosure. For example, additional portable computing devices may be stored in other pockets of the carrying case 110 or in a compartment of the patient monitor (as detailed, for example, in FIGS. 4A and 4B).

Typically, the carrying case 110 will include one or more pockets (e.g. 111) on either side of the patient monitor. The pockets of the carrying case 110 may further include one or more internal pockets, holders, or sleeves that may be dimensioned to fit the portable computing device 116 and secure the portable computing device within the sleeve. In general, many common consumer tablets have a substantially low profile, and have dimensions of approximately 9-11 inches in length, 6-8 inches in width, and approximately ¼ inches thick. The addition of a protective or ruggedized case would further increase these dimensions. Accordingly, the pocket 111 would need to be dimensioned to be able to accommodate the added dimensions. Additionally, the ruggedized case should be constructed of materials (typically non-metallic) capable of allowing the electromagnet fields to pass through with minimal, negligible, or zero interference in order to allow for efficient charging. Additionally, the thickness of any protective cases should be considered as the distance away from the wireless charging system can affect the charging efficiency. Thus, while added thickness may increase the safety to the device, it could affect the speed at which the device is able to recharge.

The carrying case 110 may be manufactured with protective materials (e.g., plastics and metals) that may be integrated into the carrying case to provide additional protection to the patient monitor 109 and portable computing device 116. For example, the materials may be water-resistant, temperature resistant, and drop-resistant, to withstand relatively extreme environments. Some examples of protective materials include polyurethane foams, neoprene coated fabrics, cross-linked polyethylene, and/or protective foam rubbers, to list a few examples. Additionally, while not shown in the figures, the portable computing devices 116-1 to 116-3, may be in protective cases that may be further designed to be water, drop, or temperature resistant.

Figure 1C:
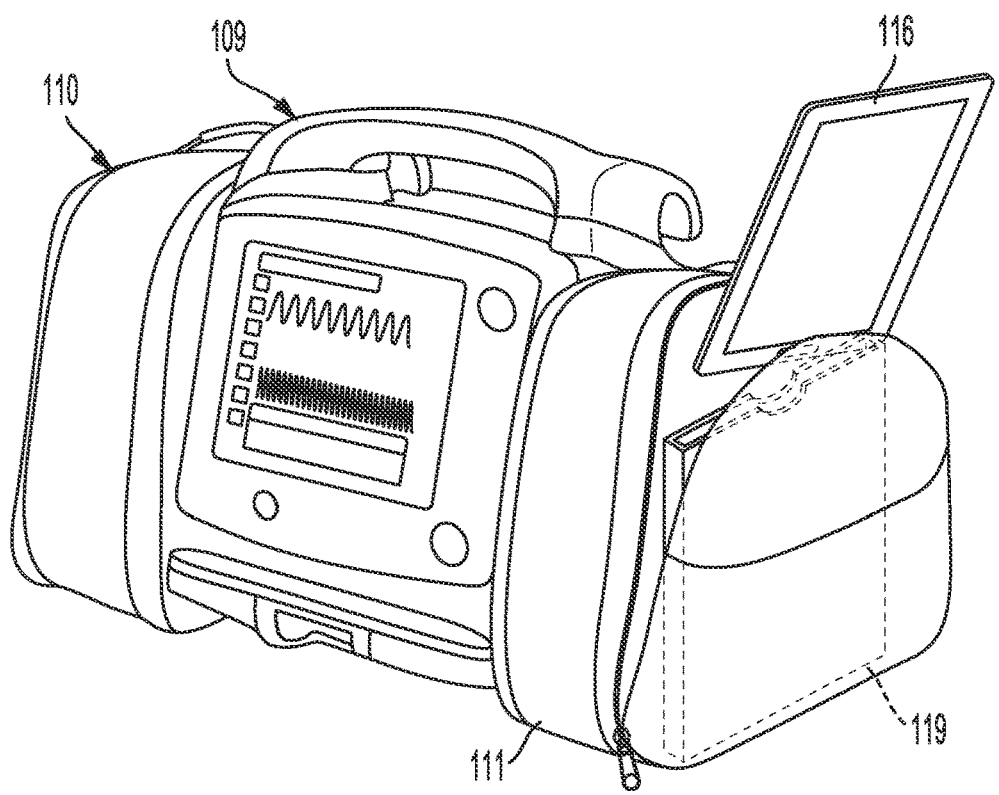
FIG. 1C is a schematic diagram illustrating an example of how the portable computing device may be placed within a receptacle of the carrying case.

FIG. 1C is a schematic diagram illustrating an example of how the portable computing device 116 may be stored within a compartment or receptacle 119 that may be provided in (e.g., mounted within, secured, or built into) one of the pockets 111 of the carrying case 110. The receptacle 119 is designed to both protect the portable computing device and also provide secure alignment of the portable computing device 116 with a wireless charging system (described below) so as to orient the portable computing device 116 into a charging position That is, once the portable computing device 116 is deposited into the receptacle 119, or another storage compartment, the portable computing device 116 is beneficially protected and is also conveniently positioned so that wireless charging coils are sufficiently aligned without requiring further re-positioning of the portable computing device.

While the illustrated example shows a receptacle 119, several other configurations may also be implemented as detailed below. For example, the portable computing device 116 may fit into a series of rails, a closable compartment, or a framework installed within the pockets of the carrying case 110. Accordingly, a user may simply insert, drop, or otherwise deposit the portable device into the space defined by the receptacle, thereby aligning the portable computing device 116 for subsequent charging thereof.

Figure 1D:
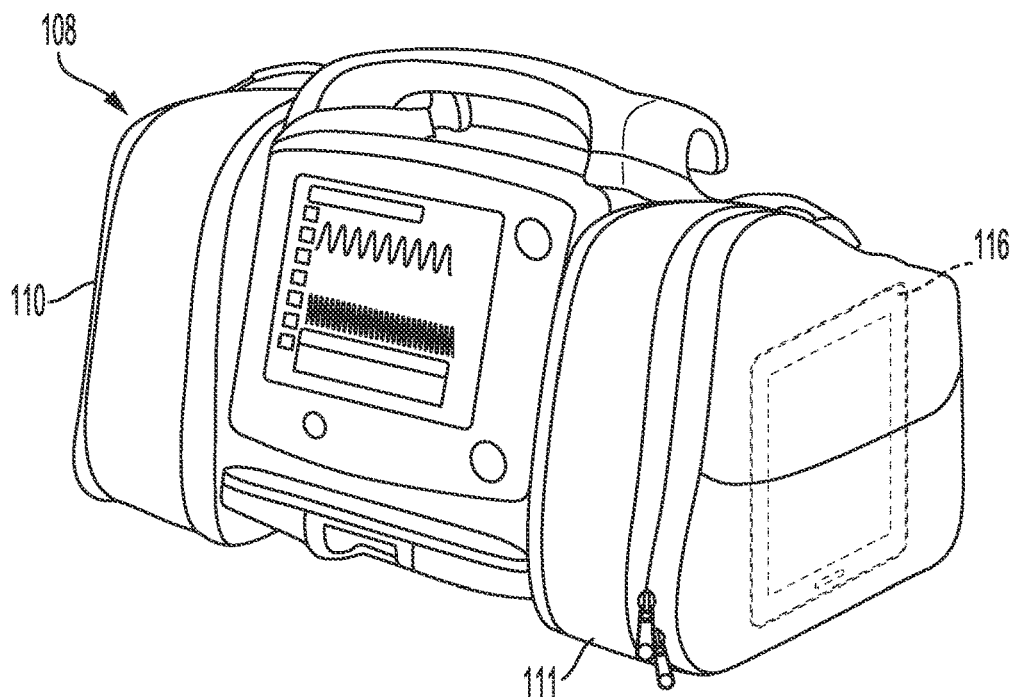
FIG. 1D is a schematic diagram illustrating the portable computing device positioned in a pocket of the carrying case, in accordance with one embodiment.

FIG. 1D is a schematic diagram illustrating the portable computing device 116 stored in the pocket 111 of the carrying case 110. In this embodiment, the portable computing device 116 is simply placed into the pocket 111 whenever the device is not in use and/or needs to be charged. In this implementation, the wireless charging system 112 (not shown) will be designed and/or configured such that the portable computing device 116 can be charged regardless of position and orientation. For example, the wireless charging system 112 will include various coil sizes, which are arranged in various orientations. Likewise, there may be coils placed in multiple sides of the pocket 111 (e.g., top, bottom, left, right, etc.) such that regardless of position and orientation the portable computing device 116 will be sufficiently aligned to enable wireless charging.

Figure 1E:
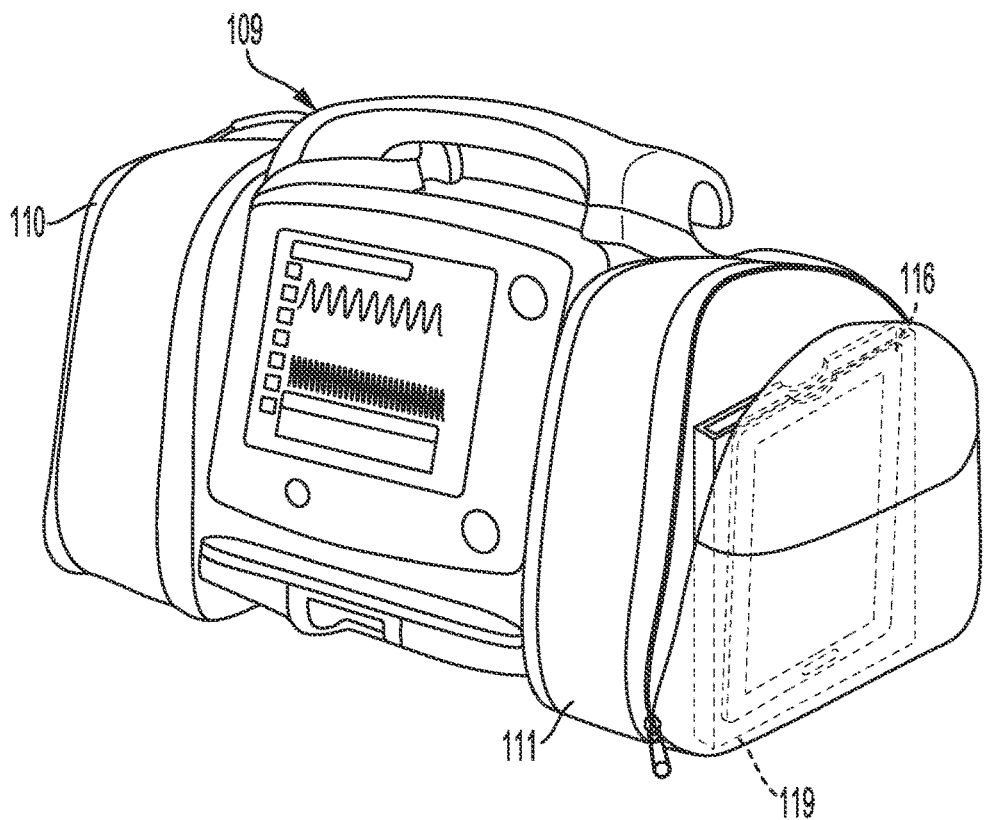
FIG. 1E is a schematic diagram illustrating the portable computing device positioned in the receptacle mounted within the pocket of the carrying case, in accordance with one embodiment.

FIG. 1E is a schematic diagram illustrating the portable computing device 116 positioned in the receptacle 119, which is mounted within the pocket 111 of the carrying case 110, in accordance with another embodiment. In this embodiment, the portable computing device may be held in an appropriate position where the pocket and/or receptacle provide a protective covering from the outside environment, supplies and devices of the pocket 111, and/or mechanical stimuli (e.g., dropping, banging) that would otherwise damage the portable computing device. The portable computing device 116 may also be held in position by the receptacle so as to allow for suitable alignment with transmission coils of the wireless charging system 112 and, hence, automatic charging thereof. That is, once the portable computing device 116 is deposited into the receptacle 119, the portable computing device 116 is protected and positioned so that the transmission coils 114 of the wireless charging system 112 are sufficiently aligned with the receiver coils 117 of the portable computing device 116 such that further re-positioning of the portable computing device is not required and charging of the portable computing device 116 may automatically begin.

Figure 1F:
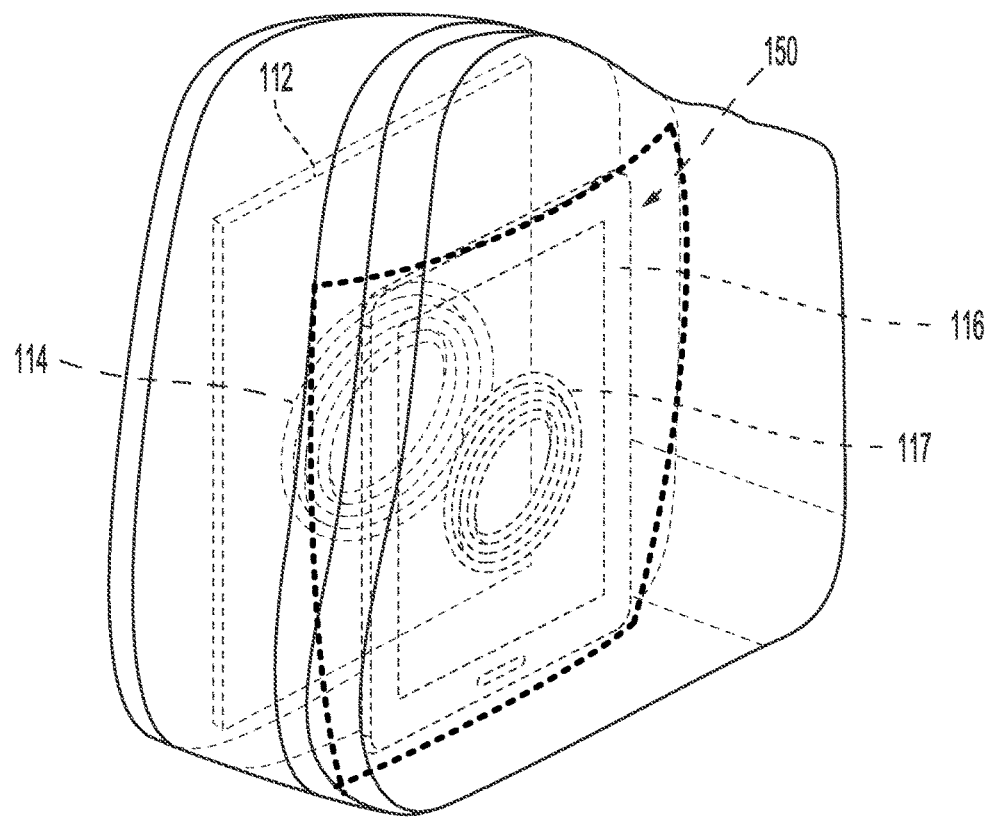
FIG. 1F is a schematic diagram illustrating a pocket of the carrying case that may include an internal pocket (or sleeve) for storing and securing the portable computing device when the device is not in use.

FIG. 1F is a schematic diagram illustrating the pocket 111 of the carrying case 110 that includes an internal pocket (or sleeve) 150 for storing and securing the portable computing device 116 when the device is not in use and/or needs to be recharged, for example. As illustrated, the sleeve 150 is dimensioned to secure the portable computing device 116 within the pocket and hold the device in an appropriate position where the internal pocket 150 provides some additional protective covering from the outside environment and/or other supplies contained within the pocket 111. The pocket may be manufactured with protective materials including polyurethane foams, neoprene coated fabrics, cross-linked polyethylene, and/or protective foam rubbers, to list a few examples. The internal pocket 150 may also provide suitable alignment of the transmission coils 114 of the wireless charging system 112, and the receiver coils 117 of the portable computing device. As before, once the portable computing device 116 is deposited into the internal pocket 150, the portable computing device 116 is positioned so that the transmission coils 114 of the wireless charging system 112 are sufficiently aligned with the receiver coils 117 of the portable computing device 116 such that charging of the portable computing device 116 may automatically begin.

While not illustrated in the figures, the portable computing device 116 may be a "ruggedized" version of the device. A ruggedized version is a device that is designed and manufactured to be able to withstand harsher environments and situations than a typical consumer device. Often, devices are encased in a water-tight, shockproof case. Additionally, the internal components may be designed and configured with withstand high heat, shocks/vibrations, drops, moisture and water, fire, and other harsh environments. Accordingly, the protective case may add size or bulk (e.g., height, thickness, length, and weight) to the device. As such, the pocket 111 and internal pocket 150 may be manufactured in different sizes to accommodate different device sizes. Alternatively, the internal pocket 150 may be suitable elastic and capable of expanding and constricting to accommodate devices of varying size.

Figure 1G:
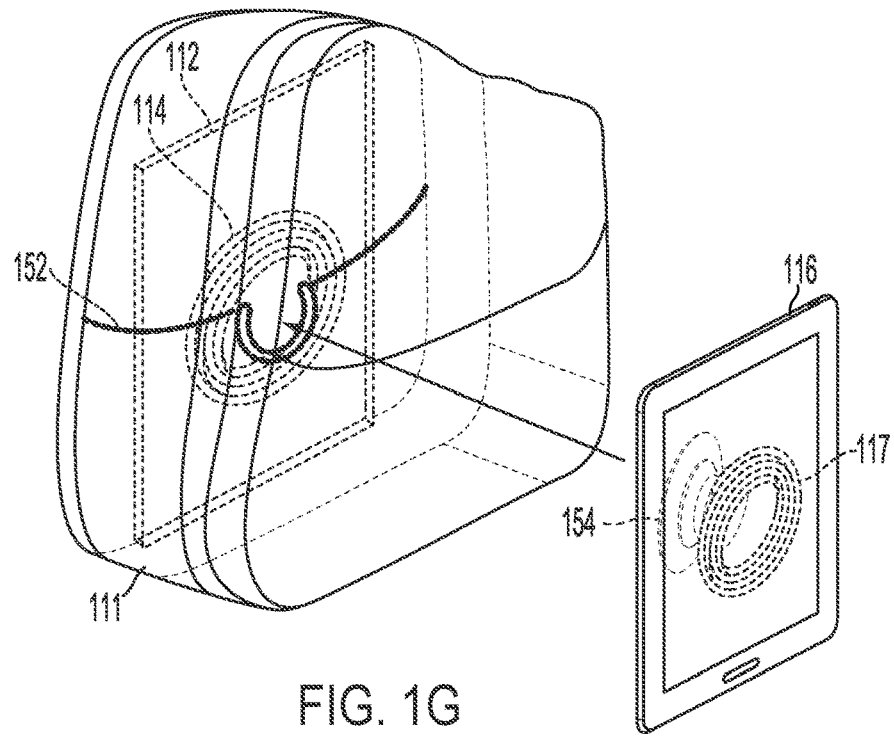
FIG. 1G is a schematic diagram illustrating the pocket of the carrying case that may include a mounting bracket (or holder) for securing a portable computing device and a retractable holder.

FIG. 1G is a schematic diagram illustrating the pocket 111 of the carrying case 110 that includes a mounting bracket (or holder) 152 for securing a portable computing device 116 and a retractable holder 154. As illustrated, the retractable holder 154 is generally conical in shape and tapered such that the narrow end of the cone-shape may be affixed or otherwise securely coupled with the portable computing device 116. The pocket 111 includes the mount 152 that may be configured to secure the retractable holder 154 to the mount 152. The shape of the retractable holder 154 and the mount 152 enables the retractable holder 154 to securely fit between a back wall of the pocket and the opening of the mount. It can be appreciated that the retractable holder 154 may be constructed to have other shapes that would enable the holder and the mount to provide a relatively secured coupling between the portable computing device and the holder.

Additionally, for various embodiments, the pocket 111 (or patient monitor) may comprise a wireless charging system 112. The transmission coil 114 of the wireless charging system 112 in the illustrated example could be aligned (e.g., centered) to the opening of the mount 152. Accordingly, when the portable computing device 116 is placed within mount 152, the receiver coils 117 of the portable computing device 116 will be substantially aligned with the transmission coils 114 of the wireless charging system 112 to enable wireless charging.

Figure 1H:
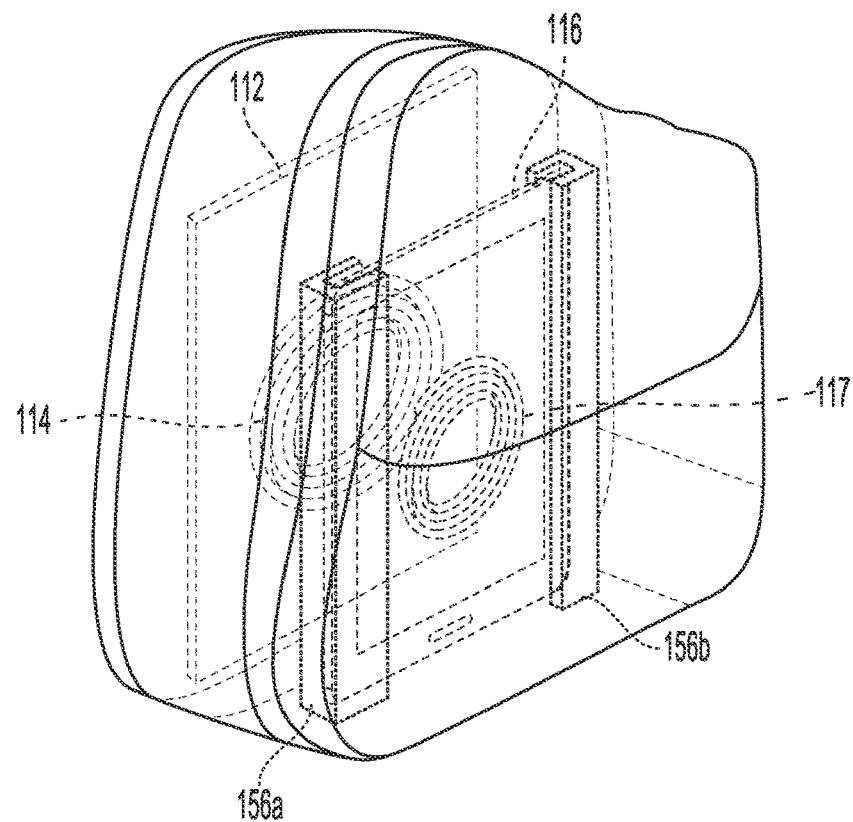
FIG. 1H is a schematic diagram illustrating the pocket of the carrying case that may include a series of guide rails (or frame rails) for securing the portable computing device within the pocket of the carrying case.

FIG. 1H is a schematic diagram illustrating the pocket 111 of the carrying case 110 that includes a series of guide rails (or frame rails) 156a, 156b for securing the portable computing device 116 within the pocket 111 of the carrying case 110. The guide rails 156a, 156b are designed to provide secure alignment of the portable computing device 116 with the wireless charging system 112 and to orient the portable computing device 116 into an appropriate charging position. That is, once the portable computing device 116 is placed into or otherwise coupled with the guide rails 156a, 156b and slides far enough along the rails, the portable computing device 116 will be substantially aligned so that wireless transmission coils 114 are sufficiently aligned with the receiver coils 117. In embodiments with ruggedized devices, the guide rails may be dimensioned to fit ruggedized portable computing device.

Figure 1I:
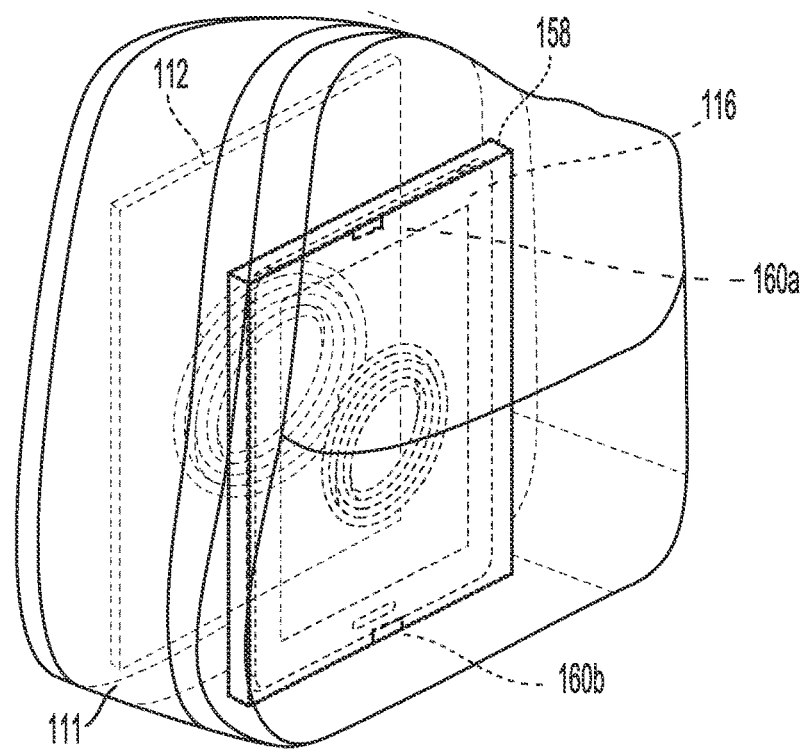
FIG. 1I is a schematic diagram illustrating the pocket of the carrying case that may include a mechanical receiving frame, which may include a plurality of snaps, holders, buttons, or similar fasteners to mechanically secure the portable computing device to the receiving frame within the pocket of the carrying case.

FIG. 1I is a schematic diagram illustrating the pocket 111 of the carrying case 110 that includes a receiving frame 158, which includes a plurality of mechanical fasteners 160a, 160b (e.g., snaps, holders, buttons, or similar fasteners) to mechanically secure the portable computing device 116 to the receiving frame 158 within the pocket 111 of the carrying case 110. Similar to previous embodiments, the receiving frame 158 is designed to protect the portable computing device 116 and provide suitable alignment of the portable computing device 116 with the wireless charging system 112 to enable wireless charging.

Figure 1J:
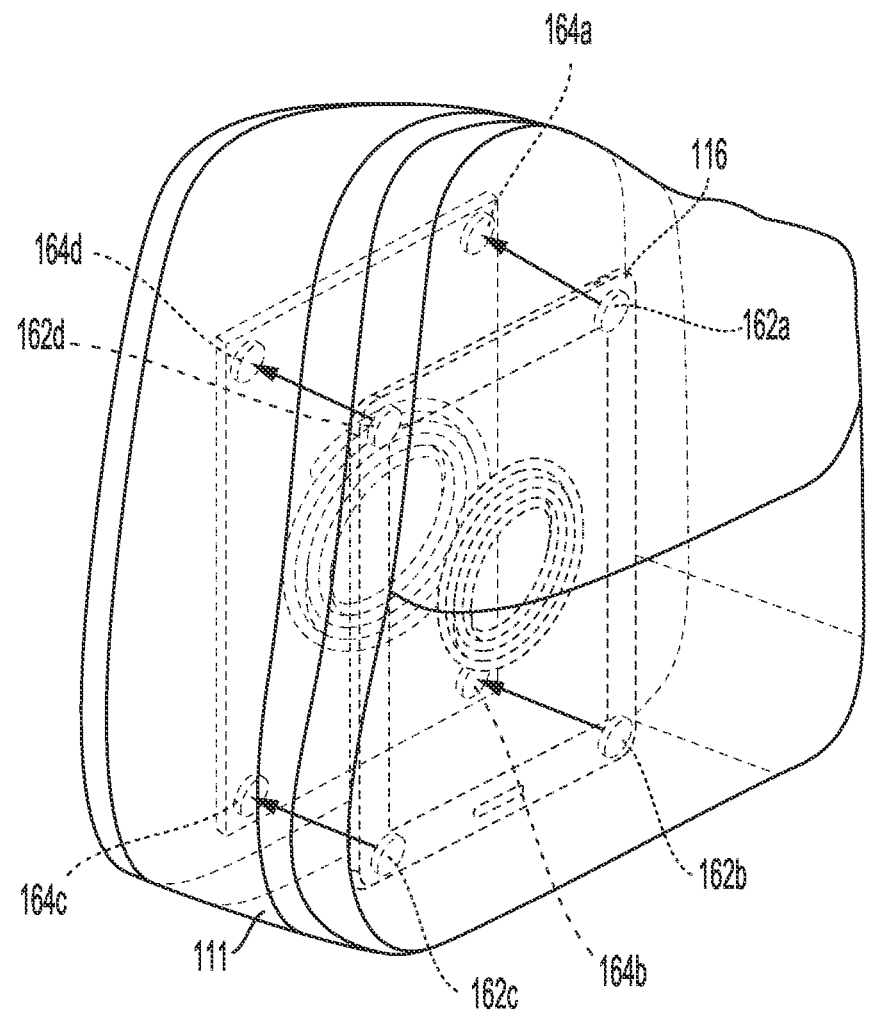
FIG. 1J is a schematic diagram illustrating an embodiment in which the portable computing device may include a plurality of magnets disposed in, or on, the device.

FIG. 1J is a schematic diagram illustrating an embodiment in which the portable computing device 116 includes a plurality of magnets 162a-d disposed in (or on) the portable computing device 116. Similarly, the wireless charging system 112 also includes a plurality of corresponding magnets 164*a-d* that are positioned about the wireless charging system 112 such that when the portable computing device 116 is placed within proximity to the wireless charging system 112 the pluralities of magnets will attract to its corresponding magnets and cause the portable computing device 116 to be secured to, and align with, the wireless charging system 112. As before, once the portable computing device 116 is properly aligned with the wireless charging system 112, then wireless charging will automatically begin.

Additionally, various combinations of these embodiments may be implemented in conjunction. For example, the receptacle 119 or guide rails 156*a*, 156*b* described in FIGS. 1E and 1H, respectively, could also include magnets further secure or align the when the portable computing device 116. Likewise, the guide rails 156*a*, 156*b* could be used in combination with the mount 152 and holder 154.

Figure 1K:
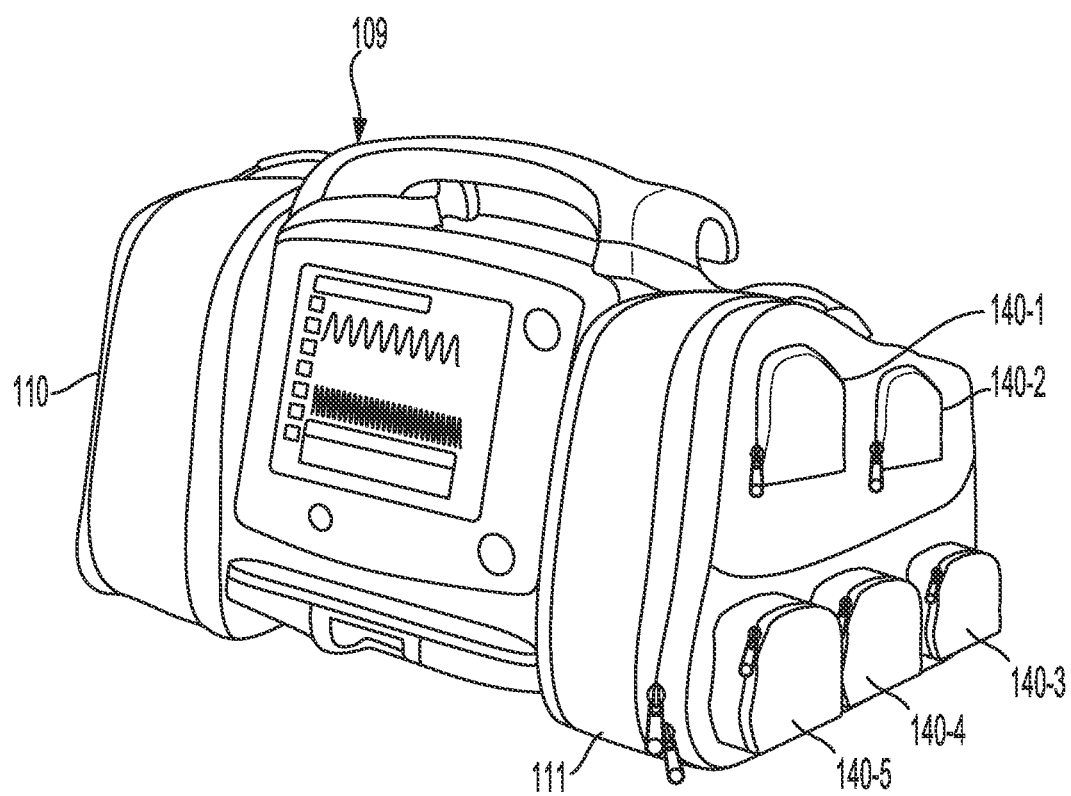
FIG. 1K is a schematic diagram illustrating additional pockets that have been integrated into the carrying case, in accordance with one embodiment.

FIG. 1K is a schematic diagram illustrating accessory pockets 140-1 to 140-5 of the carrying case 110, according to one embodiment. In the illustrated embodiment, the accessory pockets 140-1 to 140-5 may have varying dimensions such that each pocket is generally sized to fit a particular device (e.g., portable computing device, a wireless sensor, a smartphone, personal digital assistant, a pager, or a smartwatch, for example). As illustrated, some pockets are deeper than others to account for the varying sizes of the different devices (e.g., a wireless sensor may be thicker than a smartphone, and therefore, needs a deeper pocket). By customizing the size of each pocket, the devices stored within each pocket can be secured and protected. While not expressly illustrated in the figures, the pockets may be padded or include protective materials interwoven into the pockets to further protect the devices stored within the pockets. In some embodiments, each of the pockets 140-1 to 140-5 may be configured to enable or facilitate wired or wireless charging of an inserted device, such as a portable computing device 116 or other accessory-type device such as a sensor (e.g., ultrasound probe, video laryngoscope) that can be used in conjunction with the portable computing device 116. In some embodiments, the carrying case 110 (or another component or components of the system 100) may include one or more wireless charging systems 112 including transmission coils 114. Furthermore, each wireless charging system 112 or transmission coil 114 may be used to provide wireless charging to one or several devices, each inserted into one of the pockets 140-1 to 140-5.

Figure 1L:
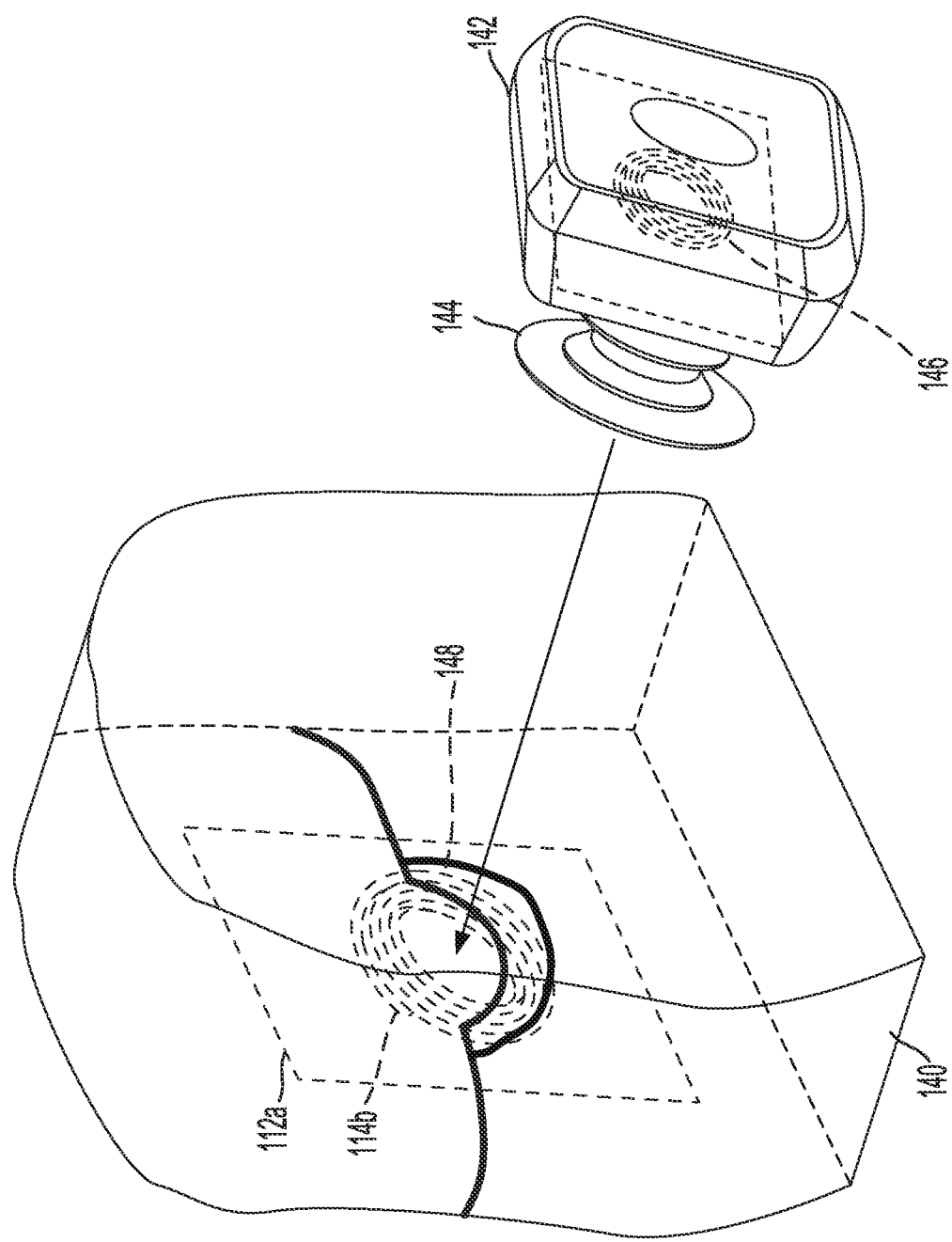
FIG. 1L is a schematic diagram illustrating a pocket with a mount for securing a wireless sensor with receiving coils and a retractable holder, in accordance with one embodiment.

FIG. 1L is a schematic diagram illustrating an accessory pocket 140-1 (with the front opening and zippers removed for clarity) with a mounting bracket (or holder) 148 for securing a wireless sensor 142 or other device (e.g., portable computing device) with receiver coils 146 and a retractable holder 144.

As illustrated, the retractable holder 144 may be generally conical in shape and tapered such that the narrow end of the cone-shape may be affixed or otherwise securely coupled with the wireless sensor 142. The accessory pocket 140-1 includes a mount 148 that may be configured to enable the retractable holder 144 to be secured to the mount 148. The shape of the retractable holder 144 and the mount 148 enables the retractable holder 144 to securely fit between a back wall of the pocket and the opening of the mount. It can be appreciated that the retractable holder 144 may be constructed to have other shapes that would enable the holder and the mount to provide a relatively secured coupling between the sensor and the holder.

As one example of charging mechanisms, the back wall of each of the accessory pocket 140-1 to 140-5 may comprise integrated wireless charging systems, which each include transmission coils. The transmission coil 114*b* of the wireless charging system 112*b* in the illustrated example could be aligned (e.g., centered) to the opening of the mount 148. Accordingly, when placed within mount 148, the receiver coils 146 of the wireless sensor 142 will be aligned with the transmission coils 114*z* of the wireless charging system 112*b*, so as to establish a suitable wireless charging coupling.

While the illustrated embodiment may be directed to an embodiment that utilizes a retractable holder 144 and corresponding mount 148, other methods for securing and aligning the wireless sensor 142 may be implemented. For example, the wireless sensor 142 may fit within an internal pouch or sleeve installed within the pocket 140-1. Alternatively, magnets installed within the sensor 142 and pocket 140-1 could be used to secure and/or align the wireless sensor and transmission coils 114*b*.

In some implementations, a charge level of the wireless devices could be obtained. The charge level information could then be accessed and/or displayed by the portable computing devices 116-1 to 116-3 and/or patient monitor 109. Similarly, an indicator (e.g., an icon) may be displayed to indicate that one or more of the devices is not charging. This would serve the dual purpose of providing an indication that the devices accessories are detected (i.e., present) and charging.

Additionally, indicator lights, for example, could be installed outside of the carrying case 110. These indicator lights would indicate which devices were present and charging. The indicators could be labeled or assigned numbers corresponding to specific pockets, and only the lights associated with present devices are illuminated. The wireless devices may further include a Bluetooth or GPS tracker that helps rescuers locate missing devices. For example, an alarm or prompt could be provided in the event that rescuers have moved a specified distance (e.g., 100 yards) from a device. Alternatively, the location information could be transmitted to the patient monitor 109 portable computing devices. This would provide information about the last known locations of the sensors. Thus, enabling the rescuers to return to find lost/missing devices.

Figure 2A:
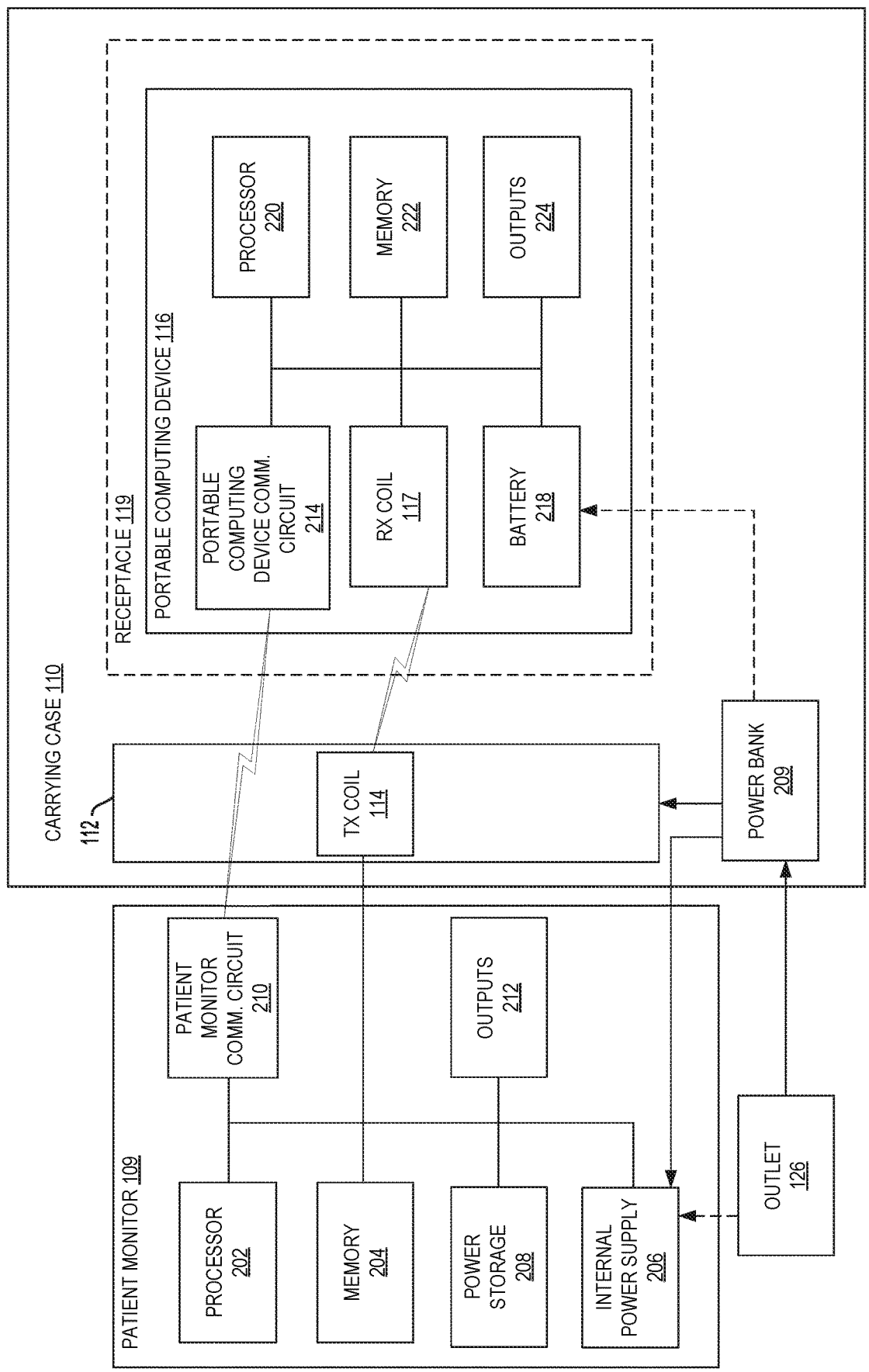
FIG. 2A illustrates an example in which a wireless charging system and transmission coil(s) and associated circuitry are located in the carry bag, according to one embodiment.

FIG. 2A is a block diagram illustrating exemplary components of the patient monitor 109 and the portable computing device 116. In the illustrated example, the wireless charging system 112 and transmission coils 114 are external to, and a separate component from, the patient monitor 109, and integrated into the carrying case 110. In some embodiments, the wireless charging system 112 and the patient monitor 109 may be connected, for example, via a cable or wireless connection in which power may be transferred from the patient monitor 109 to the wireless charging system 112. Hence, the wireless charging system 112 may be able to draw power from the patient monitor 109, such as when the patient monitor 109 is plugged in, for example. In other embodiments, rather than utilizing an internal power supply 206 that is part of the patient monitor 109, a power supply may instead be utilized, for the patient monitor 109 or other system components, which power supply is separate/external from the patient monitor 109, but connected to the patient monitor 109 or other components via wired or wireless coupling, for instance. In some embodiments, a power supply used for the patient monitor 109 may be connected to and powered by a power source that is separate from the patient monitor 109, such as the outlet 126.

Furthermore, in some embodiments, the wireless charging system 112 may be able to be powered on its own. For example, the wireless charging system 112 may have its own power cord or source independent of the patient monitor 109. For instance, the wireless charging system 112 may be connected to power bank 209, such as a battery, which may be located in the carrying case 110, as depicted, or elsewhere. In some embodiments, the wireless charging system 112 may draw power from the outlet 126 and may also enable energy to pass through the power bank 209 to other components of the system, for example.

While, in the embodiment depicted in FIG. 2A, the wireless charging system 112 and transmission coils 114 are in the carrying case 110, in other embodiments, those components, in whole or in part, may be part of the patient monitor 109, for example.

The patient monitor 109 includes a processor 202 for executing instructions of software running on the patient monitor 109, memory 204 to store information (e.g., software, signals received from the sensors of the sensor housing 118, and/or information received from the portable computing device 116, to list a few examples). The processor 202 further receives and processes input signals from one or sensors. The processor also generates physiological data based on the input signals from the one or more sensors and control transmission of generated physiological data to a portable computing device 116. The patient monitor 109 may further include outputs 212 (e.g., display screen and/or speakers) to provide feedback, physiological information, patient data, or other relevant information to the rescuers 104, 106. The display may be a touchscreen display, which is a combined input/output device, that enables users (e.g., rescuers or caregivers) to interact with the patient monitor 109 by touching the display screen.

The internal power supply 206 converts energy from an external power source (e.g., outlet 126, grid power, power bank) to a regulated DC (direct current) power for the various circuits and components of the patient monitor 109. In one example, the internal power supply 206 receives power directly from a power outlet 126. In another example, the internal power supply receives power from a power bank 209 integrated into, or located within, the carrying case 110. The power bank 209 may be a storage device (e.g., battery) that provides energy to power the patient monitor 109, portable computing device 116, and/or wireless charging system 112. In one example, the power bank 209 may have a capacity as much as 8-10 amp hours. However, the capacity and weight of the power bank, as well as the available space within the carrying case 110 may also factor into the capacity of the power bank 209.

In the event that the patient monitor 109 is disconnected from the external power source (e.g., unplugged from outlet 126), the internal power supply 206 may begin to draw power from the power bank 209. This provides additional runtime for the patient monitor 109, wireless charging system 112, and the portable computing device. In some embodiments, an optional cable may connect the power bank 209 to the portable computing device 116.

The internal power supply 206 further distributes the power to the power storage device 208 (e.g., batteries and/or capacitors). The power storage device stores energy to further enable the patient monitor 109 and wireless charging system 112 to operate for extended periods of time when not plugged into an external power source. As detailed below, the internal power supply 206 may also provide power to the wireless charging system 112 when the patient monitor 109 is plugged into the outlet 126, even when the patient monitor is not powered on. In general, the power storage device should be large enough in capacity to operate the patient monitor for 8-10 hours, which includes having sufficient charge to provide repeated therapeutic shocks to the patient, as needed.

As described in later figures, the internal power supply 206 may provide power to the transmission coils 114 and corresponding circuitry, which may include a transformer of the wireless charging system 112, to enable wireless transmission of energy to charge portable computing devices, wireless sensors, and other computing devices (e.g., smartphones, smartwatches, and personal digital assistants).

The patient monitor 109 also includes a communication circuit 210, which enables wireless communication with the portable computing device 116. The information transferred between the devices could be any appropriate data that would be beneficial for the user of the portable computing device to access. Such information may include, for example, patient information (patient gender, age, height, weight), measured physiological information (e.g., heart rate, blood pressure, $CO_2$ waveforms, ECG waveforms, SpO2 data), CPR feedback information (e.g., CPR rate, CPR depth, CPR force, CPR acceleration, and release velocity), status information (e.g., self-test results, power/charge level, functional capabilities, sensors available), recommended protocols (e.g., for chest compressions, ventilations, respiratory distress, traumatic brain injury, etc.), amongst other information that may be relevant to the rescue effort.

The portable computing device 116 also includes a processor 220, memory 222, and outputs 224. Similar to the patient monitor 109, the processor 220 is for executing instructions of software running on the portable computing device, the memory 222 stores software and/or information received from the patient monitor 109. The portable computing device 116 may also include an output 224 (e.g., display 115 and/or speakers) to display information to rescuers. As with the patient monitor 109, the display 115 may be touchscreen display to enable intuitive user interaction of the portable computing device 116. This touchscreen device provides an input to, for example, allow the rescuers 104, 106 to enter patient information (e.g., height, weight, age, and gender) via the touchscreen display, or provide other commands to the device. For example, the rescuers may provide control aspects of the patient monitor such as commands for configuring displays and features of the patient monitor, accessing diagnostic or therapeutic controls, or viewing event logs, to list a few examples. The portable computing device 116 may also include internet connectivity (e.g., via Wi-Fi or 3G/4G wireless mobile telecommunication networks) to enable the rescuer to communicate with a central facility, emergency dispatch, or medical personnel in a hospital, for example.

The portable computing device 116 may further independently connect to one or more sensors or peripheral devices (e.g., wireless pulse oximeter sensor, wireless blood pressure sensors, wireless capnography sensors, and ultrasonic transducers, to list a few examples). By directly connecting peripheral devices to the portable computing device 116, portions of the processing and analysis of measured information can be managed by the portable computing device 116. This reduces the amount of processing and analysis that would otherwise need to be performed by the patient monitor 109, and additionally may even reduce the amount of information that needs to be displayed on the patient monitor. Additionally, an embodiment in which multiple portable computing devices 116-1 to 116-3 are implemented, each rescuer and their corresponding portable computing device may be assigned a specific role in the rescue effort (e.g., CPR, ventilation/respiratory, medication, and trauma). Likewise, each device may communicate directly with one or more sensors related to their assigned role in the rescue effort and each portable computing device may perform the analysis of the information received. Then, each portable computing device, may then distribute the collected and analyzed information to the other portable computing devices and/or patient monitor.

Figure 2B:
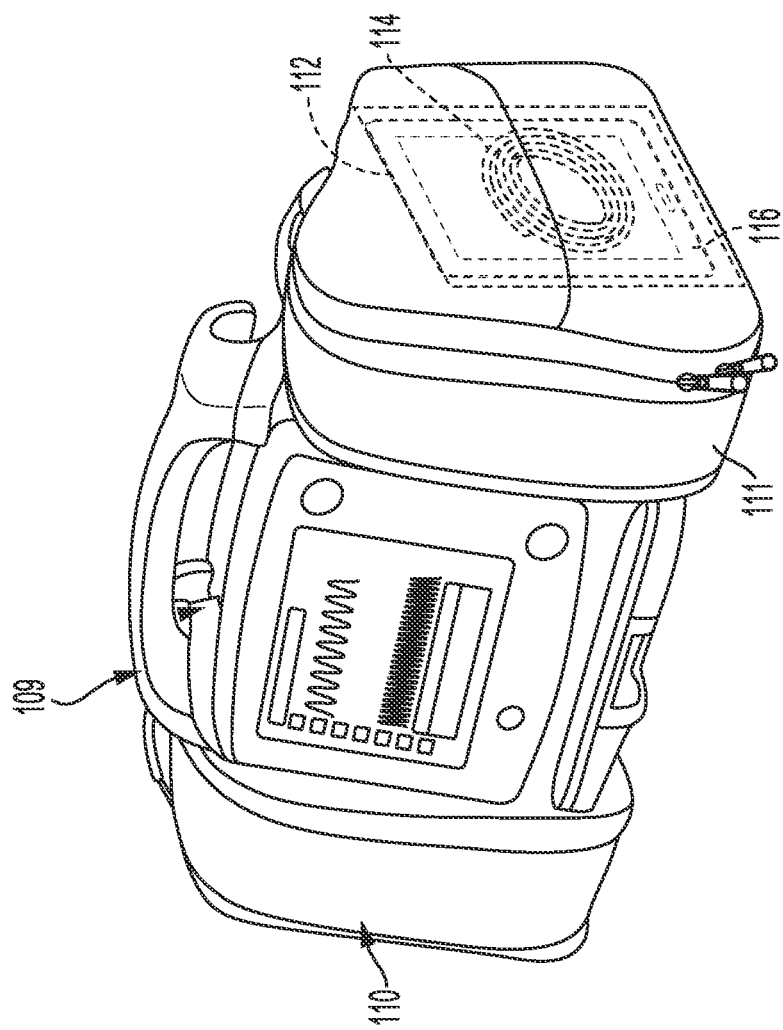
FIG. 2B is a schematic diagram illustrating the portable computing device inside of a pocket of the carrying case and being located in proximity to the wirelessly charging pad and transmission coil(s).

FIG. 2B is an exemplary schematic diagram illustrating the portable computing device 116 placed securely inside of a zippered pocket of the carrying case 110 and being located in proximity to, and in alignment with, the wireless charging system 112 and transmission coil 114. An advantage of this configuration is that the portable computing device 116 can begin automatically charging whenever it is in proximity to, and in alignment with, the wireless charging system 112 (e.g., typically in the range of 0.1 centimeters to 10 centimeters). In some examples, proximity is detected by the wireless charging system 112 delivering low duty cycle energy pulses (e.g. <20%, <10%, <5%, <1%, <0.1%) at a rate of 0.1-5 pulses per second, in order to minimize energy consumption. Proximity may be detected when communications are established with the portable computing device 116. A benefit of this implementation is that the configuration does not require the rescuers to remember, or even use, charging cables and adapters or physical interfaces that would otherwise be needed in order to begin charging of the portable computing device 116. Likewise, the rescuers do not need to remember to plug in the device because the portable computing device 116 will automatically begin charging when suitably placed within the carrying case 110 such that the portable computing device is in proximity to the wireless charging system 112 and aligned with the wireless charging system 112.

Figure 2C:
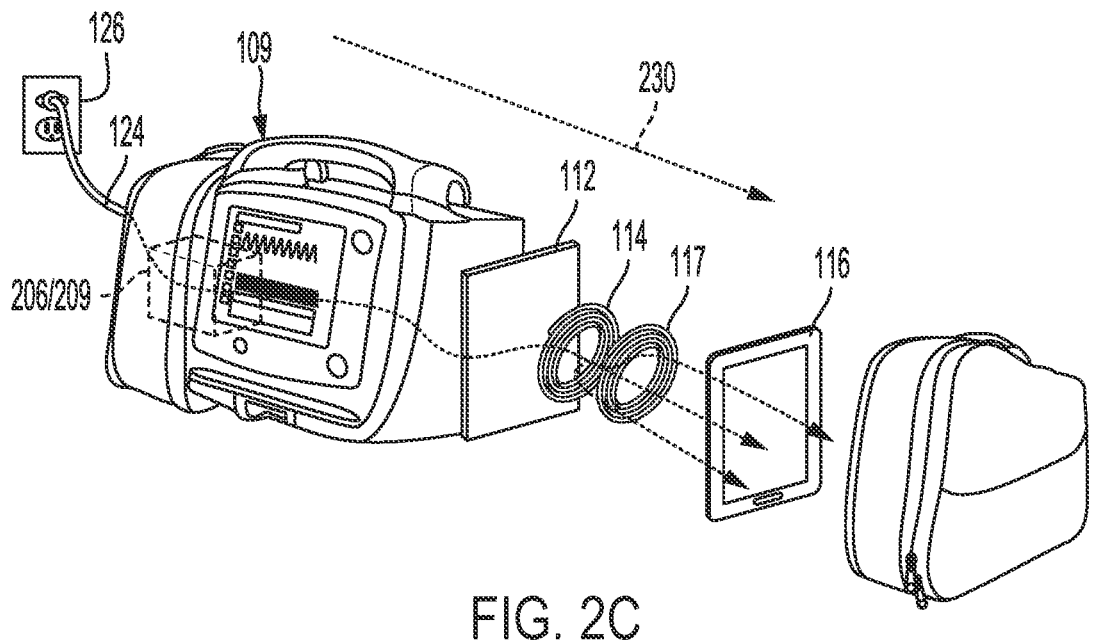
FIG. 2C is an exploded view further illustrating the flow of energy (e.g., electricity) from the outlet, through the patient monitor, and to the portable computing device, according to one embodiment.

FIG. 2C is an exploded view illustrating the flow of energy (e.g., electricity) from an external power source (e.g., outlet 126) to the portable computing device 116. The direction of the flow of energy is shown by arrow 230.

Energy flows from an external power source such as an outlet 126 via a cord 124 to the power bank 209 and/or internal power supply 206. The energy can be used to power charge the power bank 209, charge the power storage device 208, operate the patient monitor 109, and power the wireless charging system 112.

The energy flows from the outlet 126 to the wireless charging system 112 and its transmission coil 114, which are located within a pocket of the carrying case 110 in this embodiment. The transmission coils of the wireless charging system 112 generate an electromagnetic field (detailed in FIG. 5A) to wirelessly transfer energy to the receiver coil 117 (and associated circuitry, which may include a transformer for converting the received electromagnetic flux from the at least one receiving induction coil to energy for charging the battery) within the portable computing device 116. The received energy can be used to power the portable computing device 116 as well as charge the battery 218 of the portable computing device 116.

Figure 2D:
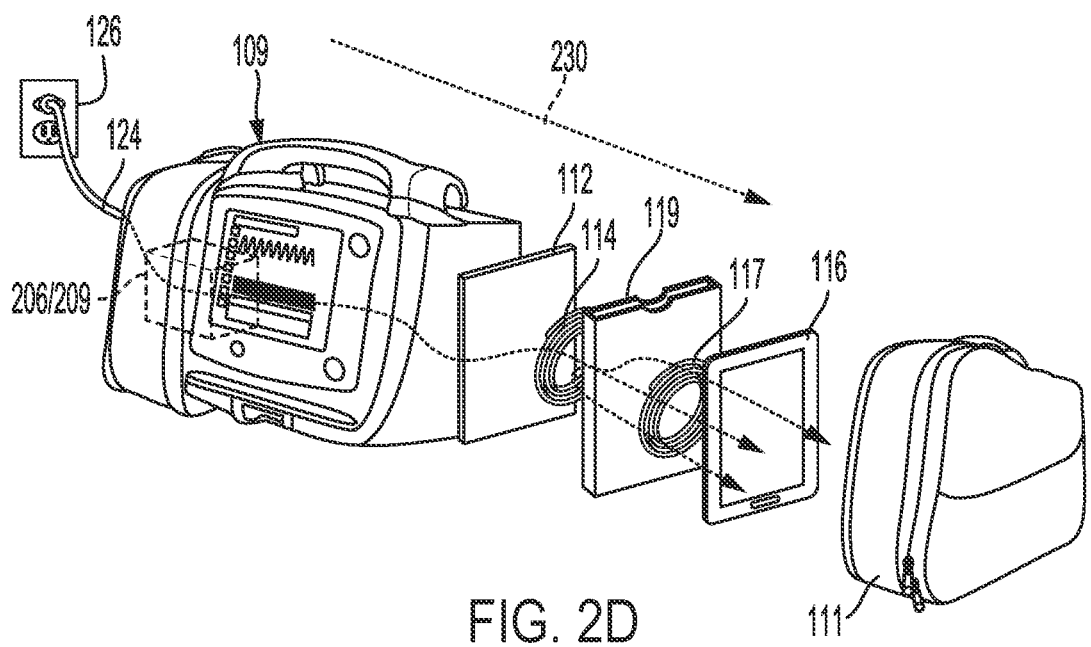
FIG. 2D is an exploded view illustrating an alternative embodiment that may include a frame, sleeve, or receptacle for storing tablet within a pocket of the carry case, according to one embodiment.

FIG. 2D illustrates an alternative exploded view, which also illustrates the flow of energy from an external power source (e.g., the outlet 126) to the portable computing device 116. FIG. 2D is similar to FIG. 2C; however, this embodiment illustrates the receptacle 119, which may be installed within the carrying case 110. As detailed previously, this receptacle 119 provides an additional protective compartment or housing for the portable computing device 116 (e.g., more than that of the pocket(s) of the carry case) 111 and also helps to align the portable computing device 116 with the wireless charging system 116. Such improved alignment may increase the overall efficiency of the wireless energy transfer from the wireless charging system 112 to the portable computing device 116. For example, the power transfer between the transmission coils 114 of the wireless charging system 112 and the receiver coils 117 of the portable computing device 116 may be substantially increased or otherwise improved when the corresponding coils are in close proximity to one another and in alignment than would otherwise be the case without a mechanical component to maintain physical proximity and alignment of the corresponding coils 114, 117.

While the illustrated embodiment shows a rigid, pocket-like receptacle, alternative embodiments may implement a frame, series of rails, detent, or other locking fasteners, or a sleeve manufactured into the interior of the carrying case 110. The receptacle 119 may further include a cover and/or locking mechanism to further secure the portable computing device within the receptacle 119. In general, the purpose of these receptacles and receptacle-like components is to secure, store, and/or protect the portable computing device 116 in the carrying case 110. Moreover, these features aid in the alignment of the transmission coils 114 to cause a more efficient transfer of energy to the receiver coils 117 of the portable computing device 116.

FIGS. 3A-3D illustrate alternative examples of the present system according to an embodiment. While broadly similar to the examples described in FIGS. 2A-2D, in this embodiment, the transmission coils 114 and wireless charging system 112 may be located within the patient monitor 109 (e.g., provided as hardware components of the patient monitor 109). The transmission coil 114 could be affixed to an interior wall of the patient monitor 109 or integrated into the walls (e.g., front, sides, bottom, or top) of the patient monitor 109. Alternatively, the transmission coil 114 may possibly be located on the outer surface of the patient monitor 109. Again, the coils could be located on the front, sides, bottom, or top walls. As detailed in FIG. 3B, when installing the wireless charging system 112 and/or transmission coils 114 within the patient monitor 109, it may be preferable for the portable computing device 116 to be held in closer proximity to the patient monitor, so that the portable computing device and the wireless charging system are in proper proximity and alignment. Consequently, the carrying case 110 in this embodiment may be constructed so that the position of the portable computing device 116 is within an appropriate pocket of the carrying case 110 suitable for charging (e.g., depending on the location of the wireless charging system and/or transmission coil 114).

Figure 3A:
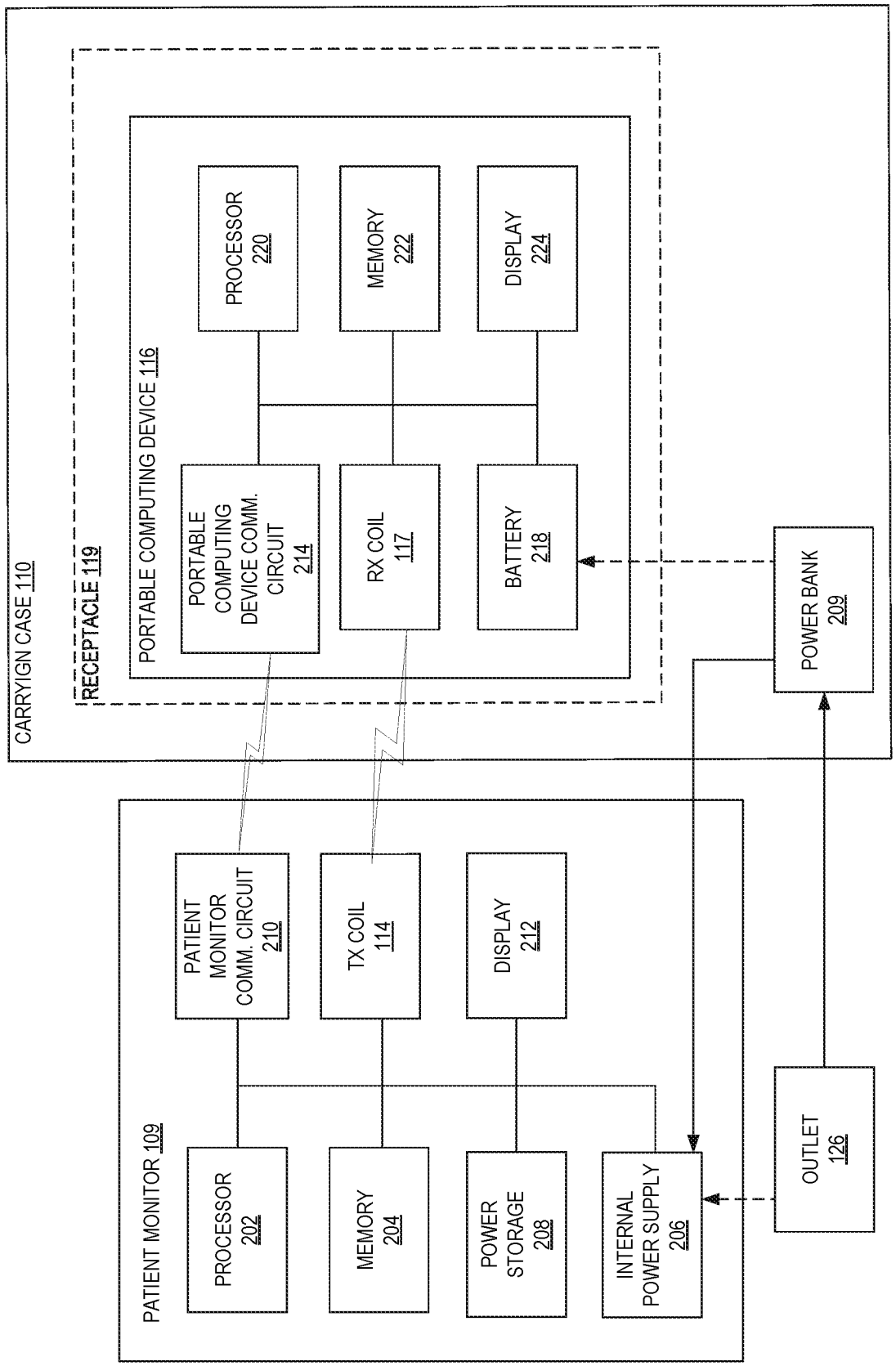
FIGS. 3A-3D illustrate an alternative example of the present system, in which the wireless charging system and transmission coils are located within the patient monitor, in accordance with one embodiment.
Figure 3B:
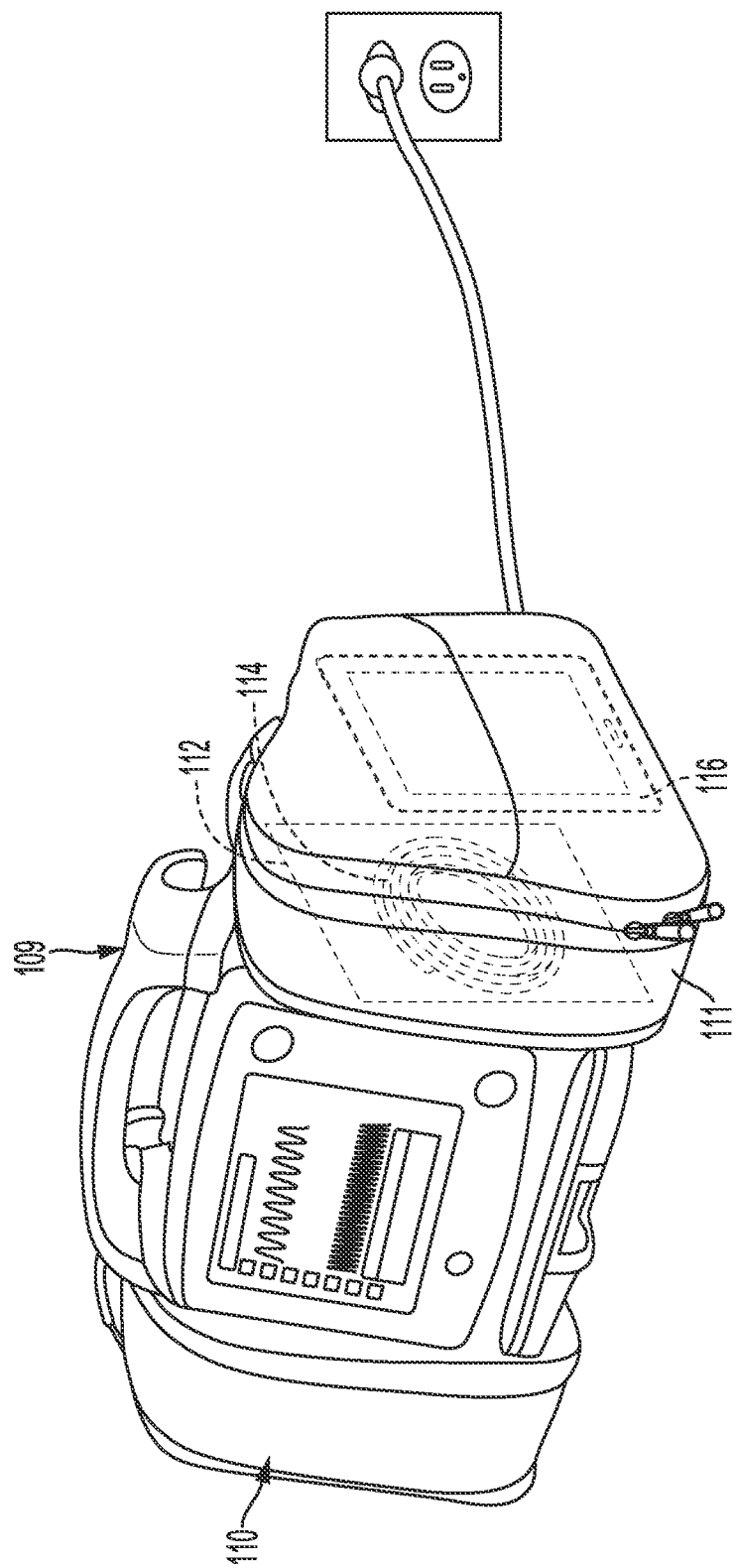
Figure 3C:
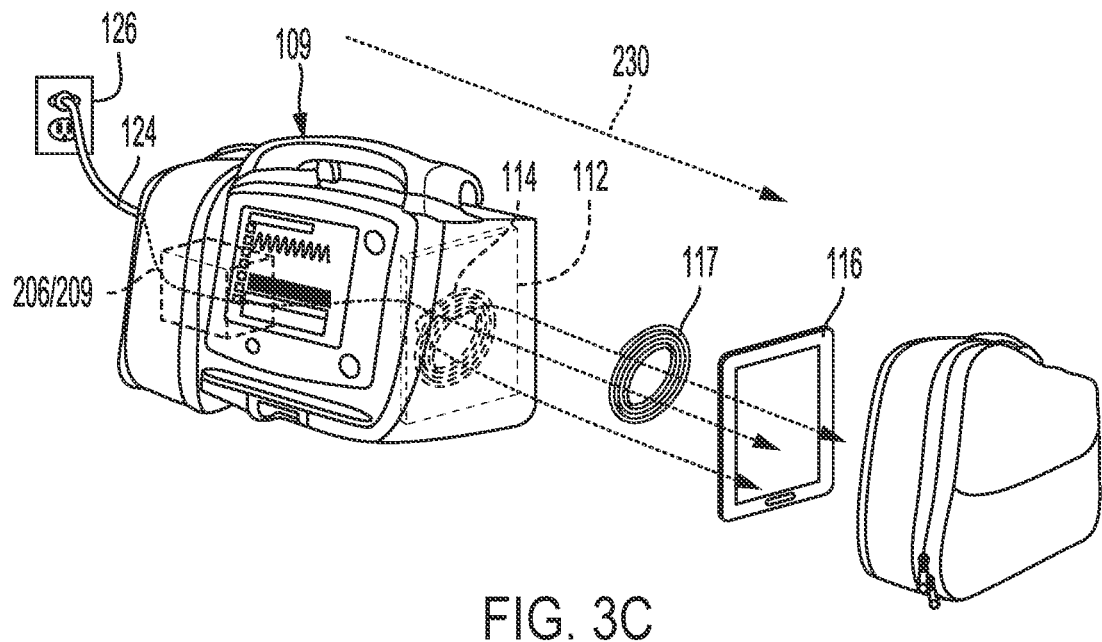
Figure 3D:
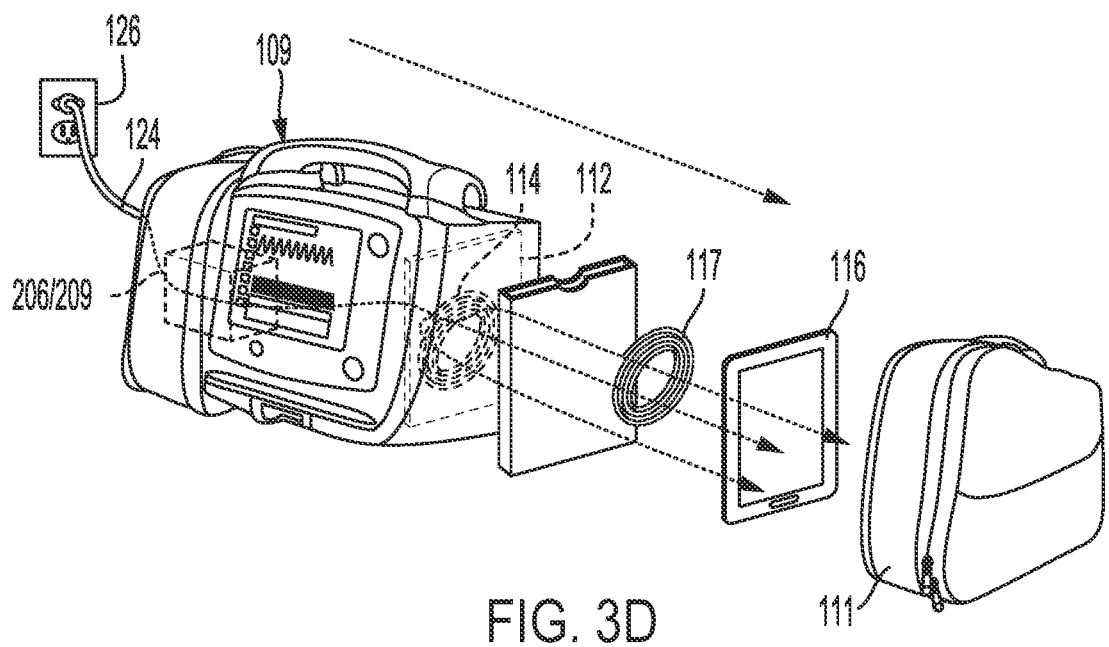
Figure 3E:
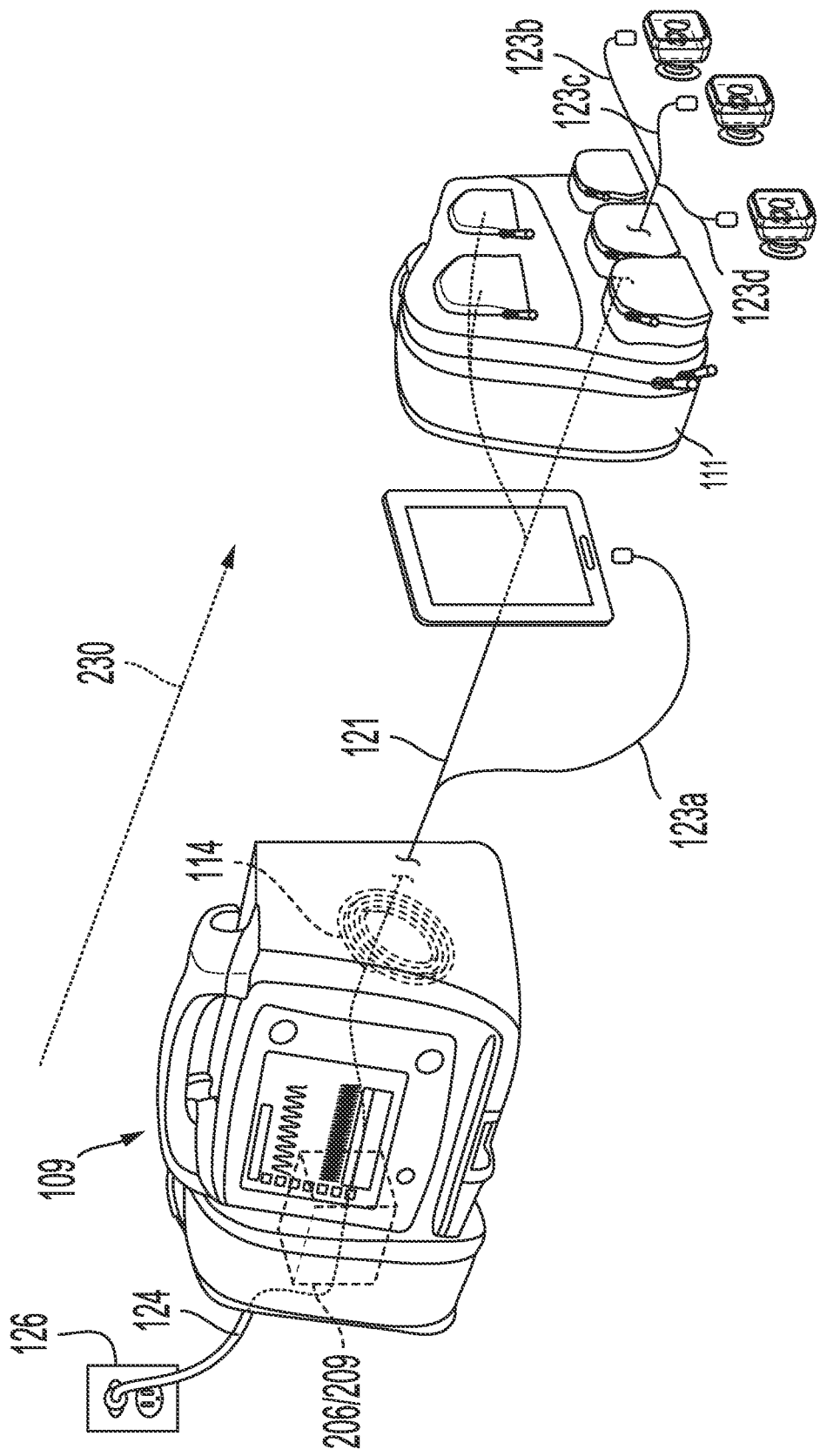
FIG. 3E illustrates another alternative example of the present system that may include charging cables, in accordance with one embodiment.

FIG. 3E is an alternative example of the present system 100 according to one embodiment. In this example, a charging cable 121, with a plurality of branches 123a-d, are run to each of the pockets 140-1 to 140-5 (as labeled in FIG. 1K) for charging the various devices that may be stored in the pockets of the carrying case 110. As wireless charging may not currently be available for every device, the charging cable 121 provides an alternative implementation for charging devices stored within the carrying case 110. Each branch 123a-d may include an interchangeable interface such that the cable is able to interface with a wide variety of devices regardless of which interface (e.g., lighting, USB-C, Micro USB) is used by the device. In operation, rescuers may utilize a combination of wireless charging systems and wired charging cables depending on whether each device is capable of wireless charging.

Furthermore, in some embodiments, some or all of the pockets 140-1 to 140-5 may be configured to store and allow charging of multiple portable computing devices 116. In other embodiments, multiple portable computing devices 116 may be chargeable in any of the ways described with regard to FIGS. 1K or 3E, for example, but one or more of them may be stored and charged other than in pockets of the carrying case 110. For example, in some embodiments, they may be stored and charged on or in a portion of the patient monitor 109, such as in pockets or other receptacles that are part of the patient monitor 109. In other embodiments, they may be stored separately from the patient monitor 109 and the carrying case 110, such as in separate receptacles, stands or holders. As such, in some embodiments, a subset or all of the portable computing devices 116 may be stored separately or more distantly from the patient monitor 109, and may not to be wirelessly chargeable by one or more of the wireless charging systems 112. However, in some embodiments, such portable computing devices 116 may still be charged in a wired fashion by or in coordination with the patient monitor 109, for example, by a charging cable or cables, such as using the charging cable 121 depicted in FIG. 3E.

In various embodiments of the present disclosure, such as those depicted in FIGS. 1A and 3E, for example, the system 100 may include a patient monitor 109, such as a defibrillator/monitor, and multiple portable computing devices 116. In some embodiments, such as the embodiment depicted in FIG. 3E, when one or more of the portable computing devices 116 are not in use by an operators or rescuers, they may be stored so as to be chargeable, such as wirelessly chargeable, by transmission coils 114, which may or may not be part of a wireless charging system 112. In some embodiments, multiple wireless charging systems 112 may be utilized, in which case each may be used to charge one or more of multiple devices, such as the portable computing devices 116. Each of the one or more wireless charging systems 112 may be a part of the patient monitor 109, or may be attached or coupled to the patient monitor 109, or may be separate. For example, as further described herein, one or more of the wireless charging systems 112 may provided in a modular removable pod arrangement such that the mechanical housing of the wireless charging system(s) may be swapped out with a similarly structured housing, yet intrinsically having different functionality.

In some embodiments, the system 100 including the patient monitor 109 (e.g., defibrillator/monitor or monitor without defibrillation capability) and each of multiple different portable computing devices 116 is treated and managed as an integrated whole. This can allow greater efficiency, effectiveness, readiness or overall optimization of the system 100 as a whole and with respect to rescue operations or efforts. This, in turn, can lead to greater effectiveness and chance of success in critical or life-saving rescue operations. For example, system 100 operations may be managed in an optimized, coordinated, comprehensive, holistic or "smart" way.

In particular, the system 100 may be set up to prioritize or optimize device charging (which may be described in some embodiments as "smart charging"), or related energy draw parameters, including with regard to the patient monitor 109 and the multiple portable computing devices 116. The system 100 may also be configured so as to prioritize or optimize data transfer (which can include data communication, data sending, data receiving, and/or data storage), including from the patient monitor 109 to one or more of the portable computing devices 116, from one or more of the portable computing devices 116 to the patient monitor 109, and between portable computing devices. The system may further be prioritized or optimized with regard to an optimized, per-device 109, 116 balance between charging and data transfer, and aspects of each. In some embodiments, such prioritization or optimization may be accomplished utilizing programming, algorithm(s) or optimization algorithm(s), software or one or more "apps" executed or run, or stored and run, on processors one or more of the devices 109, 116, such as the processor 202 of the patient monitor 109 or a processor of one or more selected portable computing devices 116. In other embodiments, such software could be provided, or provided and run, in whole or in part, remotely or using a cloud-based source.

In some embodiments, charging, as well as data transfer, or aspects thereof, may be set as on or off, such as by the processor 202 of the patient monitor 109, based on relevant parameters, and on a per-device basis. Furthermore, in some embodiments, charging or data transfer may be set as on but limited in some way, such as set to a certain or determined rate or rate range based on relevant parameters. Furthermore, whether charging or data transfer is turned on or off, or on but limited, and the degree or nature of any such limitation, may vary over time based on relevant parameters.

In some embodiments, prioritization or optimization may be device-specific, or may be partly or wholly based on a particular storage unit, compartment, sleeve or pocket in which each device is stored, such as pockets of a patient monitor 109 carrying case. For example, in some embodiments, a user may configure the system such that one or more particular devices 109, 116, or devices placed in certain pockets, are prioritized in terms of charging or data communication.

Furthermore, in some embodiments, system prioritization or optimization with regard to charging, data transfer, or both, may be at least partly user-configurable or controllable via user settings, such as via software or one or more "apps" and associated graphical user interfaces, which may be run, or stored and run, on one or more of the devices 109, 116.

Still further, in various embodiments, prioritization or optimization may have binary aspects, such as charging being simply on or off with regard to a particular device 109, 116 at a particular time. However, in some embodiments, optimization may have more a more complex nature, such as by determining and controlling an optimized allocation or distribution of charging or charging energy between devices 109, 116, which could include, for example, determining and providing an optimized percentage of charging energy available over time, to each particular device 109, 116. A similar complex optimization scheme could be applied to aspects of data transfer between devices 109, 116, including processor use or memory use.

As described herein, including with regard to FIG. 6B for example, many parameters may be taken into account in prioritization or optimization. These may include the state or status of each device 109, 116 at a particular time, such as on, off, or in stand-by mode.

However, many other factors may be taken into account. For example, factors may be taken into account that relate to relative clinical importance of each device 109, 116. Other factors may relate charge-providing parameters, such as availability and source of charging, rate of available charging, level of available charging, amount of time or anticipated amount of time of charging, or amount of time or estimated or anticipated amount of time until likely actual use. Other factors may relate to device-specific charge-related parameters, such as the charge rate or maximum charge rate of each device 109, 116, the maximum charge capacity of each device 109, 116, and the amount of usage time needed or available at a given charge level or maximum charge level for each device 109, 116. Other factors may relate to data transfer. For example, such data transfer related factors may include the amount of data involved or required currently or over time, the amount of associated time needed, and the available or anticipated speed or bandwidth of the network or networks. Device-specific data related factors may include, for each device 109, 116, the processor speed and availability, what percentage of processor usage is required or is needed for other processor operations, the storage capacity of the device 109, 116 and the amount of storage capacity required for other operations, and the data transfer capabilities and limits of the particular device 109, 116.

Furthermore, in some embodiments, elements of the power components or power line used to transport and provide power to the devices 109, 116 of the system 100, for example, may also be utilized in data transport and communication. As such, in some embodiments, data may be sent over power cords, wiring or cables, such as using power line communication technology. This may provide greater overall, comprehensive system efficiency, including with regard to priority and optimization relating to data transfer and charging.

In embodiments in which portable computing devices 116 are stored in pockets, compartments, or sleeves, for example, the particular pocket or compartment in which the device is stored may determine or be a factor in charging prioritization. This may allow a degree of user configurability or customization. Furthermore, in some embodiments, the software that is used to determine or control prioritization, optimization or distribution may be user configurable so that a user may configure according to the user's priorities or preferences, such as via a graphical user interface or "app" provided on a device to allow user configuration preference input or settings.

Furthermore, in some embodiments in which multiple portable computing devices 116 are stored or placed for wireless charging, for example, the system 100 may be configured to check to determine if placement or alignment is sufficient to allow charging, and to alert the user accordingly. In some embodiments, this can be implemented using sensors and the processor 202 of the patient monitor 109. For example, the patient monitor 109, carrying case 110 and/or portable computing device 116 could include one or more sensors, such as proximity sensors (e.g., radio-frequency identification (RFID), near field communication (NFC) sensors, Hall-effect sensors, magnetic sensors, and/or optical sensors) that may enable detection of whether one or more portable computing device 116 is placed or aligned so as to allow wireless charging.

as well as other components such as colored LED lights or a speaker. For example, in some embodiments, the system 100 is configured to detect and provide visual or audio confirmation to a user when placement or alignment is sufficient to allow charging, and/or when it is not sufficient. This can include, for example, alert lights, sounds, or audible words from a speaker that may be part of the system 100. In some embodiments, the alerts may not only alert the user when the placement or alignment is insufficient, but also provide the user with input or feedback on how to correct the placement or alignment, such as by directing or instructing the user to move the portable computing device slightly in a particular direction, such as by particular lights turning on, or audio word instructions, for example.

Figure 3F:
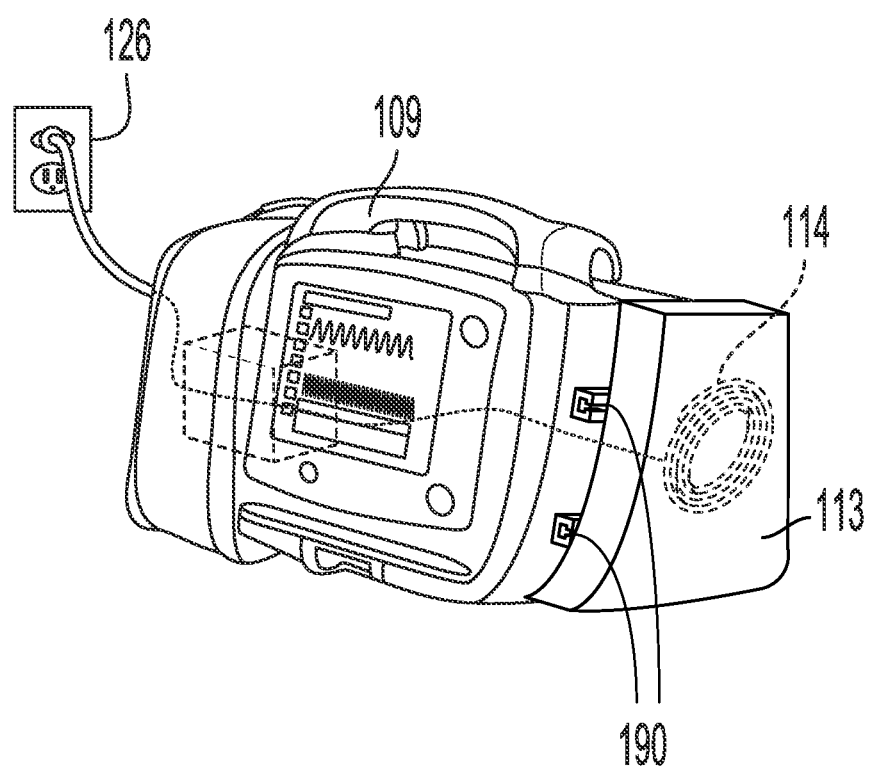
FIG. 3F illustrates another example of the present system, in which the transmission coils are included within a removable/swappable unit that can be part of the patient monitor.

FIG. 3F illustrates another example of the present system, in which the transmission coils 114 are included within a unit 113 that can be part of the patient monitor 109. The transmission coils 114 may or may not be part of a wireless charging system 112. In some embodiments, the patient monitor 109 is configured such that any of one or more various different units, such as pods, modules or cartridges, can be removably coupled to the patient monitor 109, such as by being placed or inserted so as to be stably, rigidly or fixedly be attached to a portion or surface of the patient monitor 109. Once so placed, the unit may become integrated and part of the patient monitor 109. For example, in certain embodiments, the patient monitor 109 may have a receptacle having a recess for receiving the removable unit, and the unit rests flush with the housing of the patient monitor 109 when placed within the receptacle. In some cases, the receptacle of the patient monitor includes mechanical locking features that hold the removable unit in place when properly inserted.

In some embodiments, the unit 113 can be or include any of a number of different types of modules or pods. As depicted, the unit 113 includes a wireless charging system 112 and transmission coils 114 for charging a portable computing device 116. In other embodiments, the unit 113 may include transmission coils 114 only. In some embodiments, the unit 113 may include, or be configured to potentially include or be coupled with, other components, such as a protective sleeve for the portable computing device 116, or other features or attributes, some of which may facilitate alignment or placement of the portable computing device 116 for wireless charging.

As depicted in FIG. 3F, the patient monitor 109 and the unit 113 are configured such that the unit 113 can be easily, quickly and reliably inserted so as to become part of the patient monitor 109. Specifically, as depicted, the patient monitor 109 may be configured to have guide rails to facilitate insertion and attachment of the unit 113, although many different types of attachment or coupling mechanisms and configurations are possible.

In some embodiments, the patient monitor 109, and various types of units 113, are configured such that any of various different types of units 113, with different components and functionality, can used with, or made part of, the patient monitor 109. In some embodiments, more than one unit 113 may be made part of the patient monitor, such as by attaching to different surfaces or parts of surfaces of the patient monitor 109.

The system 100 as depicted may allow a unit 113 to be easily placed, as well as removed and replaced, if desired, with another unit. For example, as shown, the patient monitor 109 is equipped with guide rails 190 for insertion and removal of units 113, and the unit 113 is depicted in a partially removed, or slid out, position. As such, the system 100 may allow units 113 to be "plug and play" and easily and quickly swappable, allowing different and customized configurations of the patient monitor 109. For example, other types of units 113 may include electronic circuitry and/or other structure that allows for various types of functionality, for example, a pneumatic system that provides for non-invasive blood pressure monitoring, or circuitry that would support other sensor types such as capnography, pulse oximetry, ECG monitoring, amongst others. Furthermore, in some embodiments, a group of different types of units 113 may be kept close to or along with the patient monitor 109, so as to allow immediate selection and use of an appropriate unit 113 depending on the circumstances, emergency or rescue operation. As such, some embodiments provide a system 100 that allows for convenient, immediate, customizable configuration of the patient monitor 109, which can be of great use in an emergency medical situation of an unpredictable, or not fully predictable, nature. Alternatively, such swappable units may simply be available for pre-configuration of the overall patient monitor (e.g., defibrillator/monitoring device) by a service technician/specialist according to specifications desired by the facility medical director.

In various embodiments, a unit 113 may attach, for example, for wireless coupling, or wired coupling, or both, so as to function as an integrated part of the patient monitor 109. The choice of what unit 113 or units 113 to include with a particular patient monitor 109, or to include at a particular time or time period with a particular patient monitor 109, may be driven be a variety of factors. These factors may include, for example, an anticipated or most likely use of the patient monitor 109, the environment or setting of the patient monitor 109, preferences of a customer, purchaser, owner, or user of the patient monitor 109, or many other factors.

Figure 4A:
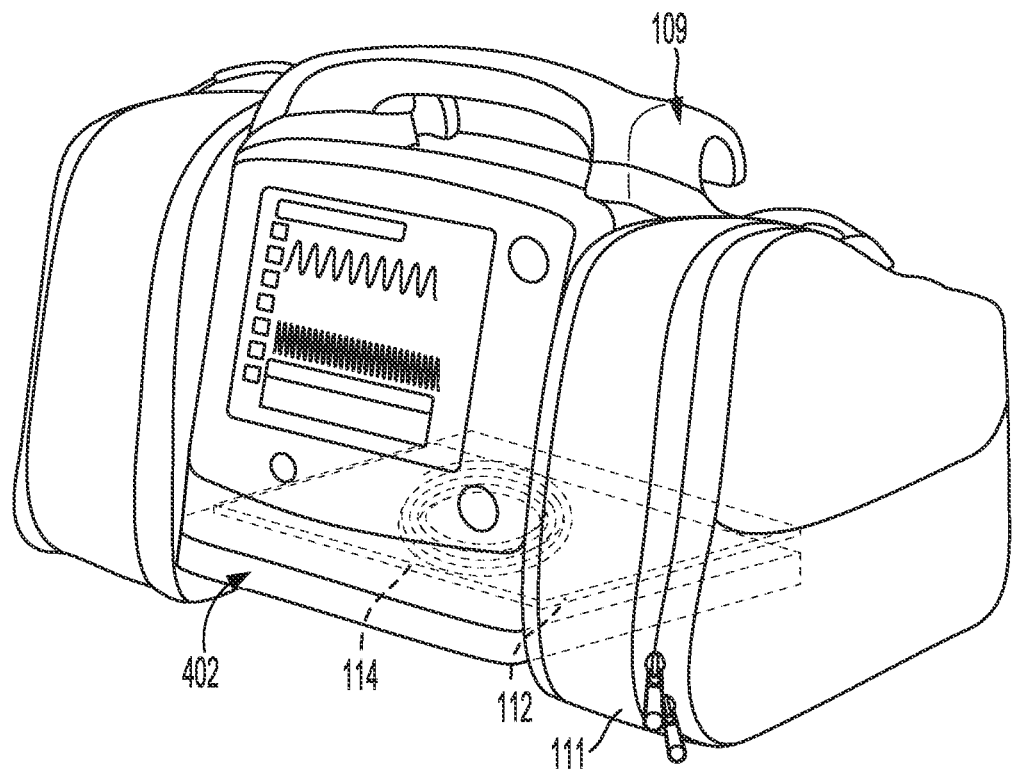
FIG. 4A illustrates another alternative example of the present system according to one embodiment.

FIG. 4A illustrates another alternative example of the present system according to one embodiment. In this embodiment, the portable computing device 116 is stored in a compartment 402 located on the underside of the patient monitor 109. The compartment 402 could be a molded part of the patient monitor 109 or a separate component that may be attached to the patient monitor 109 (either during manufacturing or as a retrofitted accessory). In the illustrated example, the wireless charging system 112 may be installed between the patient monitor 109 and the compartment 402. In some embodiments, the wireless charging system 112 may be attached to the exterior of the patient monitor 109. For example, the wireless charging system 112 may also be located on the underside of the molded housing of the monitor, attached, adhered or otherwise coupled thereto. In various embodiments, the wireless charging system 112 may be part of, attached to, or otherwise provided with the compartment 402. In still another embodiment, the wireless charging system 112 may be provided as a mat that may be adhered or otherwise coupled to a surface within the compartment 402.

Figure 4B:
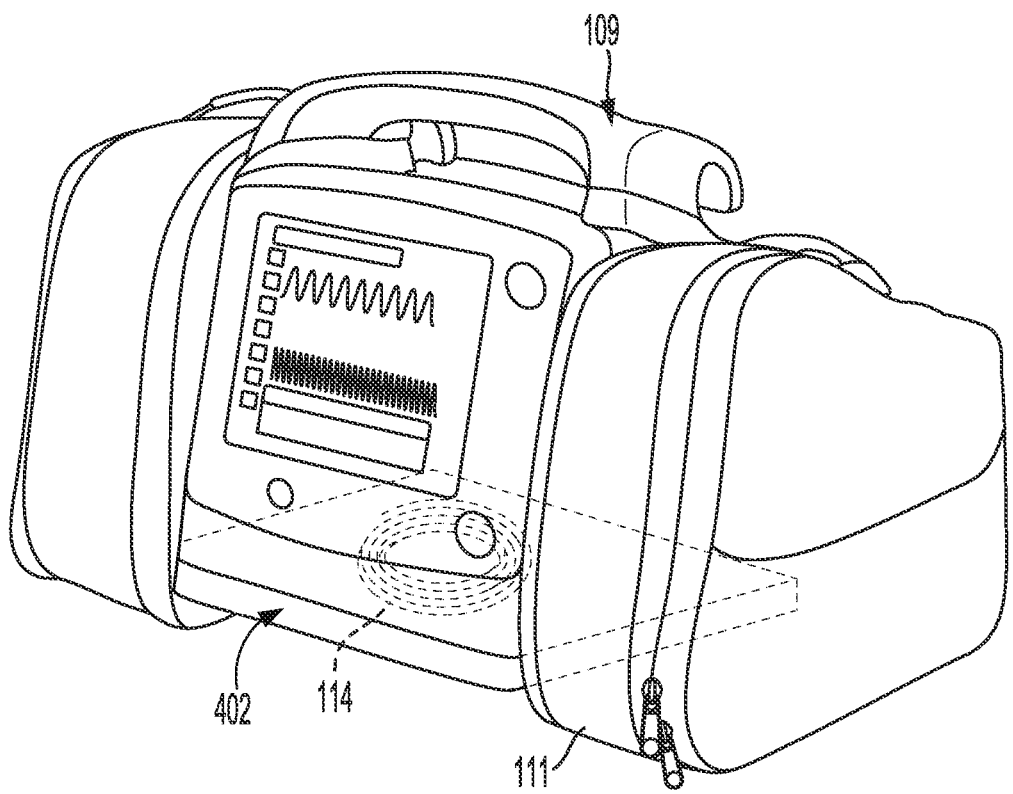
FIG. 4B illustrates yet another alternative example of the present system, according to another embodiment.

FIG. 4B illustrates an alternative example of the present system according to one embodiment. In this embodiment, the transmission coil 114 may be located within the patient monitor 109. That is, the wireless charging system 112 may be integrated as a part of the patient monitor 109 and positioned near the underside thereof. For example, the wireless charging system 112 may be located within the molded housing walls of the patient monitor 109 and placement of the portable computing device against the underside of the patient monitor 109 may be sufficient proximity and alignment to allow for power transfer between the wireless charging system and the portable computing device.

Figure 5A:
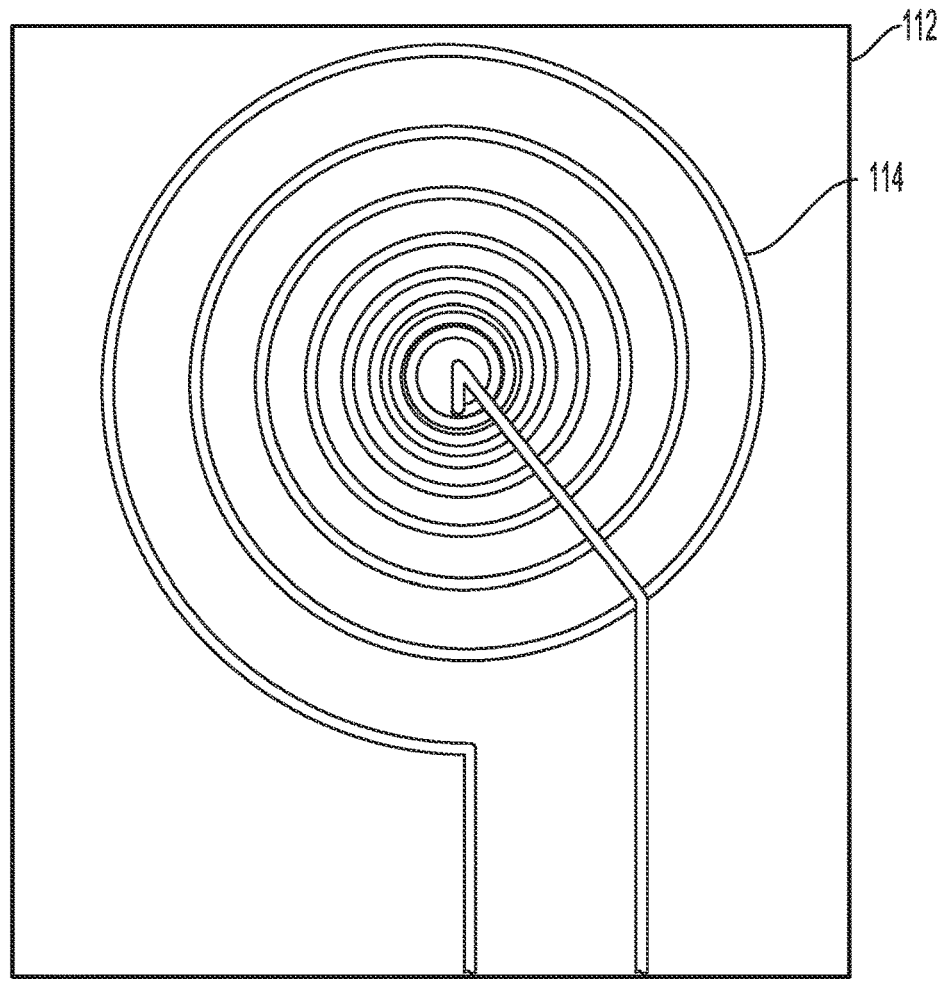
FIG. 5A is a schematic diagram illustrating one embodiment in which the transmission coil of the wireless charging system is approximately the same size as the wireless charging system, in accordance with one embodiment.
Figure 5B:
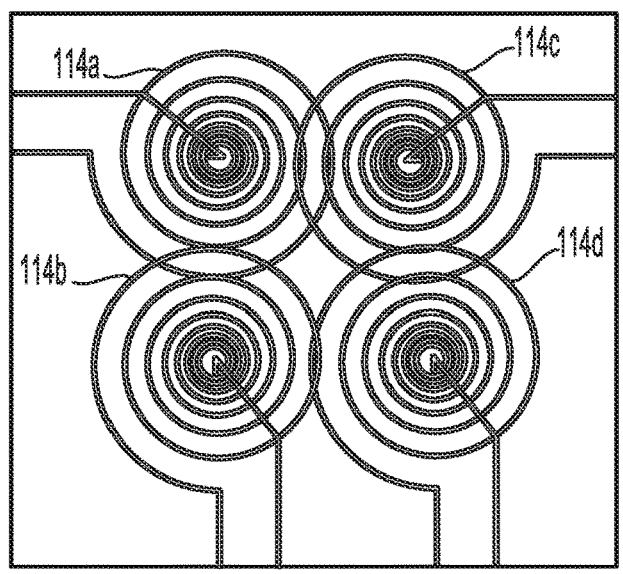
FIG. 5B is a schematic diagram illustrating one embodiment in which the wireless charging system utilizes multiple transmission coils, in accordance with one example of the present system.

FIGS. 5A and 5B illustrate exemplary implementations of the wireless charging system, according to embodiments.

In general, wireless inductive charging included in the presently disclosed systems and devices can comprise an electromagnetic field, generated by a coil of wires to transfer energy from one or more transmission coils to one or more receiver coils via electromagnetic induction. Energy from the electromagnetic field may be received by the receiver coil and may be converted back into electric current, which can then be used to power or charge a battery, for example.

Another example of inductive charging that can be included in the presently described systems and devices can comprise wireless resonant inductive charging, which relies on resonant coupling to further increase the effectiveness of charging. In such resonant inductive charging, the power may be transferred between the coils operating at identical or approximately similar resonant frequencies (e.g., based on coils capacitance, resistance, and inductance). This method of charging takes advantage of the increased coupling that occurs between resonant coils. A benefit of this type of inductive charging is the ability to transfer energy across greater distances, more efficient energy transfer, and the coils typically have a greater tolerance for misalignments of the coils compared to inductive charging.

FIG. 5A is a schematic diagram illustrating an induction coil 114 of the wireless charging system 112. In this embodiment, the coil 114 fills the majority of the area of the wireless charging system 112. As a general rule, the maximum proximity distance may be approximately equal to the diameter of the transmission coil. Thus, one benefit of a larger induction coil is a greater allowable distance between the transmission coils 114 and the receiver coils 117 (while still being able to efficiently transfer power). Additionally, with the coils covering a large surface area, there is often greater flexibility in alignment of the transmission and receiver coils. Thus, even if the transmission coil 114 and receiver coil 117 are not perfectly aligned, wireless charging will still occur, albeit with reduced efficiency.

FIG. 5B is a schematic diagram illustrating another embodiment of the wireless charging system 112, which utilizes multiple overlapping induction coils 114a, 114b, 114c, 114n. While the illustrated example depicts only four coils of approximately the same size, alternative embodiments could implement as many as 24 coils (or another suitable number of coils) in varying sizes and configurations (e.g., layouts or patterns) to ensure there a relatively uniform distribution of magnetic flux. As illustrated, the coils 114a-114n may also be oriented differently to account for various positioning of the receiving coils relative to the transmission coils. Thus, regardless of how the portable computing device 116 is positioned within the carrying case 110, one or more of these transmission coils 114a, 114b, 114c, 114n will likely align with the receiving coil 117 of the portable computing device 116. Additionally, with small coils, the electromagnetic field will also be more narrowly distributed, which provides higher magnetic flux for increased charging efficiency and also minimizes or otherwise reduces potential electromagnetic interference with other electronic devices.

In one example, the wireless charging system 112 may be based on the Freescale MC56F8006 DSC device, as described in Freescale Semiconductor application note, document number AN4705. This paper describes a Freescale low-power wireless transmitter solution (TX) compliant to the "Qi" standard of the Wireless Power Consortium (WPC), using a single-stage full-bridge resonant inverter topology. In this example, the DC input voltage range is 5-16 V with single power stage, with free positioning with multiple primary coils, simple and robust communication demodulation circuit, low-power standby operation, power transfer with digital PID (proportional-integral-differential) close-loop control, and interoperable operation with any receiver device with WPC "Qi" logo. In some examples, any number of coils may be activated simultaneously, for example, in response to a determined alignment of a portable computing device.

In general, the Freescale device includes a power receiver that communicates with a power transmitter using backscatter modulation. A communication demodulation circuit may be used to detect a 2 kHz communication signal from a 108 kHz power signal. A primary coil voltage serves as the input, and the output is communication data following a bit encoding scheme. The circuit of the Freescale device can be divided into five parts, including voltage scale down part, rectify and DC filter part, low-pass filter part, electric level comparator part, and communication wave voltage divider part.

Figure 5C:
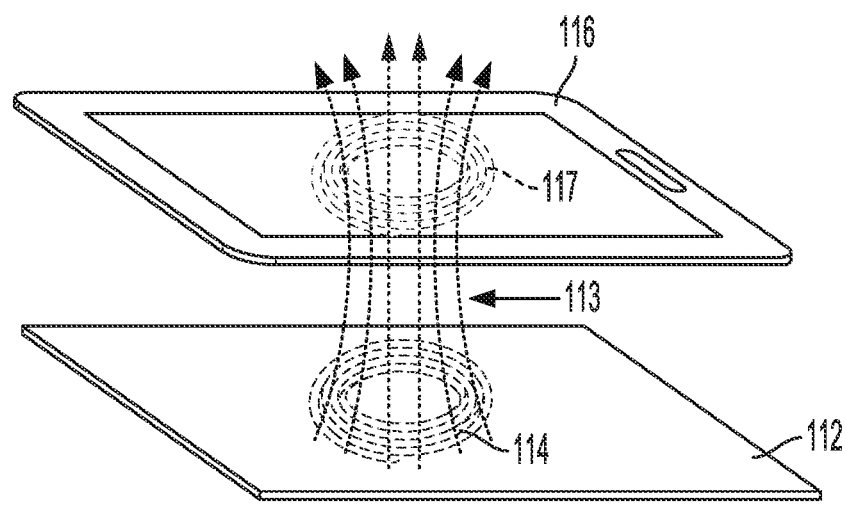
FIG. 5C is a schematic diagram illustrating an electromagnetic field and alignment of the transmission and receiver coils, in accordance with one embodiment.

FIG. 5C is a schematic diagram illustrating an electromagnetic field 113 and alignment of the coils 114, 117 between the wireless charging system 112 and the portable computing device 116. As illustrated, a transmission induction coil 114 within the wireless charging system 112 creates an electromagnetic field 113, and a second (receiver) coil 117 within the portable computing device 116 receives the power from the electromagnetic field and converts the received power back into electric current to operate the portable computing device 16 or charge the battery 218 of the portable computing device 116.

Figure 5D:
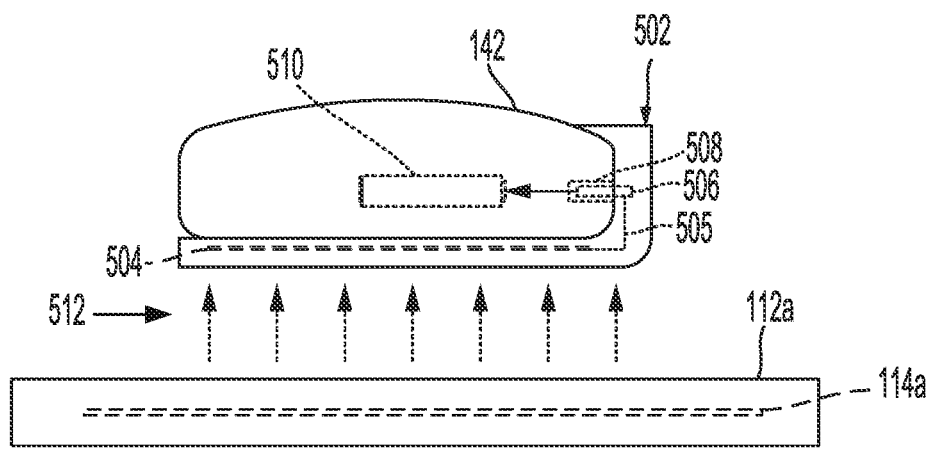
FIG. 5D is a schematic diagram illustrating a wireless charging adapter configured to enable devices without receiver coils to be charged wirelessly, according to one embodiment.

FIG. 5D is a schematic diagram illustrating a wireless charging adapter 502 and a rechargeable device (e.g., wireless sensor 142) connected to the wireless charging adapter 502. Many rechargeable devices include rechargeable batteries that are recharged via a cable that connects to an external power source via an interface of the rechargeable device. The wireless charging adapter 502 enables the wireless sensor 142 to be adapted for wireless charging according to the present system in that the wireless charging adapter 502 provides the wireless charging capabilities for the wireless sensor 142.

In the illustrated example, the wireless charging system 112a includes a transmission coil 114a that generates an electromagnetic field 512, which may be received by the receiving coils 504 within the wireless charging adapter and converted into DC and/or AC current by a receiver circuit (not shown). The received energy runs through a cable 505 from the coils 504 to the adapter interface 506. A corresponding interface (e.g., charging port) 508 of the wireless sensor 142 physically connects to the adapter interface 506, and thus enables charging of the batteries 510 of the wireless sensor 142.

Furthermore, a retractable holder as detailed above, for example, may be attached to the wireless charging adapter 502. In this way, any rechargeable device may be adapted (e.g., retrofitted) for wireless charging and integrated into the system of the present application.

In the illustrated embodiment, the wireless charging adapter 502 acts as a dock (or cradle) that partially surrounds the rechargeable device and cradles the device. This embodiment allows for easy removal/replacement of the wireless charging adapter 502. Alternatively, the wireless charging adapter may be a case that fully surrounds the device (or surrounds a larger portion of the device). In yet another embodiment, the receiver coils may be integrated into a thin substrate, which includes adhesives to adhere to the device. Additionally, the substrate would also include a cable that runs from the substrate to the charging interface.

Figure 6A:
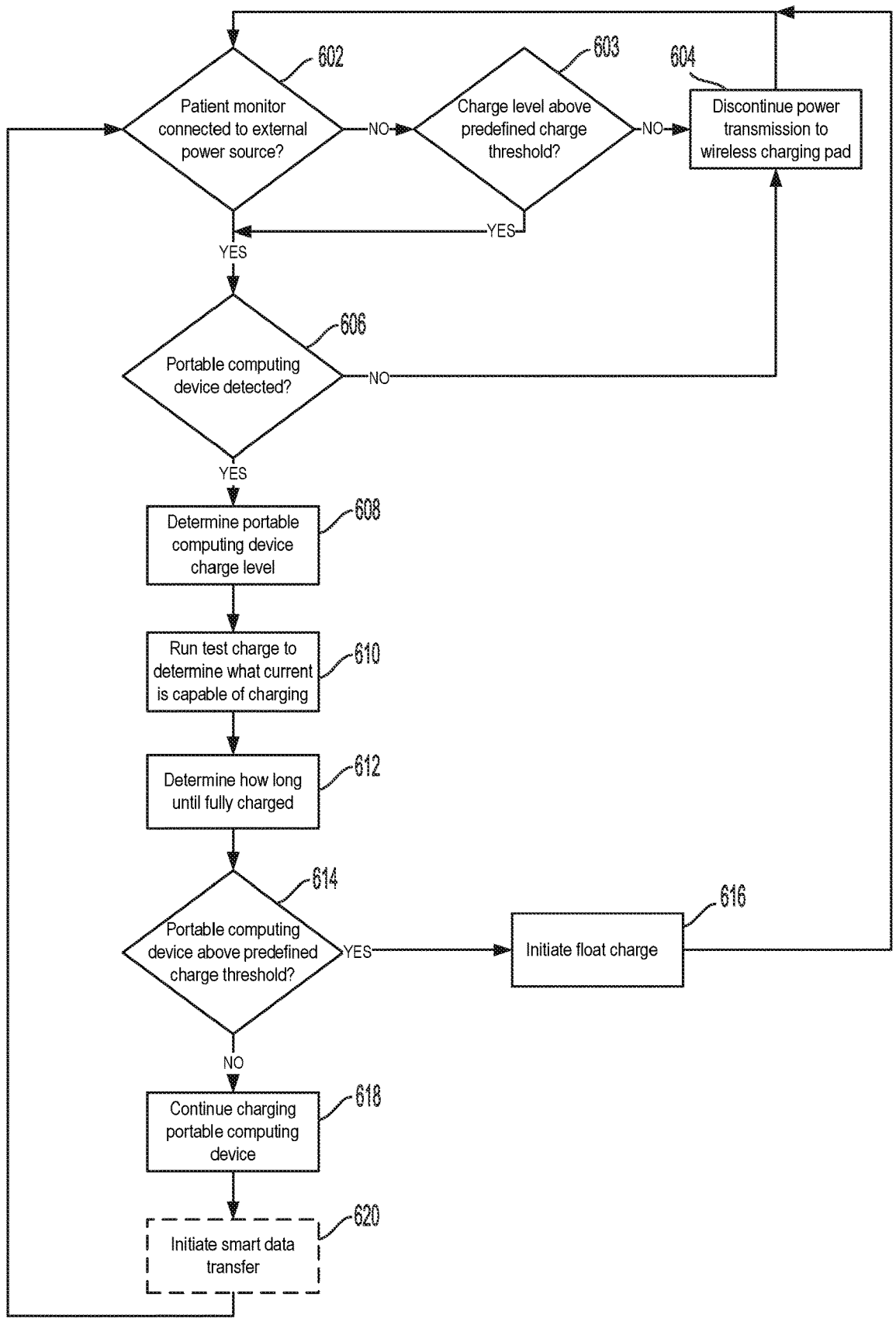
FIG. 6A is a flowchart illustrating steps performed by the patient monitor and portable computing device in order to perform selective charging, in accordance with one example of the present system.

FIG. 6A is a flowchart illustrating the steps performed by the patient monitor 109 and portable computing device 116 in order to perform intelligent (or smart) charging, in accordance with one example of the present system. In some examples, recharging of the portable computing device 116 may be precluded when the patient monitor 109 is operating solely from the power storage device 208 (e.g., battery) and/or if the battery of the portable computing device 116 is below a threshold charge level (e.g., below 60%, below 70%, below 80%, below 90%). This is because, while it would be advantageous for the portable computing device 116 to always be fully charged and ready for use, it is more important that the patient monitor 109 has sufficient power for clinical use. It could be dangerous and possibly life-threatening if the patient monitor 109 lacked sufficient power to treat to patient 102 when it is called upon for clinical usage/operation.

In some embodiments, however, various power options (or settings) of the patient monitor may 109 be configurable to enable the patient monitor 109 to allow charging when the patient monitor 109 is unplugged. In this embodiment, charging would be permitted if the charge level in the power storage device 208 of the patient monitor 109 is above a predefined charge threshold (e.g., above 60%, 65%, 70%, 75%, 80%, 85%, 90%, 95% etc.). The predefined charge threshold will generally be determined based on the capacity of the power storage device 208 of the patient monitor 109 and/or an amount of power required to operate the patient monitor 109. As detailed previously, for certain embodiments, the power storage device 208 should be large enough to operate the patient monitor 109 for 8-10 hours.

In the first step 602, the patient monitor 109 determines whether it is connected to an external power source. If the patient monitor 109 is not connected to an external power source, then the patient monitor 109 may perform optional step 603. In optional step 603, the patient monitor 109 determines whether the charge level in the power storage device 208 is above the predefined charge threshold. If the power storage device 208 is not above the predefined charge threshold, then the patient monitor 109 discontinues power transmission to the wireless charging system in step 604. If, however, the charge level is above the predefined charge threshold, then the patient monitor 109 goes to step 606 to determine if a portable computing device 116 is detected.

Returning to step 602, if the patient monitor 109 is connected to an external power source, then the patient monitor 109 determines if a portable computing device 116 is detected in step 606. The patient monitor typically determines whether a portable computing device 116 is present and at a proximity sufficient to enable charging by measuring the electromagnetic field created by the transmission coil and determining if there is a disruption to the field due to the presence of a compatible device. Alternatively, test signals may be sent to check for a change in the capacity or resonance. The change in capacitance or resonance would be indicative that a compatible device is present. In yet another embodiment, the patient monitor 109 and/or portable computing device 116 have corresponding proximity sensors (e.g., radio-frequency identification (RFID), near field communication (NFC) sensors, Hall-effect sensors, magnetic sensors, and an optical sensor) that provide the ability for the patient monitor to detect when the portable computing device 116 is in sufficient proximity so as to initiate charging and/or data transfer.

In one example, an RFID reader could be installed within the patient monitor 109 and/or carrying case such that the RFID reader may be communicatively coupled with the patient monitor 109. Likewise, one or more unique RFID tags could be installed within the portable computing device 116 (or other wireless devices), which may serve to identify that particular portable device, as opposed to other portable devices associated with the patient monitor 109. Hence, when the particular portable computing device 116 associated with the patient monitor 109 is identified, power and/or data transfer may be permitted. As the portable computing device 116 has a battery 218, the RFID tags could be passive or active tags. Then, when the portable computing device 116 is within proximity to the patient monitor 109, the RFID reader would interrogate the RFID tag. Upon receiving a response from the RFID tag, the patient monitor 109 could confirm the identity of the portable computing device 116 via the unique tag number and also confirm that the portable computing device 116 is within a required or desired range. Once the portable computing device 116 is within the required or desired range, the patient monitor 109 may begin wireless inductive charging and/or data transfer.

Hall effect sensors are sensors that measure the potential difference across an electrical conductor when a magnetic field is applied in a direction perpendicular to that of the flow of current. The output voltage of a Hall effect sensor is proportional to the magnitude of the magnetic field strength through it. In one example, one or more magnets may be installed in, or on, the portable computing device 116. Similarly, one or more Hall sensors may be installed within the patient monitor 109, carrying case 110, or with the wireless charging system 112. As the portable computing device 116 is placed in proximity to the Hall sensor(s), they would then detect the magnetic field at the various sensors to determine the proximity between the magnet and sensors. The patient monitor 109 would be able to confirm that the portable computing device 116 is in proximity to the wireless charging system and within range and properly aligned before beginning wireless charging.

NFC or Near-field communication is a communication protocol similar to RFID that enables two electronic devices to establish communication by bringing both devices into close range, usually approximately 4 centimeters (approximately 1.6 inches) or less. In one example, an NFC reader could be installed within the patient monitor 109, carrying case 110 of the patient monitor, or with the wireless charging system 112. Additionally, one or more NFC tags could be installed within the portable computing device 116 (or other wireless devices). Then, if the portable computing device 116 is within range (e.g., approximately 4 cm) of the NFC reader (e.g., installed with the patient monitor, carry case, wireless charging system), the reader would be able to interrogate the NFC tag within the patient monitor 109. As with RFID technology, the patient monitor 109 could confirm the identity of the portable computing device via the unique tag number and confirm that the portable computing device 116 is within range. Once the portable computing device 116 is within range of the patient monitor 109, it may begin wireless charging of the portable computing device 116 and/or data transfer between the patient monitor 109 and the portable computing device 116.

Optical sensors are detectors that sense light, and then transform the sensed light into an electronic signal that indicates an amount of sensed light and/or is proportional to the amount of sensed light. In one embodiment, a sensor may be affixed to the portable computing device 116 or installed within the carrying case 110 to detect light from an emitter. The position of the emitter and sensor would be such that the sensor would only be able to detect light when the portable computing device 116 was properly aligned within the receptacle or carrying case 110.

Referring back to step 606 in FIG. 6A, if no portable computing device is detected, then the wireless charging is discontinued (or not started) in step 604, which then results in the process flow returning back to step 602. If a portable computing device is detected, then in step 608, the patient monitor 109 may determine a charge level of the portable computing device 116 (if not done previously in step 603). Next, the patient monitor 109 optionally runs a test charge to determine what is the maximum current the portable computing device 116 is capable of handling in step 610. Based on the determined charge level and charging capability, the patient monitor 109 then calculates the amount of time until the portable computing device 116 will be fully charged in step 612, for example, based on the current charge level and what current level the portable computing device is able to handle. This information may be displayed graphically on a display of the portable computing device 116 as a battery with a percentage indicating the current charge percentage of the battery of the portable computing device 116. Additionally or alternatively, text such as, "one hour and 20 minutes until fully charged" could also be displayed. In embodiments which utilize multiple portable computing devices 116-1 to 116-3, and additional wireless devices (e.g., wireless sensors, smartphones, etc.), information for all of the devices could be displayed in an interface indicating charge levels for each device.

In some embodiments, in addition to the charge state, feedback related to whether the device is present (i.e., in the carrying case 110) and properly charging could also be implemented. For example, an icon that displays which device(s) is not charging. This would serve the purpose of showing what accessories are detected and charging. Additionally, an indication that a device is not charging could be an indication that an item was missing (e.g., left at the scene, left in the ambulance) faulty, improperly aligned/orientated, or not within close enough proximity to a wireless charging system.

Additionally, some embodiments may implement an indicator on the carrying case 110 or on the patient monitor 109 such as multiple lights (e.g., LED or light emitting diodes) that shows which of the accessories that are present in their respective pockets or storage locations. Likewise, the LED may change color and/or blink to indicate charge status. For example, a solid red LED may indicate a device is charging, a solid green LED green may indicate fully charged, a red blinking LED may indicate a problem with charging (e.g., a foreign object or incompatible device), and a yellow LED may indicate poor/weak charging. Each of the LED could be labeled or numbered (e.g., each number associated with one of the pockets) such that only when a device is present, is an associated LED illuminated. Or, in some embodiments, a display on the carrying case 110 or on the patient monitor 109 may provide an indication of charging status.

Next, in step 614, the patient monitor 109 determines if the portable computing device 116 is fully or adequately charged up to a base threshold charge level that provides sufficient comfort for the rescue team to know that the portable computing device will be functional for the time period in which it is or will be used. Such a threshold charge level may, for example, be 60%, 65%, 70%, 75%, 80%, 85%, 90%, 95%, 100%, or another suitable percentage level of charge for the portable computing device. The base threshold charge level may be a configurable amount that is preset by an administrator user. If the portable computing device 116 is fully or adequately charged, then the patient monitor 109 may switch to float charging in step 616. In some embodiments, float charging is a charging method in which charging over time is limited to an amount that maintains the capacity or voltage of a power source or battery at, or nearly at, full capacity or charge by compensating for self-discharge of the power source or battery, while not over-delivering charging. For example, float charging can include a method of reducing the amount of energy delivered such that the amount of energy provided is the same amount of energy as would be used by the device if unplugged (and not in use). Additionally, the portable computing device 116, wireless charging system, and/or patient monitor 109 may utilize overcharge protection circuits to disable charging and prevent damage to either the patient monitor 109 or the portable computing device 116 in the event of an error or other failure during charging.

If the battery is not fully charged, then the patient monitor 109 continues to provide power to the wireless charging system 112 to enable energy to continue to be transferred to the portable computing device 116 in step 618. In the next step 620, the patient monitor 109 may initiate selective data transfer between the patient monitor 109 and the portable computing device 116 (as detailed below with respect to FIG. 6B).

FIG. 6B is a table illustrating exemplary "states" (e.g., ON, STANDBY, OFF) for the patient monitor 109 and the portable computing device 116. While not illustrated, additional states (e.g., a hibernate mode, administrative mode, a repair/service mode, a practice mode) could also be utilized by the patient monitor 109 and/or portable computing device 116. In general, the table provides an indication of whether the patient monitor 109 is able to charge the portable computing device 116 and/or initiate data transfer with the portable computing device 116, depending on the respective states of each device.

In general, when describing the portable computing device 116 and/or the patient monitor 109, "ON" may refer to a state in which the device is fully powered on, activated, and/or ready for immediate clinical use. "STANDBY" (or STANDBY mode) may refer to a state in which the device is not in a fully active state, but also is not shut down, either. Depending on how each device is configured, some devices may still be able to transmit and/or receive data in STANDBY mode. That is, STANDBY mode may disable only a few components or features, or nearly all of the features of the device. Applications may still remain running in standby mode, or be disabled (depending on how the users configure the mode). A benefit of this mode is that many features of the devices may still operate in the background and the devices may be able to switch "ON" immediately when needed and be ready for immediate use. This switching feature is sometimes referred to as "instant on."

The final state may be "OFF," and refers to a state when the devices are fully shut down. In this state, the devices may still be able to charge their respective batteries (and operate the wireless charging system in the case of the patient monitor 109), but generally, none of the functions of the devices are available in this state. Additionally, the devices would need to power on, and run through their respective boot sequences prior to active or clinical use.

Turning to the table of FIG. 6B, and more specifically, to the column labeled "COMPUTING DEVICE (CHARGE)." As detailed previously, a general operating principle of the current system may be that the patient monitor will only be able to wirelessly charge the portable computing device 116 via the wireless charging system 112 when the patient monitor is plugged in. This operating principle serves as a safety feature to prevent the portable computing device 116 from draining power from the patient monitor 109 when the patient monitor 109 is unplugged. Thus, as illustrated, wireless charging is ENABLED when patient monitor 109 is plugged in and is "OFF" when the patient monitor is unplugged. As detailed above, charging may be permitted if the charge level is above a predefined threshold. In this embodiment, the "OFF" state could be replaced with "OFF (depending on charge level)."

Referring to the top third of the table labeled ("PORTABLE COMPUTING DEVICE STATE: OFF"), this section of the table is directed to scenarios when the portable computing device 116 is OFF. Referring to the column labeled, "COMPUTING DEVICE (DATA), when the portable computing device 116 is in an OFF state, no data is able to be transferred to/from the portable computing device 116. However, as shown, even when the portable computing device 116 is in an OFF state, the portable computing device 116 is still able to be charged wirelessly via the wireless charging system if the patient monitor 109 is plugged in.

The middle third of the table (i.e., PORTABLE COMPUTING DEVICE STATE: ON) is directed to scenarios in which portable computing device 116 is ON (e.g., active and ready for clinical or other active use). If the patient monitor 109 is plugged in and ON and the portable computing device 116 is ON, then data transfer is ENABLED. In one embodiment, the patient monitor 109 and/or portable computing device 116 may utilize "push" technology. Push technology refers to a scenario in which one device "pushes" information to one or more other devices. The benefit of using push technology is that whichever device is configured to transmit information at an appropriate time will initiate the transfer to the other device(s) whenever there is new information that needs to be transferred.

This section of the table generally refers to a situation in which, e.g., the portable computing device 116 and patient monitor are in a rescue scenario (clinical mode) and the data would be transmitted to/from either device (or to other devices or sensors in the system). In one example, the portable computing device 116 may be used to input patient information, for example, name, age, gender, height, weight, and/or allergies, and such information may be transmitted to the patient monitor 109 for integration into a patient record (or patient case data) and/or used for further processing. For example, patient information may be used to determine various resuscitation parameters, such as the appropriate defibrillation shock energies (higher shock energy for adult patients as compared to pediatric patients), target ventilation tidal volume (based on ideal body weight, which uses gender and height of the patient as the inputs) for manual ventilations, ventilation rate for manual ventilations, chest compression depth and/or rate for chest compressions, amongst others. In still another example, the portable computing device 116 may include network connectivity (e.g., 3G, 4G, 5G cellular networks, Wi-Fi) and be able to access information from external sources such patient records database, hospital records, or other caregivers, for example. Information obtained from external sources by the portable computing device 116 may be shared with patient monitor 109 or with other portable computing devices (e.g., 116-2 or 116-3).

As also described herein, the patient monitor 109 may provide data to the portable computing device 116 according to a particular mode set by the user. For example, if the user sets the portable computing device to a chest compression mode, then the patient monitor may transmit chest compression information (e.g., gathered via a motion sensor such as an accelerometer placed on the sternum of the patient during the administration of chest compressions) to the portable computing device, for providing feedback to the user as to whether the user is providing chest compressions according to desired targets (e.g., target compression rate and depth). Similarly, if the user sets the portable computing device 116 to a ventilation mode, the patient monitor 109 may transmit ventilation information (e.g., gathered via a pressure and/or flow sensor positioned in the airway of the patient during the administration of ventilations) to the portable computing device 116, for providing ventilation feedback to the user according to desired ventilation targets (e.g., target tidal volume and ventilation rate). Or, the user may set the portable computing device to a supervisor mode where vital sign information is transmitted from the patient monitor to the portable computing device, for display thereof for the holder of the portable device. In some embodiments, the user may set the portable computing device to a documenting mode where the user may be able to document certain events (e.g., shock administered, chest compressions administered, a drug or medication administered, intubation tube placed, etc.) that have occurred so as to be able to have a complete record of occurrences. As the user documents events during the medical event, the portable computing device 116 may be configured to transmit the documented events to the patient monitor 109, for integration into an overall patient care record. It should be appreciated that other types of data transfer between the portable computing device and the patient monitor may occur, such as for example, software updates, medical device status reports (e.g., device readiness reporting, self-test results, electrode expiration, battery expiration, event logs, etc.).

Returning to the table, if the patient monitor 109 is plugged in and in STANDBY mode, and the portable computing device 116 is ON, then data transfer is in an ENABLED (IF CONFIGURED) mode. As detailed previously, STANDBY mode is user configurable. Thus, some users may elect to have data transferred in STANDBY mode, while other rescuers configure the portable computing device not receive data. In this case, the patient monitor 109 will transfer data to the portable computing device 116 as long as the settings for the portable computing device 116 are configured to do so. For example, depending on the situation, it may or may not be preferable for the patient monitor (when in STANDBY mode) to transfer data to the portable computing device. When the patient monitor is plugged in and in STANDBY mode, the default configuration may be for all relevant data to be transferred to and from the portable computing device. Though, if the patient monitor is unplugged and in STANDBY mode, it may be preferable for only certain types of data to be transferred to and from the portable computing device. For example, in such a case when the patient monitor is unplugged and in STANDBY mode, clinical information such as patient data and information related to the emergency event may be transferred, though, other less time-sensitive data such as software updates may be withheld until the patient monitor is plugged in and/or in a different mode.

In general, the default setting is to have data transfer enabled when the devices are in STANDBY mode as this generally reduces or eliminates the need to synchronize (e.g., download or transfer) any information between the devices. For example, where rescuers are in transit to an emergency event, it may be beneficial for the patient monitor 109 and portable computing device 116 to be fully synchronized, updated, and ready for active use, while also minimizing power consumption. A benefit of this configuration is that both devices will be ready for use immediately upon arrival at the emergency.

Additionally, it would be further beneficial to ensure that all of the requisite and/or relevant data has already been transferred prior to switching from STANDBY mode to ON (on either device). For example, if a rescuer enters information about the patient's age or gender into the portable computing device 116 prior to arriving at the emergency (or the information is received from remote personnel via network connectivity) then this data can be seamlessly synchronized to the patient monitor 109 prior to being switched from STANDBY to ON. In another example, after a rescue has occurred, the portable computing device 116 and/or portable computing device 116 may need to synchronize information for a post-case debriefing. This synchronization (e.g., bi-directional communication) could also occur when the patient monitor is in STANDBY mode.

If the patient monitor 109 is plugged in and OFF, and the portable computing device 116 is ON, then data transfer is OFF. Obviously, if the patient monitor 109 is powered off, then the data transfer will not be available between the devices.

Lastly, the ability to transfer data when the patient monitor 109 is unplugged is similar to when the patient monitor 109 is plugged in. As illustrated, when the patient monitor 109 is unplugged and in the ON mode, and the portable computing device 116 is in the ON mode, then the transfer of relevant clinical data between the patient monitor and the portable computing device 116 may be able to occur. Similarly, if the patient monitor is unplugged and in STANDBY mode, and the portable computing device 116 is ON, then data transfer is ENABLED (IF CONFIGURED). Lastly, if the patient monitor 109 is unplugged and OFF, and the portable computing device 116 is ON, then data transfer is OFF because the patient monitor 109 is powered off.

Referring to the bottom third of the table (i.e., PORTABLE COMPUTING DEVICE STATE: STANDBY). As illustrated in the figure, when the portable computing device 116 is in STANDBY mode, the data transfer rules are broadly similar to when the portable computing device 116 is in the ON mode. As mentioned previously, the ability to configure what data is transferred when in STANDBY mode enables the devices to synchronize when the devices are in STANDBY mode such that both devices can be switched from STANDBY to ON and be ready for immediate clinical use. Accordingly, when the portable computing device 116 is in a STANDBY mode, then it may be preferable for data transfer to be fully functional in the background processes of the device such that the user is unaware that the data transfer is occurring.

If the patient monitor 109 is plugged in and ON, and the portable computing device 116 is in STANDBY mode, then data transfer is ENABLED (IF CONFIGURED). As detailed previously, the benefit of enabling the data transfer in STANDBY mode is to synchronize data transfer between the patient monitor 109 and portable computing device 116 when the portable computing device 116 is in STANDBY. This allows the portable computing device, despite being in STANDBY, to be continuously updated as the patient monitor receives data. Similarly, if the patient monitor is plugged in and in a STANDBY mode, and the portable computing device 116 is in STANDBY mode, then data transfer is ENABLED (IF CONFIGURED). If the patient monitor is plugged in and OFF, then data transfer is OFF because the patient monitor is powered off.

As illustrated in the figure, the ability to transfer data to the portable computing device 116 from the patient monitor when the patient monitor is unplugged is similar to when the patient monitor is plugged in. Therefore, if the patient monitor is unplugged and ON, and the portable computing device 116 is in STANDBY mode, then data transfer is ENABLED (IF CONFIGURED). As detailed previously, the benefit is such that when the portable computing device 116 is switched ON, the portable computing device 116 is instantly ready for use (e.g., clinical use). If the patient monitor is unplugged and the portable computing device 116 is in STANDBY mode, then data transfer is ENABLED (IF CONFIGURED). If the patient monitor is unplugged and OFF, then data transfer is OFF because the patient monitor 109 is powered off.

Figure 6C:
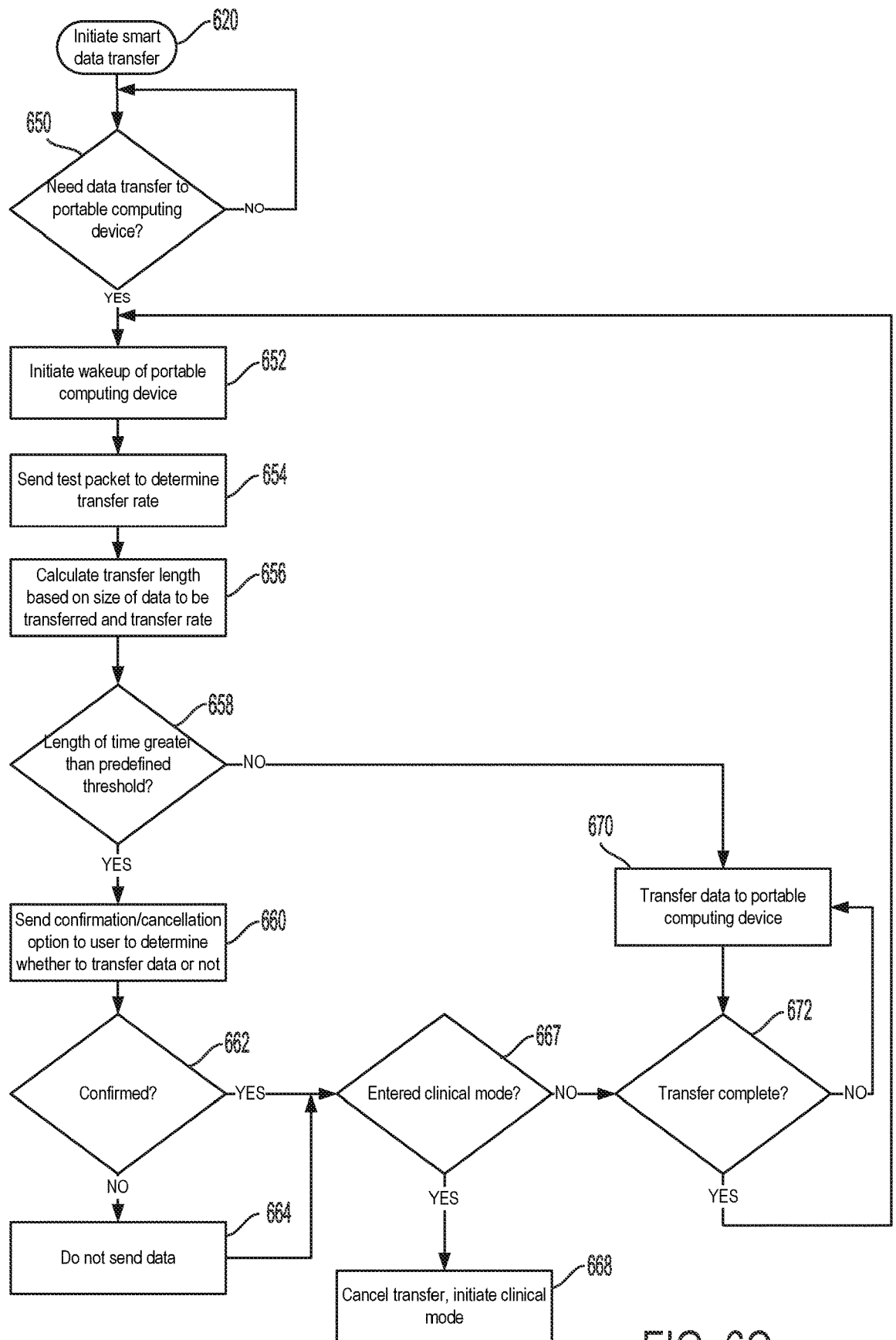
FIG. 6C is a flowchart illustrating the steps performed by the patient monitor and portable computing device in order to perform selective data transfer, in accordance with one embodiment.

FIG. 6C is a flowchart illustrating exemplary steps performed by the patient monitor 109 and portable computing device 116 in order to perform data transfer of a relatively large amount of non-clinical data that is not immediately related to an emergency event (e.g., software, firmware, or protocol update), in accordance with one example of the present system. While FIG. 6C focuses primarily on data transfer from a patient monitor 109 to a portable computing device 116, it is to be understood that data may also be transferred and stored from one or more portable computing devices 116 to the patient monitor 109, as well as from one portable computing device 116 to one or more other portable computing devices 116.

There are many situations in which substantial data transfers, which are not clinical in nature or related to an immediate emergency event, may occur between the patient monitor 109 and the portable computing device 116 (or multiple computing devices 116-1 to 116-3). However, as the patient monitor 109 is a life-saving device, there should never be a situation where the patient monitor 109 is unusable due to large amounts of non-immediate clinical data being transferred to or from the portable computing device 116. For example, a software or firmware update may need to be pushed between the patient monitor 109 and portable computing device 116. Likewise, after a rescue event, data from one device may need to be synchronized to the other device, or to a central facility or an external location (e.g., web server, hospital database). Depending on the length and severity of the rescue event, there could be significant amounts of data that need to be transferred. While it would be ideal to enable the devices to synchronize information without interruption, the unpredictability of when the next rescue event may occur, necessitates that the rescuers be able to cancel such large data transfers mid-transfer, and the patient monitor 109 can switch to clinical mode (e.g., ready for use) at any time, despite being in the middle of a relatively large file transfer.

In the first step 650, the patient monitor 109 determines whether data needs to be transferred to the portable computing device 116. If no data needs to be transferred to the portable computing device 116, then the patient monitor 109 enters a wait state. If data needs to be transferred, then the patient monitor 109 initiates a wake-up of the portable computing device 116 in step 652, if the portable computing device 116 is not ON or in STANDBY mode. In step 654, the patient monitor 109 may optionally send one or more test packets to determine the data transfer rate between the patient monitor 109 and the portable computing device 116. Next, the patient monitor 109 calculates how long it will take to transfer all of the data based on the size of the data needing to be transferred and the calculated transfer rate from step 656.

In the next step 658, the patient monitor 109 determines whether the length of time it would take to transfer the data is greater than a predefined threshold. In general, this predefined threshold is based on information sizes and should be large enough to ensure that patient information is always transferred. The predefined threshold should be set such that patient information such as ECG waveform, ETCO2 waveform, rate, depth, force, pressure, acceleration, release velocity, hold time, event markers, or text (name, gender, height, weight) are always below the threshold. Large data transfers (e.g., software/firmware updates, status updates, or post case debriefing synchronization) may require a user/rescuer confirmation (as further detailed below). The status reports may include one or more of an indication of a level of charge of the battery of the portable computing device, an update of data sent from the patient monitor to the portable computing device, and an update of data sent from the portable computing device 116 to the patient monitor.

Returning to step 658, if the length of time required to transfer the data is greater than the predefined threshold, then an alert and/or confirmation is presented to the user in step 660 to enable the user to determine whether or not to initiate the data transfer. For example, if the data transfer is directed towards software or firmware updates, or configuration information, then the rescuers need to make an affirmative decision of whether to initiate the transfer immediately or, e.g., to wait until a later time or date. In an alternative embodiment, the patient monitor 109 may be configured such that any firmware or software update may not be available/possible until the patient monitor enters an administrative mode. Similarly, the patient monitor 109 may be configured such that post-case information transfer may only be permitted in the administrative (or similar mode). In this way, any downloading/synchronization of non-immediate information will only occur when the device is not in clinical mode.

In step 662, the patient monitor 109 determines whether the user (e.g., the rescuer) confirmed the transfer. If the user does not confirm the data transfer, then the patient monitor 109 will not begin the data transfer in step 664 and check to see if the rescuers have entered a clinical mode in step 667. If the user confirms the initiation of data transfer in step 662, then the patient monitor 109 determines whether the clinical mode has been entered by the rescuers in step 667. Such a determination may be made, for example, via an input from the rescuer for the patient monitor 109 to enter into the clinical mode (e.g., pressing of the power button, or other input, on the patient monitor). Alternatively, the input may be from a rescuer using the portable computing device 116.

If the rescuers have entered clinical mode, then the patient monitor 109 immediately cancels the transfer of non-clinical data unrelated to the emergency event and enters (i.e., initiates) the clinical mode in step 668. Once the patient monitor 109 has entered into the clinical mode, then data transfer of clinical information is enabled. As detailed above, the ability to immediately cancel any transfer and enter into clinical mode is important to ensure that the patient monitor 109 can be switched into the clinical mode for immediate clinical use and transfer of clinical data to and from the portable computing device 116 at any time. If the rescuers have entered clinical mode, then the patient monitor 109 transfers relevant clinical data to the portable computing device. While step 667 is illustrated as a single step in a single branch of this flowchart, in operation of the patient monitor 109, the check of whether the patient monitor 109 has been switched into clinical mode is continually performed (e.g., a software or hardware interrupt). Thus in practice, the patient monitor 109 could interrupt any step to switch into the clinical mode for immediate clinical use. It should also be noted, however, that the canceling of data transfers may not apply to the data (i.e., less than the predefined threshold) associated with patient information because the patient information should always be transferred when the patient monitor 109 has entered into the clinical mode.

Returning back to step 658, if the length of time required to transfer the data is not greater than the predefined threshold (i.e., smaller than the threshold), then the patient monitor 109 initiates the transfer of the data to the portable computing device 116 in step 670. In the next step 672, the patient monitor 109 determines whether or not the transfer has been completed. If the transfer has been completed, then the patient monitor 109 returns to step 650 to determine if data needs to be transferred. If the transfer is not complete, then the patient monitor 109 returns to step 670 to continue the data transfer.

While the illustrated embodiment describes data being transferred from the patient monitor 109 to the portable computing device, a similar flowchart could be implemented for transferring data from the portable computing device 116 to the patient monitor 109.

Figure 7A:
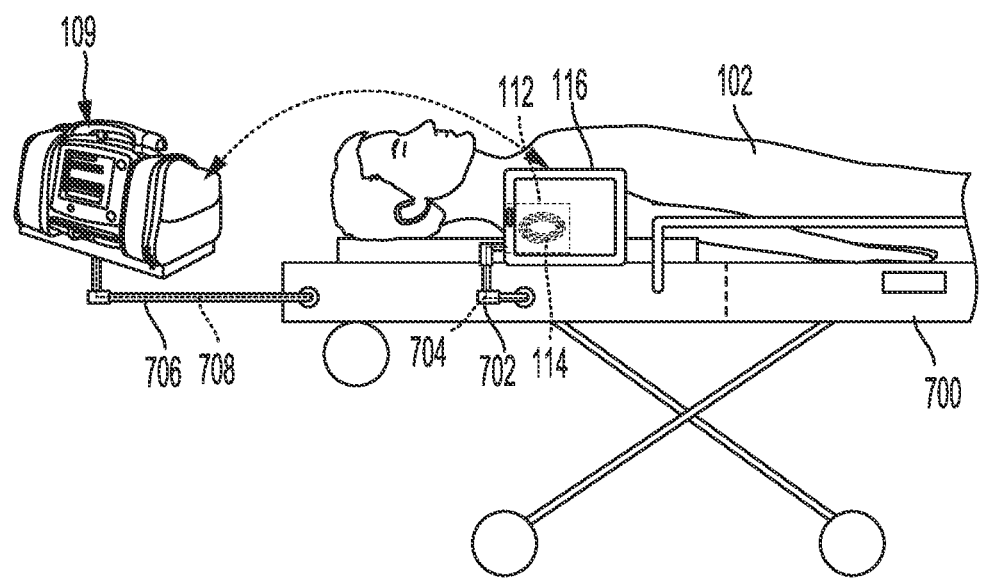
FIG. 7A illustrates one example of how the patient monitor and portable computing device may be used in a clinical situation, according to one embodiment.

FIG. 7A illustrates an example of how the patient monitor 109 and portable computing device 116 may be used in a clinical situation, according to one embodiment.

In the illustrated example, the patient 102 is on gurney 700. Mounted to the gurney 700 is a first 3-axis or 4-axis gimbal (gimbal) 702. In general, a gimbal is a support that allows rotation of an object (affixed to the gimbal) about a single axis. Consequently, a three-axis gimbal combines multiple gimbals and allows the object to move in 3 different axes independent of movement from a person or object holding the gimbal. The fourth axis generally provides dampening of vertical (e.g., up and down) motion. With the use of gimbals, the influence of external motion is typically reduced or possibly eliminated. In some examples, the gimbal joints may be motorized with power from, for instance, a battery located in the frame of the stretcher. By using accelerometers and inertial sensors, the relative movement of the portable computing device 116 relative to the rescuer while the gurney is in motion can be minimized, so that users may be able to view the portable computing device in a relatively steady manner.

The first gimbal 702 includes an attachment mechanism for the portable computing device 116. Additionally, a power line 704 runs through the various arms of the gimbal 702 and provides power to a wireless charging system 112 and transmission coil 114 to provide power and charging to the portable computing device 116 when attached to the gimbal 702. The patient monitor 109 may also be similarly affixed to a second 3-axis or 4-axis gimbal 706 that also includes a power line 708 to provide power to the patient monitor 109. A benefit of this configuration is that the patient monitor 109 and portable computing device are both powered from the gurney and rescuers may position the devices however they wish around the patient. Additionally, any external motion relative to the rescuer, for example from rolling the gurney through the hospital or due to travel in an ambulance, is reduced, and the display of the portable computing device 116 will be more easily readable and touch-screen controls will be more usable.

While the illustrated examples are described with respect to multi-axis gimbals, other motorized mechanisms for reduction movement, shaking, or vibrations may be implemented. For example, mechanical dampers, springs, or struts that absorb motion and movement of the devices may be used in place of, or in addition to, the gimbals 702, 706.

FIG. 7B illustrates another example of how the portable computing device 116 may be used in a clinical situation, according to another embodiment. This gurney in this embodiment is similar to the embodiment described with respect to FIG. 7A. Additionally, another portable computing device 116-2 could be mounted to an IV pole 712 via a mounting mechanism 714. Further, as detailed previously in other embodiments, the wireless charging system 112 and the transmission charging coil 114 may be integrated into the mounting mechanism 714 to enable charging of the portable computing device 116. In the illustrated embodiment, the mounting device is a clamp, however numerous other mounting mechanisms (e.g., pole mount brackets, strap bracket, hook and loop fasteners) could also be implemented.

In general, there are many different varieties of IV poles in the medical field for supporting intravenous fluids and medical devices. These IV poles typically enable gravity feed of fluids (medicines, blood, saline, etc.) contained in IV bags. As these poles, in some form or another, already are used in abundance in most hospitals, ambulances, doctor offices, and medical flight helicopters, it makes sense that the could be used for more than just holding IV fluids. Additionally, in many cases, the IV pole may already be affixed directly to a stretcher or gurney. Thus, the unused portion of the pole could make a useful location to position the portable computing device 116-2. The rescuers would be able to both an interact with the portable computing devices 116-1, 116-2, but also be able to provide treatment to the patient.

Figure 7C:
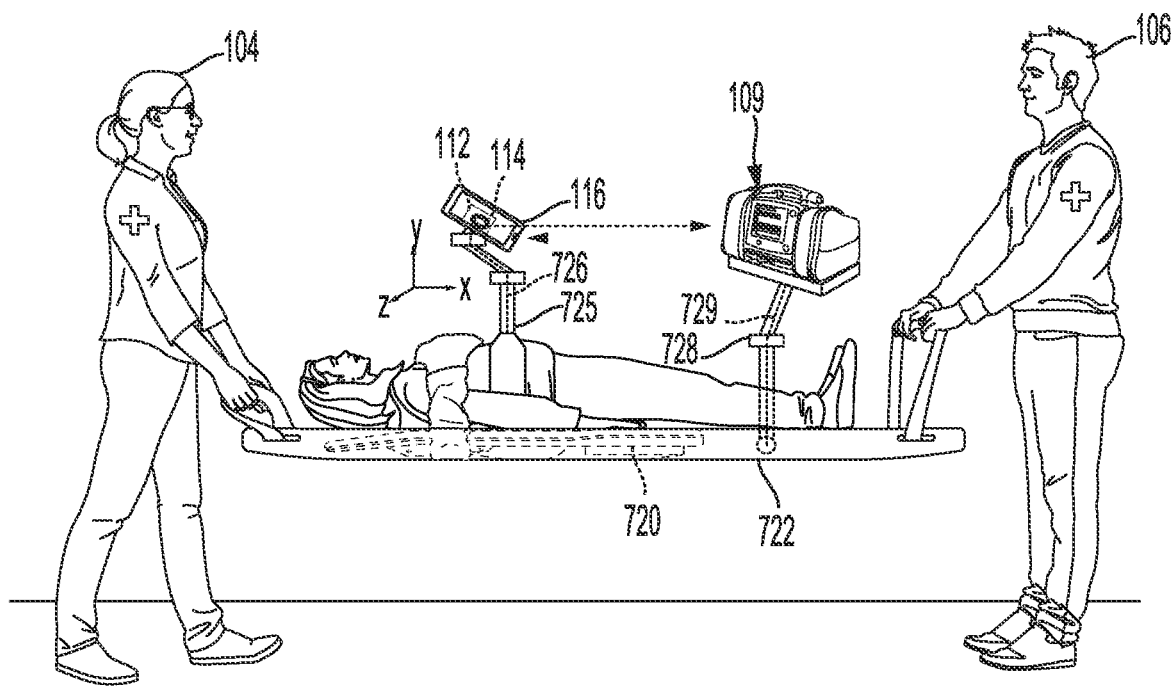
FIG. 7C illustrates another example of how the patient monitor and portable computing device may be used in a clinical situation, according to one embodiment.

FIG. 7C illustrates yet another example of how the patient monitor 109 and portable computing device 116 may be used in another clinical situation, according to another embodiment.

In the illustrated example, the patient 102 is placed on an automated chest compression device 720 (such as, the AutoPulse® Resuscitation system by ZOLL Medical Corporation of Chelmsford, MA), which is supported by a handheld stretcher 722. The stretcher 722 may be a soft stretcher, which a stretcher manufactured from a flexible, but durable material such as canvas, nylon, or similar synthetic material. A benefit of this configuration (i.e., automated chest compression device and soft stretcher) is that the patient can be receiving high-quality chest compression from the automated chest compression while the rescuers 104, 106 maintain a high degree of maneuverability because the patient neck and spine remained secured, but the patient legs can be maneuvered as needed (e.g., to move around tight corners or to fit into smaller elevators that would otherwise not fit a patient lengthwise on a typical gurney, stretcher, or backboard).

Affixed to the patient and/or the backboard of the automated chest compression device 720 is a motorized 3-axis or 4 axis gimbal (motorized gimbal) 725, which provides a mounting mechanism for the portable computing device 116. Within the mounting mechanism is a power cord 726 for supplying power to the wireless charging system 112 and inductive charging coils 114, which provide wireless power to the portable computing device 116. The motorized gimbal 725 is an active system that utilizes a processor and plurality of sensors (e.g., axis, acceleration, tilt, rotation, inertial, or gravity) to measure any movement external to the gimbal 725 and then the processor controls (e.g., adjusts) the position the gimbal to counteract and cancel the detected movement such that the portable computing device remains in the same positional relative to the base of the gimbal. In this way, regardless of how the soft stretcher is moved about, the motorized gimbal 725 will nullify those external movements.

Similarly, the patient monitor 109 may also be similarly affixed to a motorized gimbal 728, which also includes a power line 729 to provide power to the patient monitor 109.

Figure 7E:
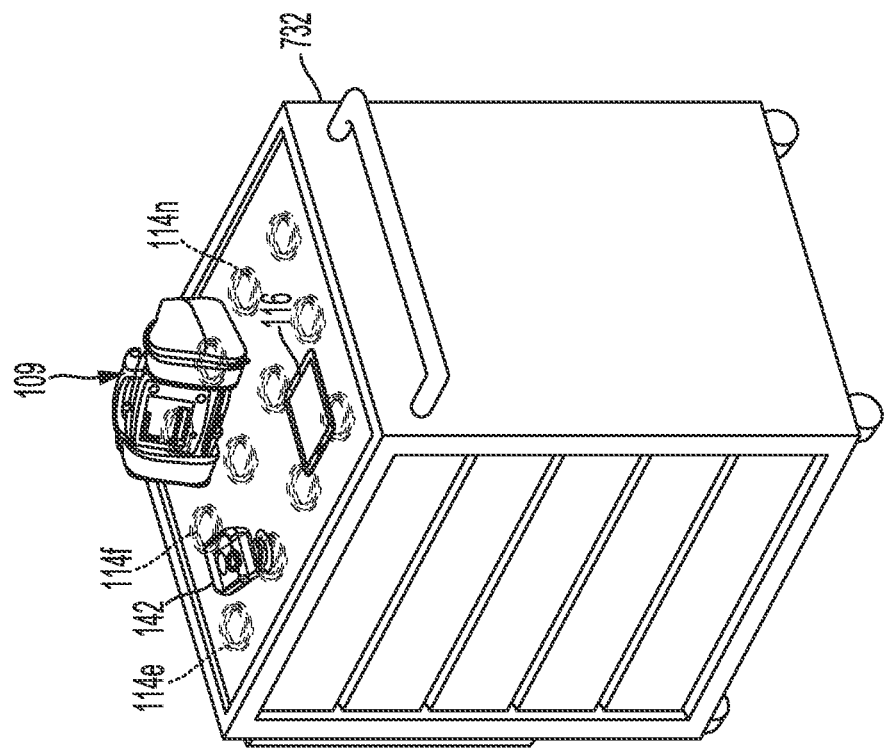
FIG. 7E illustrates another example of how a series of inductive coils could be integrated into the crash cart, in accordance with one implementation.
Figure 7D:
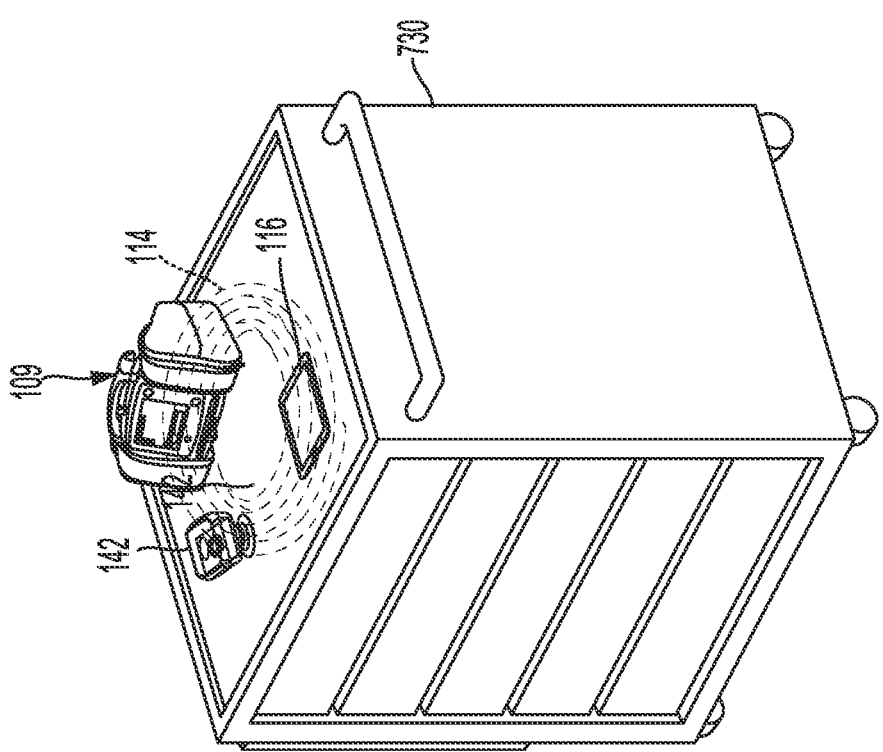
FIG. 7D illustrates one example of how a large charging coil could be integrated into the crash cart, in accordance with one implementation.

FIGS. 7D and 7E illustrate examples of how wireless charging may be integrated with crash carts (or code carts) in order to provide wireless charging of a plurality of devices simultaneously.

Figure 7F:
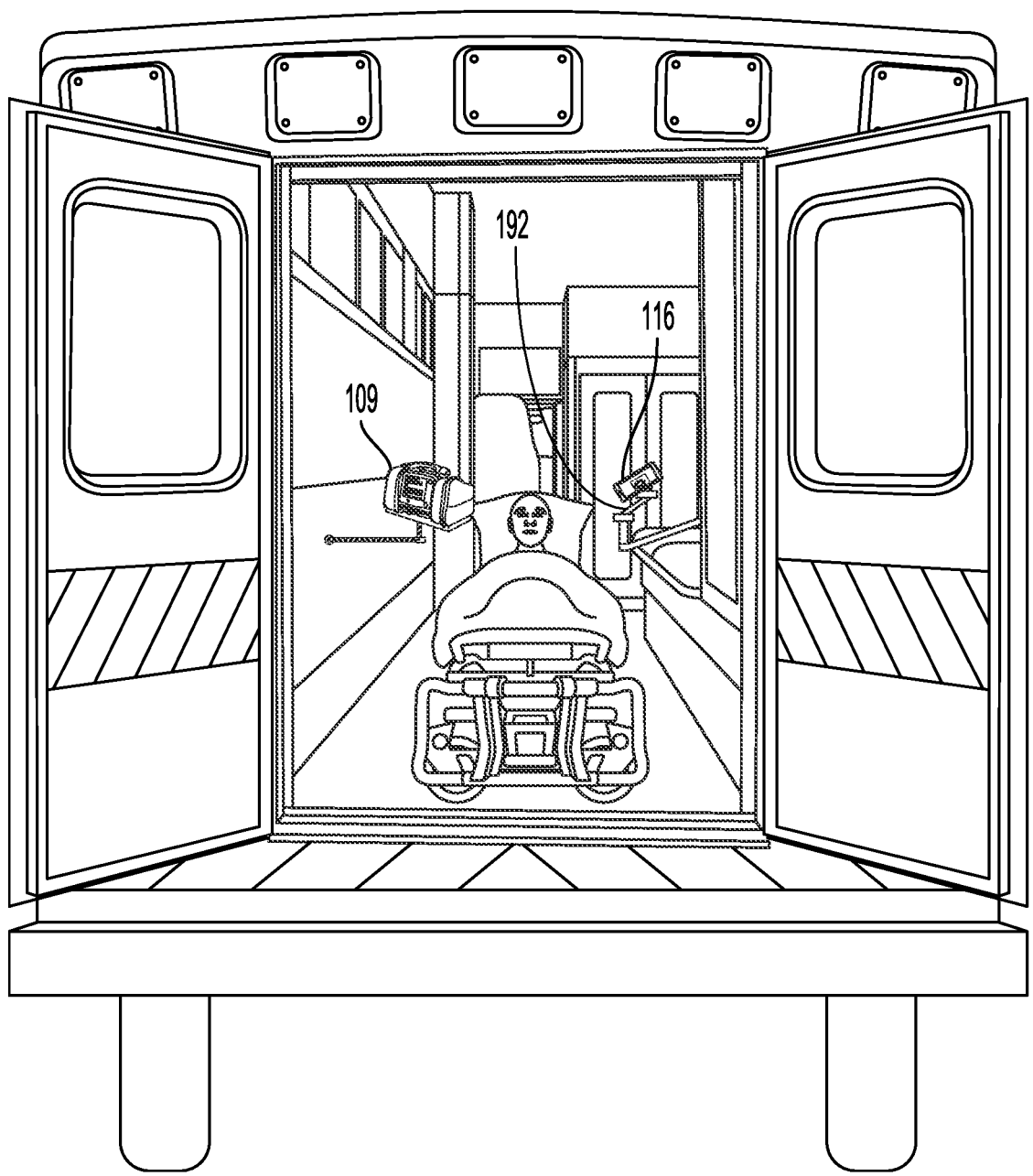
FIG. 7F illustrates an example of an embodiment including a portable computing device mounted on a mount within an emergency vehicle such as an ambulance.

FIG. 7F illustrates an example of an embodiment including a portable computing device 116 mounted, for example, within a vehicle such as an ambulance. Although only one portable computing device 116 is depicted in FIG. 7F, some embodiments include multiple portable computing devices 116, at least some of which may be mounted in different locations within the vehicle, for instance. The portable computing device 116 is mounted on a surface on one side of the patient in the vehicle, and the patient monitor 109 is positioned on a surface on the other side of the patient. The mount 192 may be configured to enable a user of the portable computing device 116 to position it stably for optimal practicality and viewing, which can save time and be of critical importance in a rescue situation. Many embodiments of the mount 192 are possible. In the embodiments depicted, the mount 192 includes a support rod and an attached holder for the portable computing device 116. In some embodiments, mounts, which may include holders, are utilized, as are known in the art, with various components and couplings, that provide some or all of up to a full six degrees of freedom for stable positioning by a user of the portable computing device 116, including position (i.e., surge, heave, sway) and orientation (i.e., yaw, pitch, roll).

In general, it is typically not feasible to stock every single room in a hospital with every single piece of medical equipment that might be used in every emergency situation. Rather, hospitals often utilize crash carts, which are mobile carts with a plurality of drawers, trays, and/or shelves and is stocked with various lifesaving medications, supplies, and medical equipment that may be required when responding to emergencies (or codes).

The exact style and contents of each crash cart typically varies from hospital to hospital, but generally crash carts will include some or all of the following: a patient monitor (e.g., professional style defibrillator/monitor or automated external defibrillator), airway intubation tools, (e.g., tracheal tubes, suction devices, laryngoscopes), bag valve mask (BVM), oxygen face masks, nasal oxygen tubes, an oxygen canister, IV packs with saline solutions, IV tubing, and various medications (e.g., Aspirin Tablets, Nitroglycerin, Dextrose, Narcan, Epinephrine, Atropine Sulfate, Amiodarone, Benadryl, Adenosine, Lopressor, and Cardiazem), Angiocaths (various sizes), gauze, gloves, tape, and alcohol preps, just to list a few examples.

As detailed above, crash carts may include electronic devices such as defibrillators or portable computing devices. FIG. 7D illustrates one example of how a large wireless charging coil could be integrated into the crash cart 730, in accordance with one implementation. As shown in the figure, a single, large coil is integrated into a top shelf of the crash cart 730. Alternatively, the coil could be integrated into a mat or charging system that is placed on the top shelf area of the crash cart. As detailed with respect to FIG. 5A, one of the benefits of this configuration (i.e., a large loop) is the greater distance at which the loop is still able to charge devices. Thus, the devices could be a fair distance away from the surface where the coil is integrated and still be able to charge wirelessly. For example, as illustrated in FIGS. 8A-8D, the portable computing device 116 may be mounted/attached to the defibrillator and positioned on top of a patient monitor 109. With a properly sized and powered coil, the portable computing device 116 could still be able to charge, despite being several inches away from the surface of the crash cart. Additionally, as illustrated, with a large coil, the portable computing device 116 and/or patient monitor 109 can be placed almost anywhere on the cart 730 and still be charged wirelessly. Likewise, other devices capable of wireless charging (e.g., wireless sensors, smartphones, smartwatches, and other smart devices) could also be placed on the crash carts and be charged wirelessly, as well. Additionally, in embodiments in which the transmission coils are integrated into the patient monitor (as detailed in FIG. 3A), these coils and their associated circuitry could be configured to also receive power. To ensure full coverage of the surface, a series of smaller coils could also be implemented.

FIG. 7E illustrates an alternative example of how a plurality of coils 114e, 114f, 114n could be integrated into the crash cart 730, in accordance with one implementation. For clarity on a small number of coils are shown. In practice, the entire surface area may be completely covered and coils may overlap to ensure complete coverage. Similar to FIG. 5B, the plurality of coils 114e, 114f, 114n may be integrated throughout a top surface area (or shelf) of the crash cart 730. As detailed previously, one of the benefits of this configuration is a more efficient transfer of energy from the transmission coils (e.g., coils in the cart) to the receiving coils (e.g., the coils within the portable computing device or patient monitor). Likewise, with a plurality of smaller coils, the entire surface area of the crash cart may be totally or otherwise substantially covered with coils. While not illustrated, yet another embodiment could combine both a large coil and a plurality of smaller coils for added flexibility in where on the surface of the crash cart wireless charging can occur. Similarly, as detailed above, it is understood that wireless charging systems could also be implemented in other configurations such as a charging area in a hospital, doctor's office or ambulance.

While FIGS. 7D and 7E are described with respect to a crash cart, it is understood that wireless charging systems could also be implemented in other places or configurations. For example, wireless charging could be implemented on a workspace, workbench, or other charging areas in a hospital, doctor's office, desk, table or ambulance. Additionally, while not illustrated, the wireless charging system could be integrated into each of the drawers such that devices placed in any of the drawers would be able to wireless charge. A benefit of this configuration is that rescuers would not need to be limited to just a particular drawer or shelf and rescuers would not need to remember to plug in each of the devices. Rather, a single plug for the crash cart could power all of the wireless charging systems.

FIGS. 8A-8D illustrate exemplary implementations of how the portable computing device 116 may be mounted to the patient monitor 109 via 360-degree swivel (detachable) mount 802, according to one embodiment. Alternatively, the mount could be a magnetic or mechanical latch or a ratchet type handle attachment that enables enable angular variability of the portable computing device 116. As illustrated previously in FIG. 1A, the portable computing device 116 should be detachable from the mount 802.

Figure 8A:
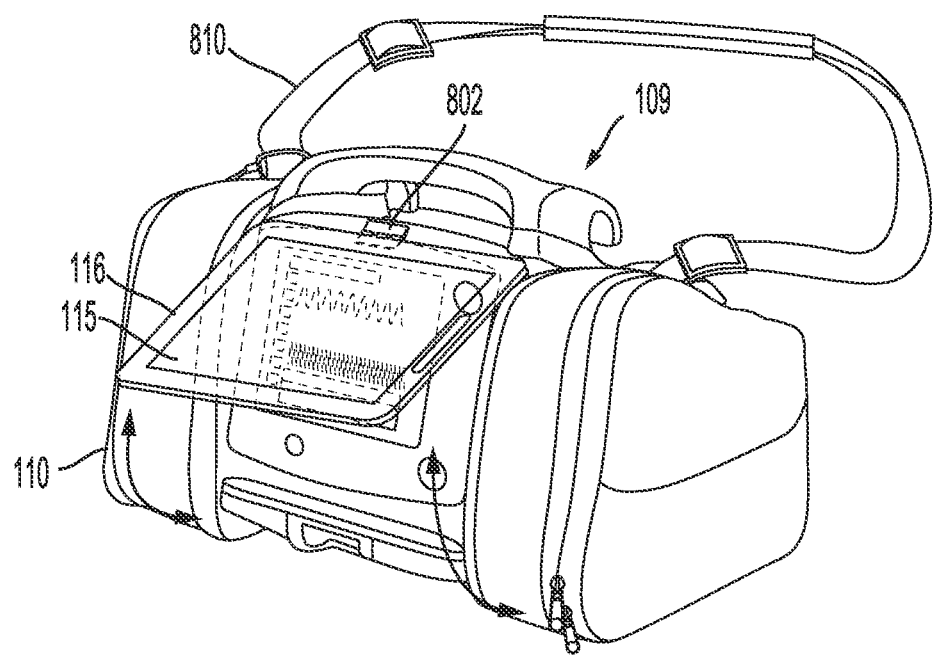
FIG. 8A illustrates how the display screen of the portable computing device can be facing outward to enable the display screen of the portable computing device to function as the primary screen of the patient monitor, in accordance with one implementation.

FIG. 8A further illustrates how the display screen 115 of the portable computing device 116 may be facing outward to enable the display screen 115 of the portable computing device 116 to function as the primary screen of the patient monitor 109. In this configuration, any data that would be typically be displayed on the patient monitor 109 is instead duplicated on the portable computing device. Similarly, any information inputted via the display screen 115 of the portable computing device 116 would be transferred to the patient monitor 109. Alternatively, the display 115 of the portable computing device 116 could be faced inward (toward the defibrillator) to provide some protection of the display 115 (for example, when in transit or not in use).

Figure 8B:
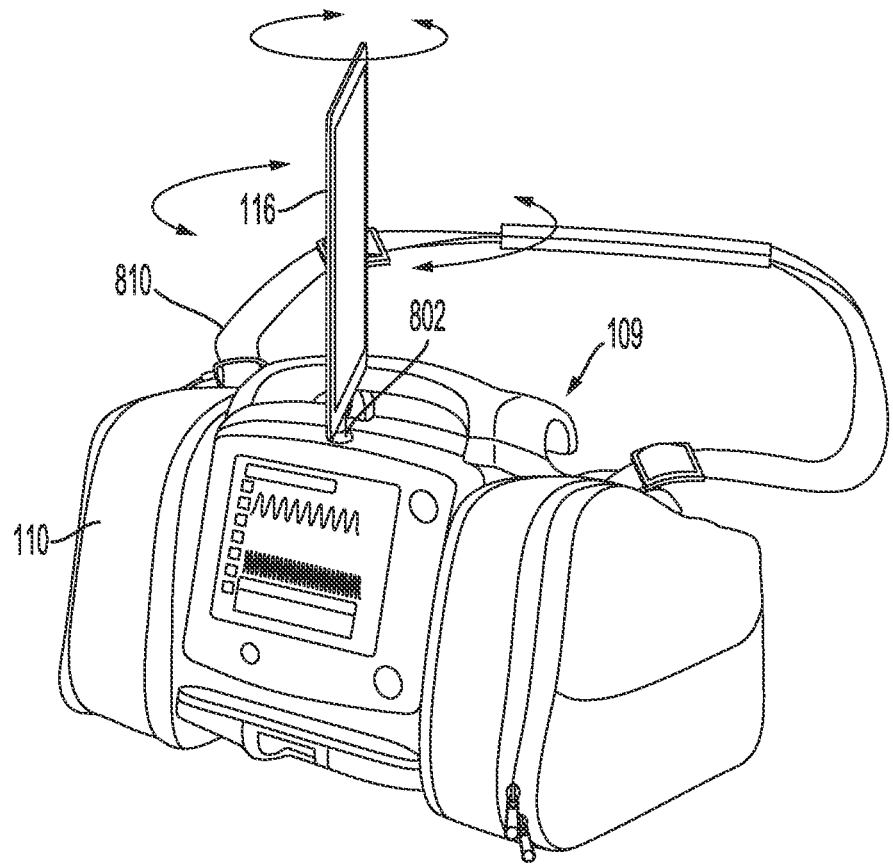
FIGS. 8B and 8C illustrate how the display screen of the portable computing device may be lifted up, and rotated around to enable to the display screen of the portable computing device to function as a secondary screen of the patient monitor, in accordance with one implementation.
Figure 8C:
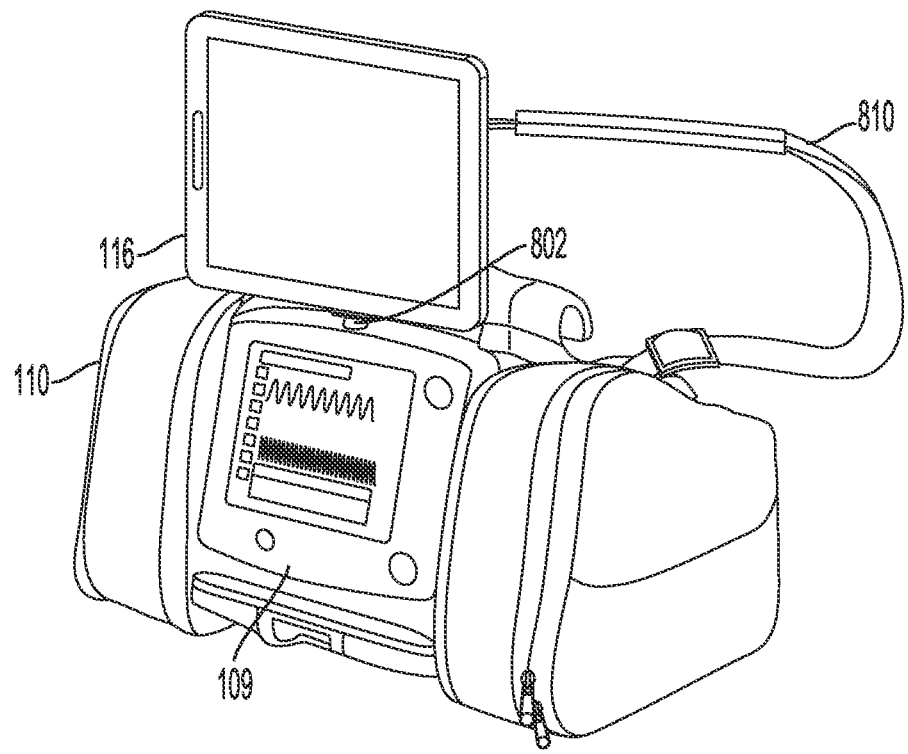

FIGS. 8B and 8C illustrate how the display screen 115 of the portable computing device 116 may be rotated and positioned as a second screen of the patient monitor 109. In one configuration, the display screen 115 of the portable computing device 116 may display different and/or additional information. For instance, in some scenarios, the patient monitor 109 may be connected to one or more peripheral devices (e.g., ventilator, automated chest compressor, ultrasound transducers, or a laryngoscope) and a second screen may be desirable for display the added information. That is, one rescuer may be providing chest compressions. Thus, this rescuer would see information related to chest compressions (e.g., compression rate, compression depth, force, as detailed previously). A second rescuer may be positioned toward the head of the patient and providing ventilations. In this embodiment, the display 115 of the portable computing device 116 would be facing this second rescuer and could display information related to ventilations (e.g., when to ventilate, breaths per minute, oxygen saturation, ETCO2, or possibly a CO2 waveform).

In an alternative embodiment, any data displayed on the patient monitor 109 may be mirrored to the portable computing device 116. As illustrated, the 360 swivel mount 802 enables the portable computing device 116 to be "spun" 360 degrees about its axis. In one example, two rescuers may be positioned in different locations (e.g., one at the patient's head for ventilations and another at the patient's chest performing CPR). By mirroring the information, both rescuers would be able to view the same information regardless of the position of the patient monitor.

Figure 8D:
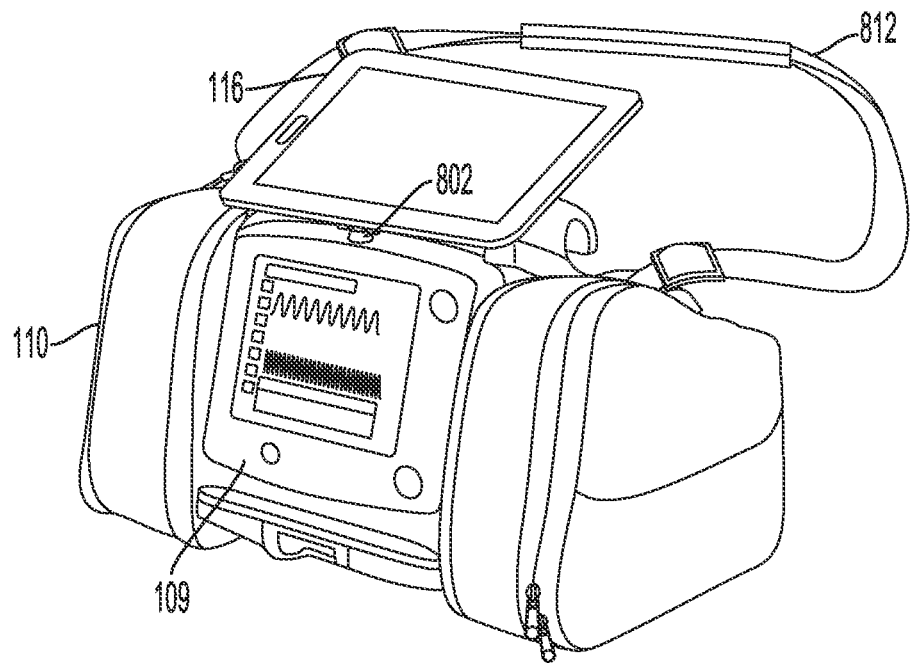
FIG. 8D illustrates another example of how the portable computing device may be positioned such that the portable computing device "lays flat" on the top of the patient monitor 109, according to one embodiment.

FIG. 8D illustrates an example of how the portable computing device 116 may be position such that the portable computing device 116 "lays flat" on the top of the patient monitor 109. This position provides yet another example of how a rescuer may position the portable computing device. Rather than have the portable computing device vertical (i.e., as in FIG. 8C), the rescuers may desire to have the portable computing device horizontal for viewing and/or to input information.

Figure 9A:
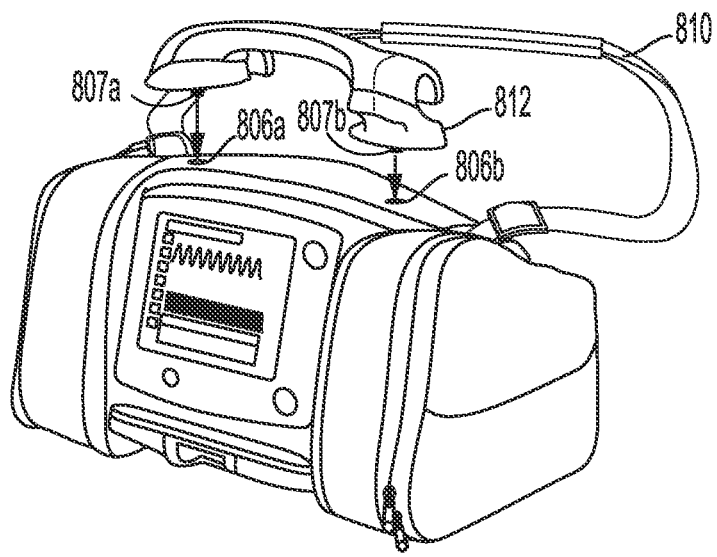
FIGS. 9A and 9B illustrate an embodiment of a patient monitor that may include a detachable handle to enable mounting of a portable computing device in place of the handle.
Figure 9B:
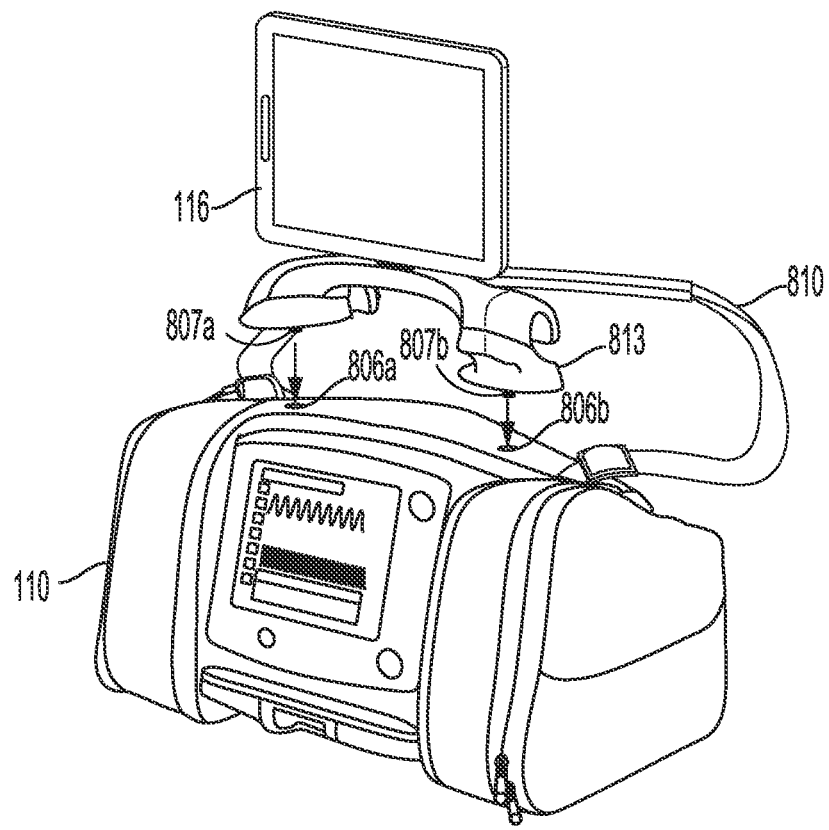

FIGS. 9A and 9B illustrate an alternative embodiment that includes a detachable handle 812. In this example, the handle 812 of the patient monitor 109 is detachable from the patient monitor. In one embodiment, the handle 812 would include a quick release mechanism that causes the handle to be separable from the patient monitor.

Upon detachment, a second handle or other structure 813, that includes an integrated mount for portable computing device 116 may be attached. In some embodiments, the handle 812 may be replaced by a structural mount that does not include a handle (not expressly shown in the figures). In such an example, the patient monitor 109 may be carried via the strap(s) 810 or other carrying method. To aid in attachment, the handles/structures 812, 813 may include alignment components 807a, 807b, which fit into alignment holes 806a, 806b so that the handles/structures may be securely attached in place. As before, the mounting attachment between the handle 813 and the portable computing device 116 would enable the portable computing device 116 to rotate 360 degrees or at least partially around for ease of viewing from multiple perspectives around the device.

Other Considerations:

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device.

A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks.

The computing devices described herein may include, or be operatively coupled to communicate with, one or more mass storage devices for storing data files; such devices include magnetic disks, such as internal hard disks and removable disks; magneto-optical disks; and optical disks.

The terms "machine-readable medium," "computer-readable medium," and "processor-readable medium" as used herein, refer to any medium that participates in providing data that causes a machine to operate in a specific fashion. Using a computer system, various processor-readable media (e.g., a computer program product) might be involved in providing instructions/code to processor(s) for execution and/or might be used to store and/or carry such instructions/code (e.g., as signals).

In many implementations, a processor-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of processor-readable media may be involved in carrying one or more sequences of one or more instructions to one or more processors for execution. Merely by way of example, the instructions may initially be carried on a flash device, a device including persistent memory, and/or a magnetic disk and/or optical disc of a remote computer. A remote computer might load the instructions into its dynamic memory and send the instructions as signals over a transmission medium to be received and/or executed by a computer system.

The computing devices described herein may be part of a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet. The computer system can include clients and servers. A client and server are generally remote from each other and typically interact through a network, such as the described one. The relationship of client and server arises by virtue of computer programs running on the respective computers and having a client-server relationship to each other.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Information and signals may be represented using any of a variety of different technologies and techniques. For example, data, instructions, commands, information, signals, and symbols that may be referenced throughout the above description may be represented by voltages, currents, electromagnetic waves, magnetic fields or particles, optical fields or particles, or any combination thereof.

The methods, systems, and devices discussed above are examples. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure. Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory processor-readable medium such as a storage medium. Processors may perform the described tasks.

Components, functional or otherwise, shown in the figures and/or discussed herein as being connected or communicating with each other are communicatively coupled. That is, they may be directly or indirectly connected to enable communication between them.

As used herein, including in the claims, "and" as used in a list of items prefaced by "at least one of" indicates a disjunctive list such that, for example, a list of "at least one of A, B, and C" means A or B or C or AB or AC or BC or ABC (i.e., A and B and C), or combinations with more than one feature (e.g., AA, AAB, ABBC, etc.). As used herein, including in the claims, unless otherwise stated, a statement that a function or operation is "based on" an item or condition means that the function or operation is based on the stated item or condition and may be based on one or more items and/or conditions in addition to the stated item or condition.

Having described several example configurations, various modifications, alternative constructions, and equivalents may be used without departing from the disclosure. For example, the above elements may be components of a larger system, wherein other rules may take precedence over or otherwise modify the application of the present disclosure. Also, a number of operations may be undertaken before, during, or after the above elements are considered. Also, technology evolves and, thus, many of the elements are examples and do not bound the scope of the disclosure or claims. Accordingly, the above description does not bound the scope of the claims.

Other embodiments are within the scope of the present disclosure. For example, due to the nature of software, functions described above can be implemented using software, hardware, firmware, hardwiring, or combinations of any of these. Features implementing functions may also be physically located at various locations, including being distributed such that portions of functions are implemented at different physical locations.

What is claimed is:

1. A system for use in providing resuscitative care to a patient, the system comprising:
   a defibrillator comprising:
      a power storage device for providing power to the defibrillator, and
      a defibrillator processor configured to:
         transmit at least one signal to activate at least one communications functionality of at least one portable computing device based at least in part on a power related condition associated with the defibrillator, and
         establish at least one bidirectional communication channel with the at least one portable computing device; and
   the at least one portable computing device comprising:
      a portable computing device processor configured to:
         receive the at least one signal to activate the at least one communications functionality of the at least one portable computing device, and
         establish data communication with the defibrillator via the at least one bidirectional communication channel.

2. The system of claim 1, wherein the at least one portable computing device comprises a tablet computer.

3. The system of claim 1, wherein the at least one portable computing device comprises at least one of: a mobile computing device, a mobile phone, a wearable computing device, a laptop, a network device, a network input/output device, and smart glasses.

4. The system of claim 1, wherein the defibrillator is configured to be connected to the at least one portable computing device via a wired connection.

5. The system of claim 1, wherein the defibrillator is configured to be connected to the at least one portable computing device via a wireless connection.

6. The system of claim 1, wherein the at least one portable computing device is configured to display charge level information.

7. The system of claim 1, wherein the at least one portable computing device is configured to display alerts.

8. The system of claim 1, wherein the at least one portable computing device comprises a plurality of portable computing devices.

9. The system of claim 8, wherein the defibrillator is configured to be connected to the plurality of portable computing devices at least in part via at least one wireless network, and wherein at least some of the plurality of portable computing devices are configured to be connected to each other at least in part via the at least one wireless network.

10. The system of claim 9, wherein the at least one wireless network comprises the Internet.

11. The system of claim 9, wherein the at least one wireless network comprises at least one Wi-Fi network.

12. The system of claim 8, wherein at least one of the plurality of portable computing devices is configured to control an interface of the defibrillator to adjust information being displayed.

13. The system of claim 8, wherein at least one of the plurality of portable computing devices is configured to control delivery of treatment by the defibrillator.

14. The system of claim 8, wherein at least some of the plurality of portable computing devices are configured to transfer, to at least some other of the plurality of portable computing devices, at least one of: patient related data and rescue related data.

15. The system of claim 8, wherein at least one of the plurality of portable computing devices is configured to display charge level information relating to at least one other of the plurality of portable computing devices.

16. The system of claim 8, wherein at least one of the plurality of portable computing devices is configured to provide a graphical user interface allowing a user to set at least one of: charging prioritization between at least some of the plurality of portable computing devices, and data transfer prioritization between at least some of the plurality of portable computing devices.

17. The system of claim 1, wherein the at least one portable computing device comprises a plurality of portable computing devices, and wherein the defibrillator processor is configured to establish the at least one bidirectional communication channel between the defibrillator and each of the plurality of portable computing devices, and between each of the plurality of portable computing devices.

18. The system of claim 1, wherein the at least one portable computing device comprises a plurality of portable computing devices, the system comprising:
 a carrying case coupled to the defibrillator, the carrying case comprising:
  a plurality of storage compartments, comprising a storage compartment for each of the plurality of portable computing devices;
  a wireless charging system configured to provide wireless charging for each of the plurality of portable computing devices, the wireless charging system disposed adjacent to each of the plurality of storage compartments; and
 the defibrillator comprising:
  a defibrillator processor configured to detect the presence of each of the plurality of portable computing devices in a storage space of the plurality of storage spaces and to activate the wireless charging system based at least in part on a power related condition associated with the defibrillator.

19. The system of claim 18, wherein the power related condition comprises whether the defibrillator is connected to an external power source.

20. The system of claim 19, wherein the defibrillator processor is configured to deactivate the wireless charging system when the defibrillator is not connected to an external power source.

21. The system of claim 18, wherein the defibrillator processor is configured to prioritize charging between the defibrillator and the plurality of portable computing devices based on set prioritization parameters.

22. The system of claim 18, wherein the defibrillator processor is configured to optimize charging between the defibrillator and the plurality of portable computing devices based on set optimization parameters.

23. The system of claim 22, wherein at least some of the set optimization parameters are user-configurable through one or more graphical user interfaces provided on at least one of the defibrillator and the plurality of portable computing devices.

24. The system of claim 22, wherein the defibrillator processor is configured to optimize charging and data transfer balance between the defibrillator and the plurality of portable computing devices.

25. The system of claim 22, wherein at least one portable computing device of the plurality of portable computing devices is configured to activate charging of the at least one portable computing device in response to a charge level of the at least one portable computing device being below a predefined threshold.

* * * * *